United States Patent
Huh et al.

(10) Patent No.: US 11,737,358 B2
(45) Date of Patent: Aug. 22, 2023

(54) COMPOUND AND ORGANIC LIGHT EMITTING DEVICE COMPRISING SAME

(71) Applicant: LG CHEM, LTD., Seoul (KR)

(72) Inventors: Jungoh Huh, Daejeon (KR); Dong Hoon Lee, Daejeon (KR); Dong Uk Heo, Daejeon (KR); Miyeon Han, Daejeon (KR); Jae Tak Lee, Daejeon (KR); Junghoon Yang, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 391 days.

(21) Appl. No.: 16/761,902

(22) PCT Filed: Mar. 22, 2019

(86) PCT No.: PCT/KR2019/003363
§ 371 (c)(1),
(2) Date: May 6, 2020

(87) PCT Pub. No.: WO2019/182402
PCT Pub. Date: Sep. 26, 2019

(65) Prior Publication Data
US 2020/0303655 A1 Sep. 24, 2020

(30) Foreign Application Priority Data
Mar. 22, 2018 (KR) .................. 10-2018-0033291

(51) Int. Cl.
| | |
|---|---|
| C07D 239/26 | (2006.01) |
| H10K 85/60 | (2023.01) |
| C07D 401/10 | (2006.01) |
| C07D 401/14 | (2006.01) |
| C07D 403/10 | (2006.01) |
| C07D 403/14 | (2006.01) |
| C07D 405/14 | (2006.01) |
| C07D 409/10 | (2006.01) |
| C07F 9/6512 | (2006.01) |
| H10K 50/16 | (2023.01) |
| H10K 50/18 | (2023.01) |
| H10K 50/17 | (2023.01) |

(52) U.S. Cl.
CPC ......... *H10K 85/654* (2023.02); *C07D 239/26* (2013.01); *C07D 401/10* (2013.01); *C07D 401/14* (2013.01); *C07D 403/10* (2013.01); *C07D 403/14* (2013.01); *C07D 405/14* (2013.01); *C07D 409/10* (2013.01); *C07F 9/6512* (2013.01); *H10K 85/6572* (2023.02); *H10K 85/6574* (2023.02); *H10K 85/6576* (2023.02); *H10K 50/16* (2023.02); *H10K 50/171* (2023.02); *H10K 50/18* (2023.02)

(58) Field of Classification Search
CPC ..................................................... C07D 239/26
See application file for complete search history.

(56) References Cited

U.S. PATENT DOCUMENTS

| | | |
|---|---|---|
| 2002/0172420 A1 | 11/2002 | Nicolas |
| 2010/0039026 A1 | 2/2010 | Yang et al. |
| | (Continued) | |

FOREIGN PATENT DOCUMENTS

| | | |
|---|---|---|
| CN | 106967052 | 7/2017 |
| CN | 107827826 | 3/2018 |
| | (Continued) | |

OTHER PUBLICATIONS

Chemical Abstracts Registry No. 105124-20-7, indexed in the Registry file on STN CAS Online on Nov. 8, 1986. (Year: 1986).*

(Continued)

*Primary Examiner* — Laura L Stockton
(74) *Attorney, Agent, or Firm* — Dentons US LLP

(57) ABSTRACT

Provided is a compound of Chemical Formula 1:

HAr-L1-L2-Ar1 wherein:
HAr is one of Chemical Formula A-1 or A-2:

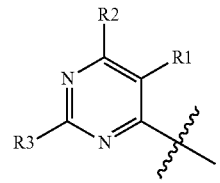

Chemical Formula A-1

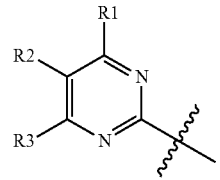

Chemical Formula A-2 one of L1 and L2 is a substituted or unsubstituted monocyclic or polycyclic arylene group, or a substituted or unsubstituted monocyclic or polycyclic heteroarylene group, and the other one is a direct bond; and Ar1 is a cyano group, a substituted or unsubstituted phenyl group; a substituted or unsubstituted biphenyl group; a substituted or unsubstituted pyridinyl group; a substituted or unsubstituted triazinyl group; a substituted or unsubstituted polycyclic aryl group; or a substituted or unsubstituted polycyclic heteroaryl group, and an organic light emitting device comprising the same.

7 Claims, 6 Drawing Sheets

(56) References Cited

U.S. PATENT DOCUMENTS

| | | |
|---|---|---|
| 2011/0248257 A1 | 10/2011 | Kim et al. |
| 2017/0324046 A1 | 11/2017 | Kim et al. |
| 2018/0339967 A1 | 11/2018 | Kim et al. |
| 2018/0354913 A1 | 12/2018 | Jung et al. |

FOREIGN PATENT DOCUMENTS

| | | | | |
|---|---|---|---|---|
| JP | 2018035129 | 3/2018 | | |
| KR | 10-20030012890 | 2/2003 | | |
| KR | 10-20100021908 | 2/2010 | | |
| KR | 10-20100075358 | 7/2010 | | |
| KR | 10-2015-0140241 | 12/2015 | | |
| KR | 10-2016-0052398 | 5/2016 | | |
| KR | 10-20160082067 | 7/2016 | | |
| KR | 10-20170093023 | 8/2017 | | |
| KR | 10-2018-0015794 | 2/2018 | | |
| KR | 10-20180093354 | 8/2018 | | |
| KR | 2018093354 A | * | 8/2018 | ............. C09K 11/06 |
| WO | 2017099430 | 6/2017 | | |
| WO | 2017131380 | 8/2017 | | |
| WO | 2018016898 | 1/2018 | | |

OTHER PUBLICATIONS

Giammanco et al., Farmaco, Edizione Scientifica (1986), 41(3), pp. 225-228. (Year: 1986).*
A machine generated English translation of KR 10-2016-0082067 A (Kim et al.), 2016. (Year: 2016).*

* cited by examiner

【FIG. 1】

| 11 |
|---|
| 8 |
| 7 |
| 6 |
| 4 |
| 3 |
| 2 |
| 1 |

【FIG. 2】

| 11 |
|---|
| 8 |
| 6 |
| 5 |
| 4 |
| 3 |
| 2 |
| 1 |

[FIG. 3]

| |
|---|
| 11 |
| 8 |
| 6b |
| 4b |
| 13 |
| 12 |
| 9a |
| 6a |
| 5 |
| 4a |
| 3 |
| 2 |
| 1 |

[FIG. 4]

| |
|---|
| 11 |
| 9c |
| 6c |
| 4c |
| 13b |
| 12b |
| 9b |
| 6b |
| 4b |
| 13a |
| 12a |
| 9a |
| 6a |
| 5 |
| 4a |
| 3 |
| 2 |
| 1 |

【FIG. 5】

| |
|---|
| 14 |
| 11 |
| 10 |
| 9c |
| 6BFb |
| 4e |
| 4d |
| 13b |
| 12b |
| 9b |
| 6GP |
| 6YGP |
| 6RP |
| 4c |
| 13a |
| 12a |
| 9a |
| 6BFa |
| 4b |
| 4a |
| 3 |
| 2 |
| 1 |

【FIG. 6】

| |
|---|
| 14 |
| 11 |
| 10 |
| 9c |
| 6BFb |
| 4e |
| 4d |
| 13b |
| 12b |
| 9b |
| 6GP |
| 6RP |
| 4c |
| 13a |
| 12a |
| 9a |
| 6BFa |
| 4b |
| 4a |
| 3 |
| 2 |
| 1 |

【FIG. 7】

| |
|:---:|
| 14 |
| 11 |
| 10 |
| 9c |
| 6BFc |
| 4f |
| 4e |
| 13b |
| 12b |
| 9b |
| 6BFb |
| 4d |
| 4c |
| 13a |
| 12a |
| 9a |
| 6BFa |
| 4b |
| 4a |
| 4pa |
| 2 |
| 1 |

【FIG. 8】

| 14 |  |  |
|---|---|---|
| 11 |  |  |
| 10 |  |  |
| 9b |  |  |
| 9a |  |  |
| 6RP | 6GP | 6BF |
| 4R | 4G | 4B |
| 4p |  |  |
| 2 |  |  |
| 1 |  |  |

COMPOUND AND ORGANIC LIGHT EMITTING DEVICE COMPRISING SAME

CROSS-REFERENCE TO RELATED APPLICATIONS

This application is a National Stage Application of International Application No. PCT/KR2019/003363 filed on Mar. 22, 2019, which claims priority to and the benefits of Korean Patent Application No. 10-2018-0033291, filed with the Korean Intellectual Property Office on Mar. 22, 2018, the entire contents of which are incorporated herein by reference.

TECHNICAL FIELD

The present specification relates to a compound of Chemical Formula 1, and an organic light emitting device comprising the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a compound capable of enhancing driving voltage, efficiency and/or lifetime properties of a device, and an organic light emitting device comprising the compound.

Technical Solution

One embodiment of the present specification provides a compound represented by the following Chemical Formula 1:

HAr-L1-L2Ar1.                   Chemical Formula 1

In Chemical Formula 1:

HAr is a group of Chemical Formula A-1 or A-2;

with the proviso that at least one of L1 and L2 is a substituted or unsubstituted monocyclic or polycyclic arylene group, or a substituted or unsubstituted monocyclic or polycyclic heteroarylene group, and the other one is a direct bond;

Ar1 is a cyano group, a substituted or unsubstituted phenyl group, a substituted or unsubstituted biphenyl group, a substituted or unsubstituted pyridinyl group, a substituted or unsubstituted triazinyl group, a substituted or unsubstituted polycyclic aryl group, or a substituted or unsubstituted polycyclic heteroaryl group;

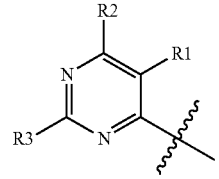

Chemical Formula A-1

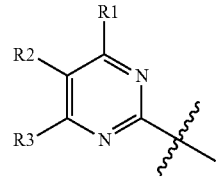

Chemical Formula A-2 wherein in Chemical Formulae A-1 and A-2:

one of R1 to R3 is a phenyl group, and the rest are the same as or different from each other, and each independently is a substituted or unsubstituted cycloalkyl group, a substituted or unsubstituted branched alkyl group, a methyl group, or a substituted or unsubstituted monocyclic heteroaryl group; or two of R1 to R3 are the same as or different from each other and each independently is a phenyl group that is unsubstituted or substituted with an alkyl group, and the remaining one is a substituted or unsubstituted linear or branched alkyl group; a monocyclic or polycyclic aryl group that is unsubstituted or substituted with an alkyl group, an aryl group or an aryloxy group; a pyridinyl group; a dibenzothiophenyl group; a dibenzofuranyl group; or a carbazolyl group; or adjacent groups among R1 to R3 bond to each other to form a substituted or unsubstituted ring; and ╋ is a site bonding to L1 of Chemical Formula 1.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the compound of Chemical Formula 1.

Advantageous Effects

An organic light emitting device comprising a compound of Chemical Formula 1 according to the present specification as a material of an organic material layer has properties of low driving voltage, high efficiency and/or long lifetime.

DESCRIPTION OF DRAWINGS

FIGS. 1, 2 and 8 illustrate examples of an organic light emitting device according to one embodiment of the present specification.

FIGS. 3 to 7 illustrate examples of an organic light emitting device including two or more stacks.

DETAILED DESCRIPTION

Hereinafter, the present specification will be described in more detail.

One embodiment of the present specification provides a compound of Chemical Formula 1.

Groups of Chemical Formulae A-1 and A-2 according to one embodiment of the present specification have substituents bonding to all three $sp^2$ positions of R1 to R3, whereas the following structures, an existing pyrimidinyl core, have substituents bonding to R and R', two positions of three $sp^2$ positions:

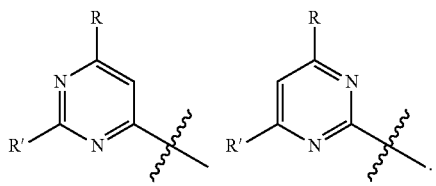

Accordingly, groups of Chemical Formulae A-1 and A-2 according to one embodiment of the present specification are a new pyrimidinyl group having a site vulnerable to a chemical reaction removed. This means that chemical stability of compounds including the groups of Chemical Formulae A-1 and A-2 is enhanced. When including the compound of Chemical Formula 1 in an organic material layer of an organic light emitting device, probability of dissociation caused by electrons or holes generated when driving the organic light emitting device significantly decreases, and as a result, a lowered voltage, increased efficiency and greatly enhanced lifetime properties can be obtained in the organic light emitting device.

In addition, Chemical Formulae A-1 and A-2 according to one embodiment of the present specification include substituents at the three $sp^2$ positions, and therefore, more readily control electron quantities than existing pyrimidinyl groups illustrated above, and both efficiency and lifetime can be enhanced in an organic light emitting device including the structure in an organic material layer thereof.

Chemical Formulae A-1 and A-2 according to one embodiment of the present specification include substituents at the three $sp^2$ positions, which increases a molecular weight of Chemical Formula 1, and therefore, when forming a film using the compound of Chemical Formula 1, an effect of hardening the film quality is obtained.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a cyano group, a nitro group, an alkyl group, a cycloalkyl group, an alkoxy group, an aryloxy group, an alkylthioxy group, an arylthioxy group, an amine group, a phosphine oxide group, an aryl group, and a heteroaryl group, being substituted with a substituent linking two or more substituents among the substituents selected from the group, two substituents selected from the group bonding to each other to form a spiro structure, or having no substituents. For example, "a substituent linking two or more substituents" can include a biphenyl group. In other words, a biphenyl group can be an aryl group, or interpreted as a substituent linking two phenyl groups.

In the definition of the term "substituted or unsubstituted", the "two substituents selected from the group bonding to each other to form a spiro structure" means "'any substituent selected from the group' spiro bonding to 'another substituent substituting an atom substituted with the corresponding substituent' to form a spiro ring".

In the present specification, ┼ means a site bonding to other substituents or bonding sites.

In the present specification, the halogen group can be a fluoro group (—F), a chloro group (—Cl), a bromo group (—Br) or an iodo group (—I).

In the present specification, the alkyl group can be linear or branched, and although not particularly limited thereto, the number of carbon atoms is preferably from 1 to 30. Specific examples thereof include methyl, ethyl, propyl, n-propyl, isopropyl, butyl, n-butyl, isobutyl, tert-butyl, sec-butyl, 1-methylbutyl, 1-ethylbutyl, pentyl, n-pentyl, isopentyl, neopentyl, tert-pentyl, hexyl, n-hexyl, 1-methyl-pentyl, 2-methylpentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methyl-heptyl, 2-ethylhexyl, 2-propylpentyl, n-nonyl, 2,2-dimethyl-heptyl, 1-ethylpropyl, 1,1-dimethylpropyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group can be linear, branched or cyclic. The number of carbon atoms of the alkoxy group is not particularly limited, but is preferably from 1 to 30. Specific examples thereof can include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethyl-butyloxy, 2-ethylbutyloxy, n-octyloxy, n-nonyloxy, n-decyloxy, benzyloxy, p-methylbenzyloxy and the like, but are not limited thereto.

In the present specification, the amine group can be selected from the group consisting of —NH₂, an N-alkylamine group, an N,N-dialkylamine group, an N,N-(alkyl) (aryl) amine group, an N,N-(alkyl)(heteroaryl)amine group, an N-arylamine group, an N,N-diarylamine group, an N,N-(aryl) (heteroaryl)-amine group, an N-heteroarylamine group, and an N,N-diheteroarylamine group, and although not particularly limited thereto, the number of carbon atoms is preferably from 1 to 30. Specific examples of the amine group can include a methylamine group, a dimethylamine group, an ethylamine group, a diethylamine group, a phenylamine group, a naphthylamine group, a biphenylamine group, an anthracenylamine group, a (9-methyl-anthracenyl) amine group, a diphenylamine group, a ditolylamine group, an N,N-(phenyl) (tolyl) amine group, an N,N-(phenyl) (biphenyl) amine group, an N,N-(phenyl) (naphthyl)amine group, an N,N-(biphenyl) (naphthyl) amine group, an N,N-(naphthyl)-(fluorenyl)amine group, an N,N-(phenyl) (phenanthrenyl)amine group, an N,N-(biphenyl) (phenanthrenyl)amine group, an N,N-(phenyl)(fluorenyl) amine group, an N,N-(phenyl) (terphenyl)-amine group, an N,N-(phenanthrenyl) (fluorenyl)amine group, an N,N-(biphenyl) (fluorenyl)amine group and the like, but are not limited thereto.

In the present specification, the N,N-(alkyl)(aryl)amine group means an amine group in which N of the amine group is substituted with an alkyl group and an aryl group.

In the present specification, the N,N-(aryl)-(heteroaryl) amine group means an amine group in which N of the amine group is substituted with an aryl group and a heteroaryl group.

In the present specification, the N,N-(alkyl)-(heteroaryl) amine group means an amine group in which N of the amine group is substituted with an alkyl group and a heteroaryl group.

In the present specification, examples of the alkylamine group include a substituted or unsubstituted monoalkylamine group or a substituted or unsubstituted dialkylamine group. The alkyl group in the alkylamine group can be a linear or branched alkyl group. The alkylamine group including two or more alkyl groups can include linear alkyl groups, branched alkyl groups, or both linear alkyl groups and branched alkyl groups. For example, the alkyl group in the alkylamine group can be selected from among the examples of the alkyl group described above.

In the present specification, the alkyl group in the N-alkylamine group, the N,N-dialkylamine group, the alkylthioxy group, the N,N-(alkyl) (aryl)amine group and the N,N-(alkyl) (heteroaryl)amine group is the same as the examples of the alkyl group described above. Specific examples of the alkylthioxy group can include a methylthioxy group, an ethylthioxy group, a tert-butylthioxy group, a hexylthioxy group, an octylthioxy group and the like, but are not limited thereto.

In the present specification, specific examples of the phosphine oxide group can include an alkylphosphine oxide group, an arylphosphine oxide group and the like, and more specifically, a diphenylphosphine oxide group, a dinaphthylphosphine oxide group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Specific examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Specific example of the polycyclic aryl group can include a naphthyl group, an anthracenyl group, a phenanthrenyl group, a triphenylenyl group, a pyrenyl group, a phenalenyl group, a perylenyl group, a chrysenyl group, a fluorenyl group, a fluoranthenyl group and the like, but are not limited thereto.

In the present specification, the fluorenyl group can be substituted, and two substituents can bond to each other to form a spiro structure.

When the fluorenyl group is substituted,

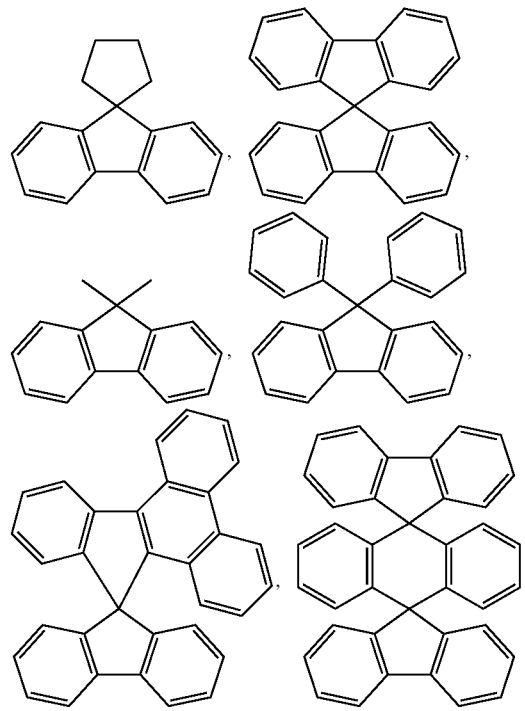

and the like can be included. However, the structure is not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the aryl group in the aryloxy group, the arylthioxy group, the N,N-(alkyl) (aryl)amine group, the N-arylamine group, the N-diarylamine group and the N,N-(aryl) (heteroaryl)amine group is the same as the examples of the aryl group described above. Specific examples of the aryloxy group can include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthrenyloxy group, a 3-phenanthrenyloxy group, a 9-phenanthrenyloxy group and the like. Specific examples of the arylthioxy group can include a phenylthioxy group, a 2-methylphenylthioxy group, a 4-tert-butylphenylthioxy group and the like. However, the aryloxy group and the arylthioxy group are not limited thereto.

In the present specification, examples of the arylamine group include a substituted or unsubstituted monoarylamine group, or a substituted or unsubstituted diarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the heteroaryl group is a group including one or more atoms that are not carbon (heteroatom), and specifically, the heteroatom can include one or more atoms selected from the group consisting of O, N, Se and S. The number of carbon atoms is not particularly limited, but is preferably from 2 to 30, and the heteroaryl group can be monocyclic or polycyclic. Examples of the heterocyclic group can include a thiophenyl group, a furanyl group, a pyrrolyl group, an imidazolyl group, a triazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolyl group, a quinoxalinyl group, a phthalazinyl group, a pyridopyrimidinyl group, a pyridopyrazinyl group, a pyrazinopyrazinyl group, a pyridoindolyl group, a benzothienopyrimidinyl group, an indenocarbazolyl group, an isoquinolinyl group, an indolyl group, a carbazolyl group, a benzoxazolyl group, a benzimidazolyl group, a benzothiazolyl group, a benzocarbazolyl group, a benzothiophenyl group, a dibenzothiophenyl group, a benzofuranyl group, a phenanthridinyl group, a phenanthrolinyl group, an isoxazolyl group, a thiadiazolyl group, a phenothiazinyl group, a dibenzofuranyl group and the like, but are not limited thereto.

In the present specification, examples of the heteroarylamine group include a substituted or unsubstituted monoheteroarylamine group, or a substituted or unsubstituted diheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the heteroaryl group in the N-heteroarylamine group, the N,N-diheteroarylamine group, the N,N-(aryl) (heteroaryl)amine group and the N,N-(alkyl) (heteroaryl) amine group are the same as the examples of the heteroaryl group described above.

In the present specification, the arylene group means an aryl group having two bonding sites, that is, a divalent group. Descriptions on the aryl group provided above can be applied thereto except for each being a divalent group.

In the present specification, the heteroarylene group means a heteroaryl group having two bonding sites, that is, a divalent group. Descriptions on the heteroaryl group provided above can be applied thereto except for each being a divalent group.

In the present specification, the "ring" in the substituted or unsubstituted ring famed by adjacent groups bonding to each other means a substituted or unsubstituted hydrocarbon ring, or a substituted or unsubstituted heteroring.

In the present specification, the hydrocarbon ring can be an aromatic hydrocarbon ring, an aliphatic hydrocarbon ring, or a fused ring of an aromatic hydrocarbon ring and an aliphatic hydrocarbon ring. In one embodiment, the aliphatic hydrocarbon ring and the aromatic hydrocarbon ring can be selected from among the examples of the cycloalkyl group and the aryl group, respectively, except for those that are not monovalent.

In the present specification, the aromatic ring can be monocyclic or polycyclic, and can be selected from among the examples of the aryl group or the heteroaryl group except for those that are not monovalent.

In the present specification, the heterering includes one or more atoms that are not carbon (heteroatom), and specifically, the heteroatom can include one or more atoms selected form the group consisting of O, N, Se and S. The heterering can be monocyclic or polycyclic.

According to one embodiment of the present specification, Chemical Formula 1 is one of the following Chemical Formula 1-1 or 1-2.

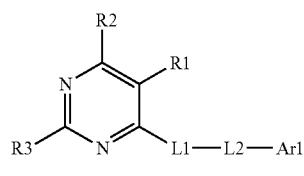

Chemical Formula 1-1

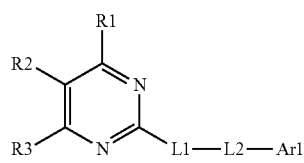

Chemical Formula 1-2

In Chemical Formulae 1-1 and 1-2,

L1, L2 and Ar1 have the same definitions as in Chemical Formula 1, and

R1 to R3 have the same definitions as in Chemical Formulae A-1 and A-2.

According to one embodiment of the present specification, at least one selected from the group consisting of L1 and L2 is a substituted or unsubstituted phenylene group, a substituted or unsubstituted $C_{10-20}$ arylene group, or a substituted or unsubstituted $C_{2-20}$ monocyclic or polycyclic heteroarylene group, and the other one is a direct bond.

According to one embodiment of the present specification, at least one selected from the group consisting of L1 and L2 is a substituted or unsubstituted phenylene group, a substituted or unsubstituted $C_{10-15}$ arylene group, or a substituted or unsubstituted $C_{2-15}$ monocyclic or polycyclic heteroarylene group, and the other one is a direct bond.

According to one embodiment of the present specification, at least one selected from the group consisting of L1 and L2 is a substituted or unsubstituted phenylene group, a substituted or unsubstituted polycyclic arylene group, a substituted or unsubstituted divalent pyridinyl group, a substituted or unsubstituted divalent triazinyl group, or a substituted or unsubstituted divalent polycyclic heteroarylene group, and the other one is a direct bond.

According to one embodiment of the present specification, at least one selected from the group consisting of L1 and L2 is a monocyclic or polycyclic arylene group that is unsubstituted or substituted with an alkyl group, an aryl group substituted with a cyano group, an aryl group substituted with a fluoroalkoxy group, a heteroaryl group substituted with an alkyl group, an aryl group or a heteroaryl group, or a monocyclic or polycyclic heteroarylene group that is unsubstituted or substituted with an alkyl group, an aryl group, a heteroaryl group or an arylheteroaryl group, and the other one is a direct bond.

According to one embodiment of the present specification, at least one selected from the group consisting of L1 and L2 is a phenylene group that is unsubstituted or substituted with an aryl group substituted with a cyano group, an aryl group substituted with a fluoroalkoxy group, a heteroaryl group substituted with an alkyl group, an aryl group or a heteroaryl group; a biphenylene group; a divalent naphthyl group that is unsubstituted or substituted with a cyano group; a divalent fluorenyl group that is unsubstituted or substituted with an alkyl group or an aryl group; a divalent dibenzofuranyl group; a divalent dibenzothiophenyl group; a divalent carbazolyl group that is unsubstituted or substituted with an aryl group, a heteroaryl group or an arylheteroaryl group; or a divalent spirofluorenexanthenyl group, and the other one is a direct bond.

According to one embodiment of the present specification, at least one selected from the group consisting of L1 and L2 is a divalent biphenyl group; a phenylene group that is unsubstituted or substituted with a cyanophenyl group, a trifluoromethoxyphenyl group, a triphenylenyl group, a pyridinyl group that is unsubstituted or substituted with a methyl group, a dibenzothiophenyl group or a carbazolyl group; a divalent naphthyl group; a divalent spiro[fluorene-9,9'xanthen]yl group; a divalent 9,9'-dimethylfluorenyl group; a divalent 9,9'-diphenylfluorenyl group; a divalent dibenzofuranyl group; a divalent dibenzothiophenyl group; or a divalent carbazolyl group that is unsubstituted or substituted with a phenyl group, a dibenzothiophenyl group or a phenylcarbazolyl group, and the other one is a direct bond.

According to one embodiment of the present specification, Ar1 is a cyano group; a phenyl group that is unsubstituted or substituted with a cyano group, an arylphosphine oxide group, an aryl group substituted with a fluoroalkoxy group, an aryl group or a heteroaryl group; a biphenyl group that is unsubstituted or substituted with a cyano group; a polycyclic aryl group that is unsubstituted or substituted with a cyano group, an alkyl group or an aryl group; a pyridinyl group that is unsubstituted or substituted with an alkyl group; a triazinyl group that is unsubstituted or substituted with an alkyl group or an aryl group; or a polycyclic heteroaryl group that is unsubstituted or substituted with a cyano group, an alkyl group or an aryl group.

According to one embodiment of the present specification, Ar1 is a cyano group; a phenyl group that is unsubstituted or substituted with a cyano group, an arylphosphine oxide group, an aryl group substituted with a fluoroalkoxy group, an aryl group, a pyridinyl group, a triazinyl group or a polycyclic heteroaryl group; a biphenyl group that is unsubstituted or substituted with a cyano group; a polycyclic aryl group that is unsubstituted or substituted with a cyano group, an alkyl group or an aryl group; a pyridinyl group that is unsubstituted or substituted with an alkyl group; a triazinyl group that is unsubstituted or substituted with an alkyl group or an aryl group; or a polycyclic heteroaryl group that is unsubstituted or substituted with a cyano group, an alkyl group or an aryl group.

According to one embodiment of the present specification, Ar1 is a cyano group; a phenyl group that is unsubstituted or substituted with a cyano group, an arylphosphine oxide group, an aryl group substituted with a fluoroalkoxy group, an aryl group or a heteroaryl group; a biphenyl group that is unsubstituted or substituted with a cyano group; a naphthyl group that is unsubstituted or substituted with a cyano group; a phenanthrenyl group; a fluoranthenyl group; a fluorenyl group that is unsubstituted or substituted with an alkyl group or an aryl group; a triphenylenyl group; a spiro[fluorene-9,9'xanthen]yl group that is unsubstituted or substituted with a cyano group; a pyridinyl group that is unsubstituted or substituted with an alkyl group; a triazinyl group that is unsubstituted or substituted with an alkyl group or an aryl group; a quinolinyl group; an indenocarbazolyl group that is unsubstituted or substituted with an alkyl group; a beta-carbolinyl group; a pyridoindolyl group; a benzothienopyrimidinyl group that is unsubstituted or substituted with an aryl group; a benzimidazolyl group that is unsubstituted or substituted with an aryl group; a benzoxazolyl group; a benzothiazolyl group; a dibenzofuranyl group; a dibenzothiophenyl group; a carbazolyl group that is unsubstituted or substituted with a cyano group or an aryl group; or a phenanthrolinyl group.

According to one embodiment of the present specification, Ar1 is a cyano group; a phenyl group that is unsubstituted or substituted with a cyano group, a diphenylphosphine oxide group, a phenyl group substituted with a trifluoromethoxy group, a phenyl group, a naphthyl group, a biphenyl group, a pyridinyl group, a dibenzofuranyl group, a dibenzothiophenyl group or a carbazolyl group; a biphenyl group that is unsubstituted or substituted with a cyano group; a naphthyl group that is unsubstituted or substituted with a cyano group; a phenanthrenyl group; a fluoranthenyl group; a fluorenyl group that is unsubstituted or substituted with a methyl group or a phenyl group; a triphenylenyl group; a spiro[fluorene-9,9'xanthen]yl group that is unsubstituted or substituted with a cyano group; a pyridinyl group that is unsubstituted or substituted with a methyl group; a triazinyl group that is unsubstituted or substituted with a methyl group or a phenyl group; a quinolinyl group; an indenocarbazolyl group that is unsubstituted or substituted with a methyl group; a beta-carbolinyl group; a pyridoindolyl group; a benzothienopyrimidyl group that is unsubstituted or substituted with a phenyl group; a benzimidazolyl group that is unsubstituted or substituted with a phenyl group; a benzoxazolyl group; a benzothiazolyl group; a dibenzofuranyl group; a dibenzothiophenyl group; a carbazolyl group that is unsubstituted or substituted with a cyano group or a phenyl group; or a phenanthrolinyl group.

According to some embodiments of the present specification, one of R1 to R3 is a phenyl group, and the remaining two are the same as or different from each other and each independently is a cycloalkyl group, a branched alkyl group, a methyl group, or a monocyclic heteroaryl group.

According to some embodiments of the present specification, one of R1 to R3 is a phenyl group, and the remaining two are the same as or different from each other and each independently is a cyclohexyl group, a methyl group, a 1-methylpropyl group, or a pyridinyl group.

According to some embodiments of the present specification, two of R1 to R3 are the same as or different from each other and each independently is a phenyl group that is unsubstituted or substituted with an alkyl group, and the remaining one is an alkyl group; an aryl group that is unsubstituted or substituted with an alkyl group, an aryl group or an aryloxy group; a pyridinyl group; a dibenzothiophenyl group; a dibenzofuranyl group; or a carbazolyl group.

According to some embodiments of the present specification, two of R1 to R3 are the same as or different from each other and each independently is a phenyl group that is unsubstituted or substituted with an alkyl group; and the remaining one is an alkyl group; a phenyl group that is unsubstituted or substituted with an alkyl group, an aryl group or an aryloxy group; a fluorenyl group that is unsubstituted or substituted with an alkyl group or an aryl group; a phenanthrenyl group; a pyridinyl group; a dibenzothiophenyl group; a dibenzofuranyl group; or a carbazolyl group.

According to some embodiments of the present specification, two of R1 to R3 are the same as or different from each other and each independently is a phenyl group that is unsubstituted or substituted with an alkyl group; and the remaining one is an alkyl group; a phenyl group; a phenyl group substituted with an aryl group or an aryloxy group; a fluorenyl group that is unsubstituted or substituted with an alkyl group or an aryl group; a phenanthrenyl group; a pyridinyl group; a dibenzothiophenyl group; a dibenzofuranyl group; or a carbazolyl group.

According to some embodiments of the present specification, two of R1 to R3 are the same as or different from each other and each independently is a phenyl group that is unsubstituted or substituted with a methyl group; and the remaining one is a phenyl group that is unsubstituted or substituted with a methyl group, a phenoxy group, a phenyl group or a fluoranthenyl group; a phenanthrenyl group; a fluorenyl group that is unsubstituted or substituted with a methyl group; a methyl group; an n-propyl group; an iso-propyl group; a 9H-carbazol-9-yl group; a dibenzofuranyl group; or a dibenzothiophenyl group.

According to some embodiments of the present specification, adjacent groups among R1 to R3 bond to each other to form a heteroring.

According to some embodiments of the present specification, adjacent groups among R1 to R3 bond to each other to form a tribenzoperimidine ring.

According to some embodiments of the present specification, R1 to R3 are each independently is a phenyl group, and R1 to R3 bond to each other to form a tribenzoperimidine ring.

According to some embodiments of the present specification, at least one of L1 and L2 is a substituted or unsubstituted polycyclic arylene group, or a substituted or unsubstituted monocyclic or polycyclic heteroarylene group; and Ar1 is a cyano group, a substituted or unsubstituted pyridinyl group, a substituted or unsubstituted triazinyl group, a substituted or unsubstituted polycyclic aryl group, or a substituted or unsubstituted polycyclic heteroaryl group.

According to one embodiment of the present specification, the compound of Chemical Formula 1 is selected from among the following compounds:

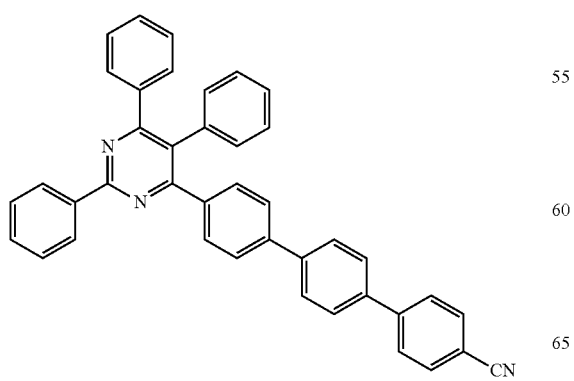

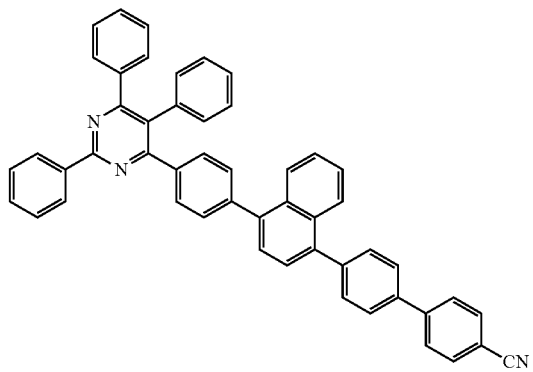

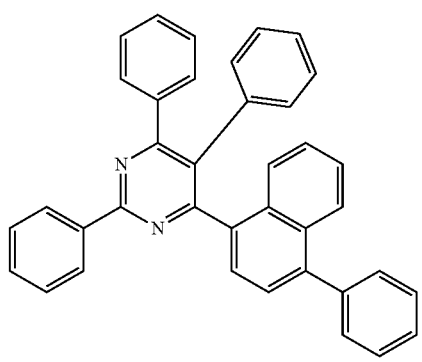

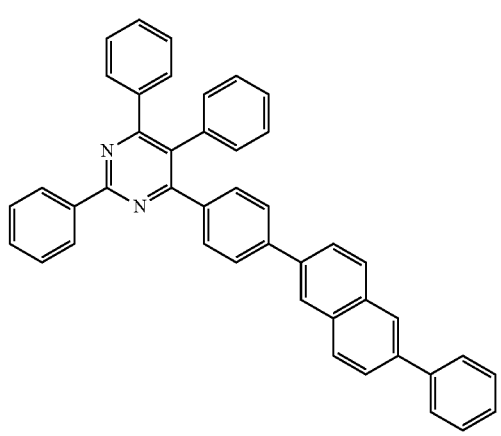

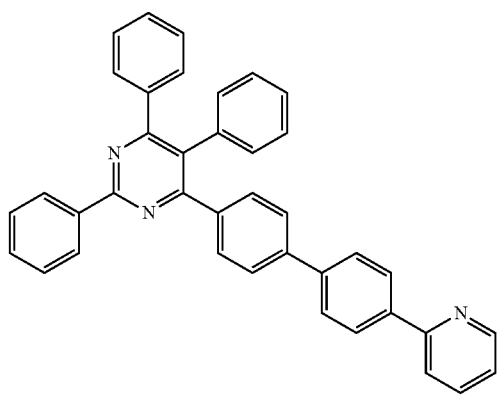

-continued
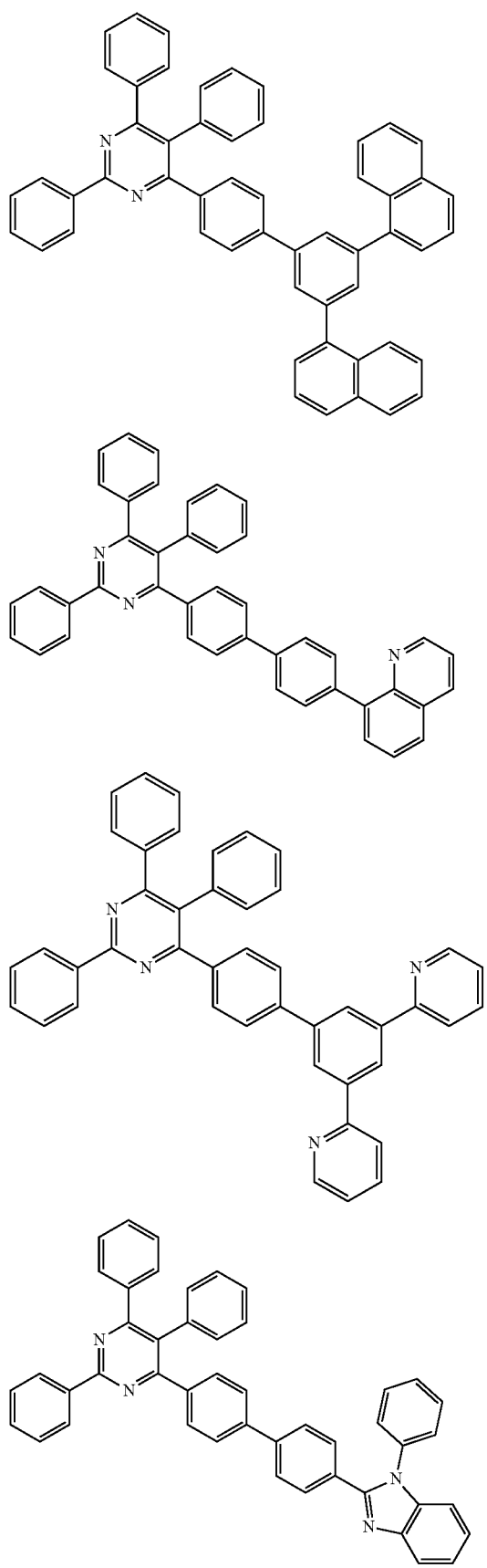
-continued
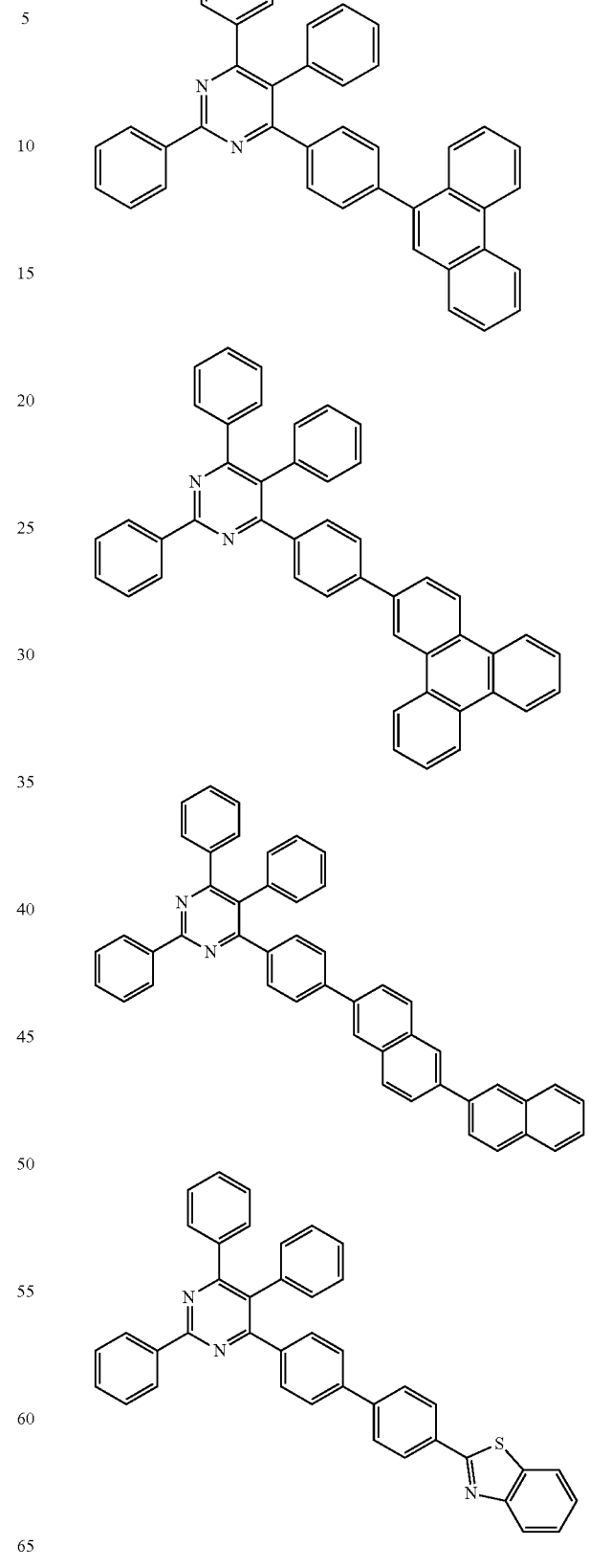

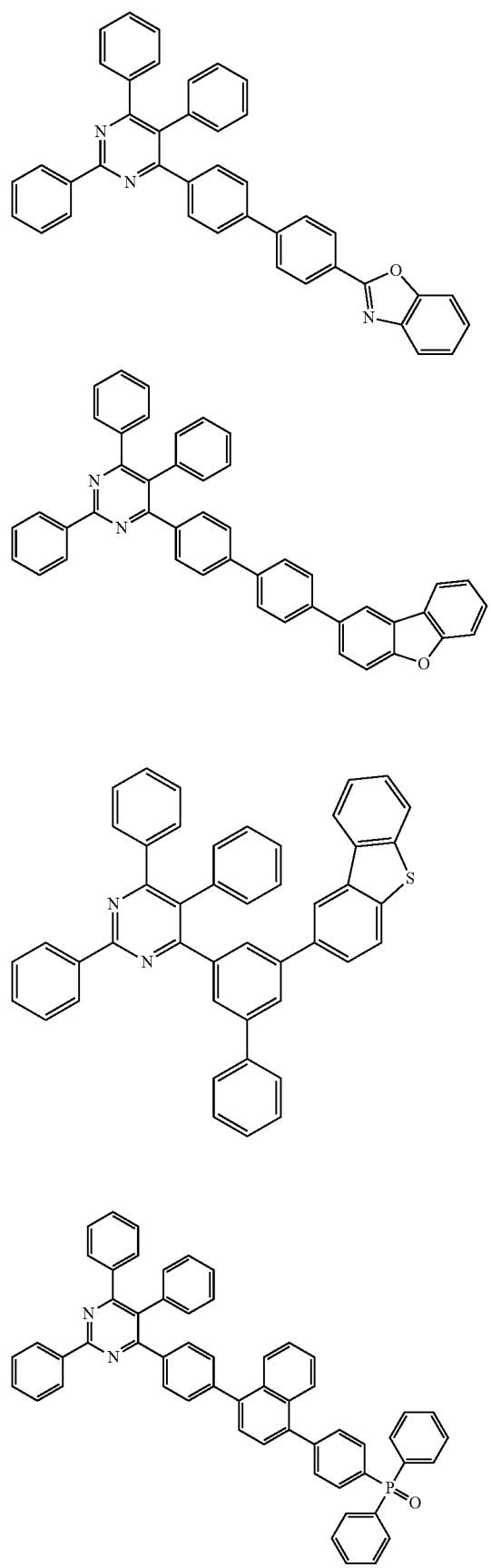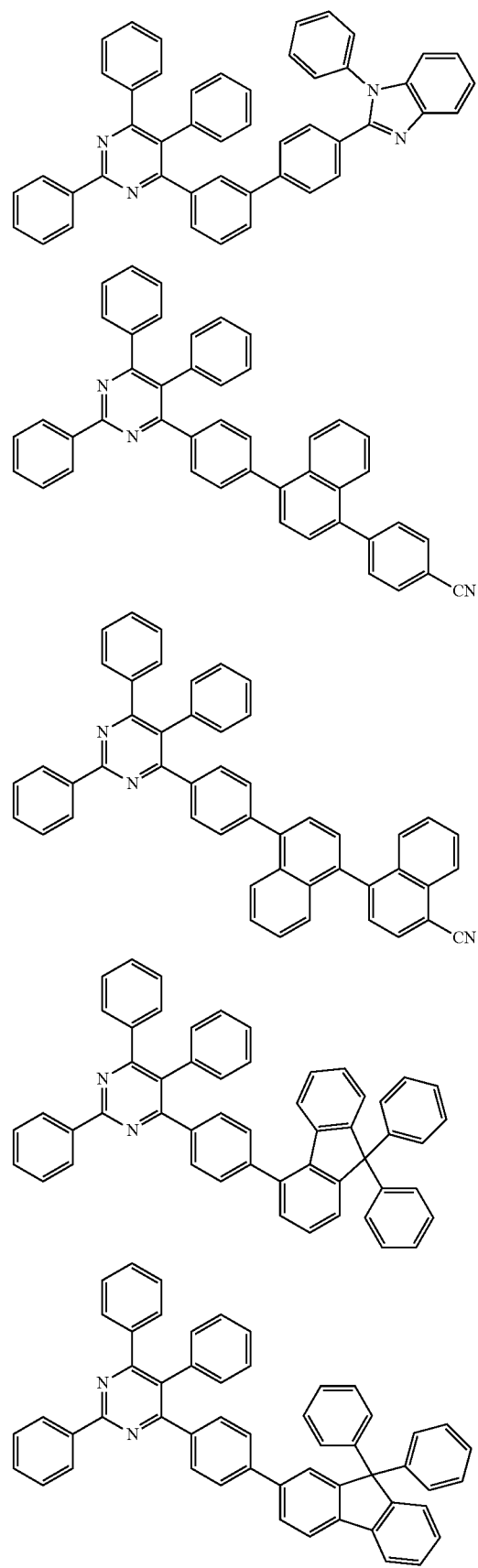

-continued
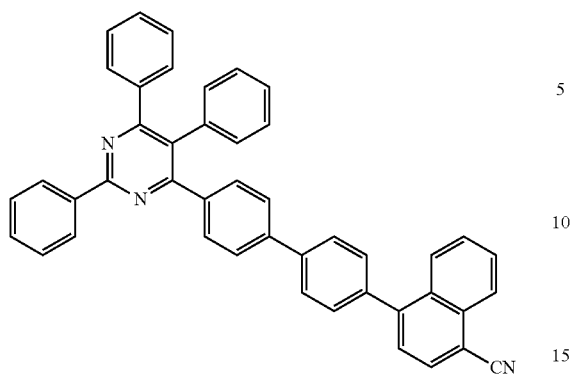
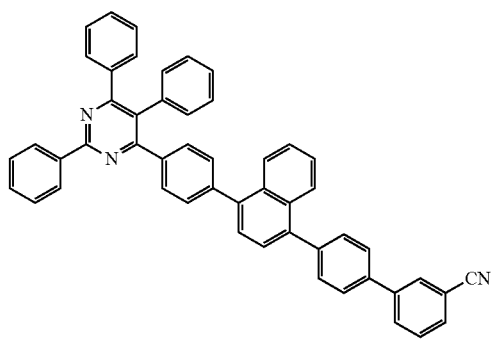
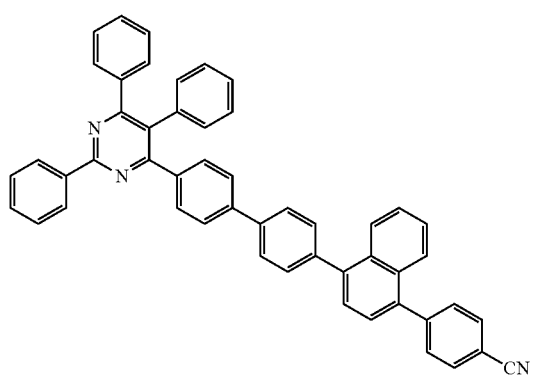
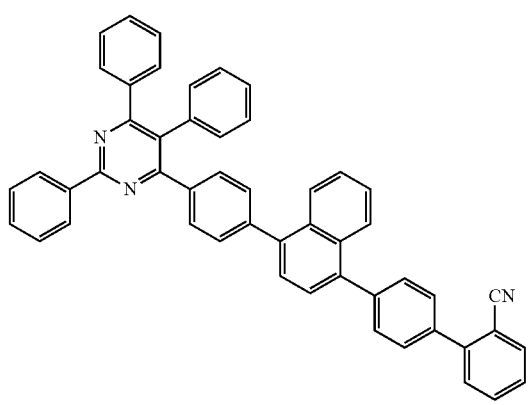
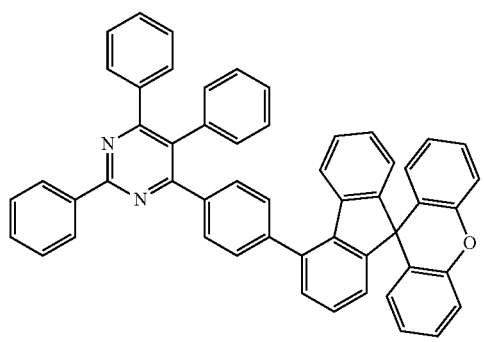
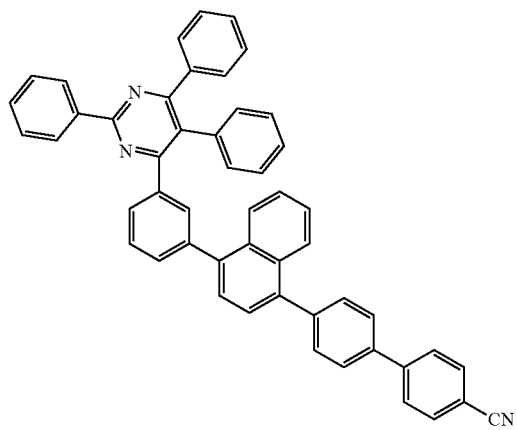
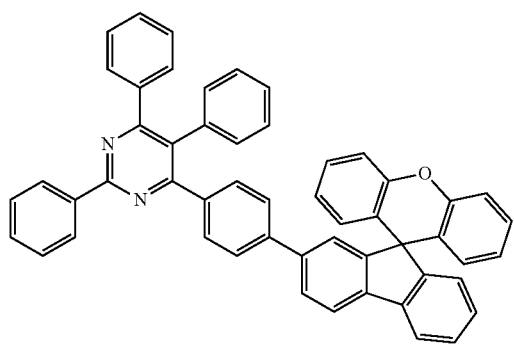
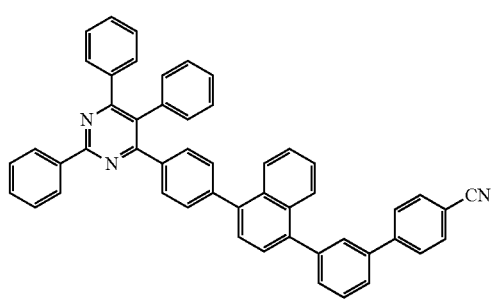

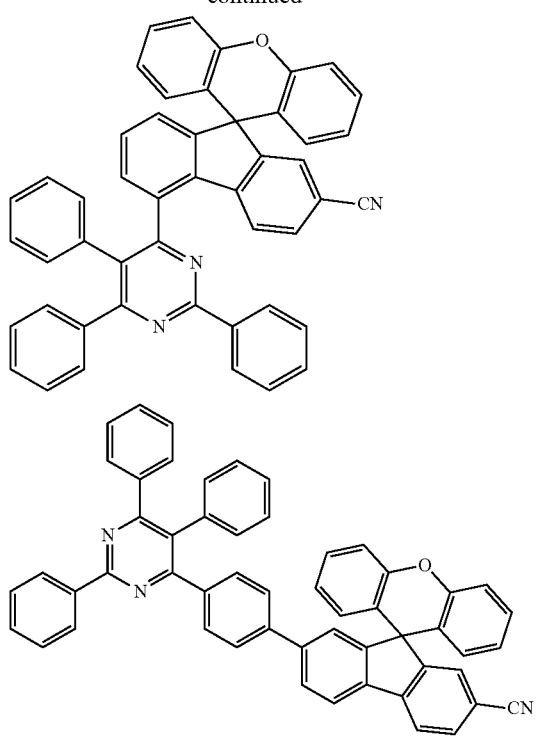
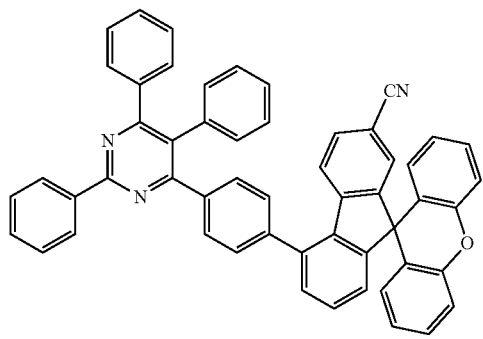
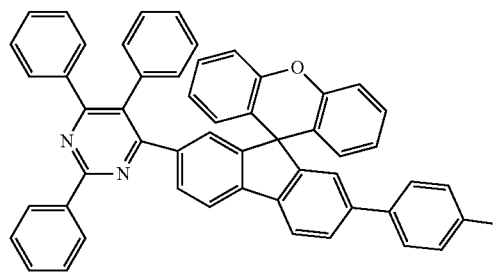
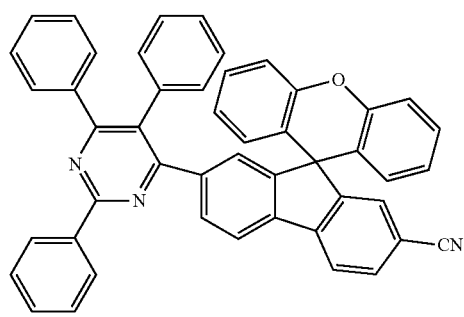
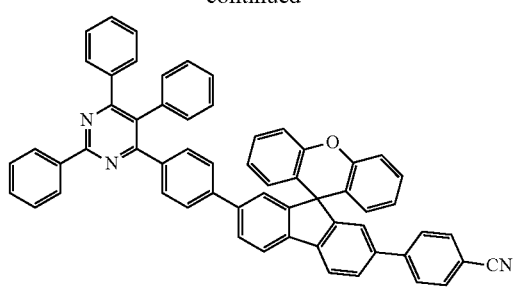
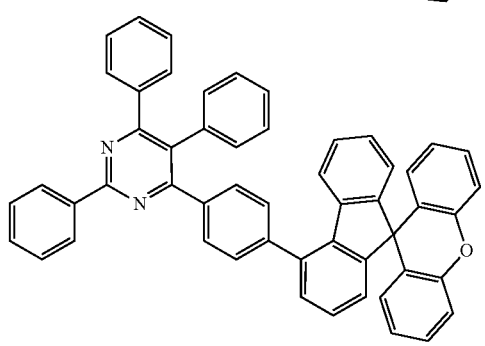
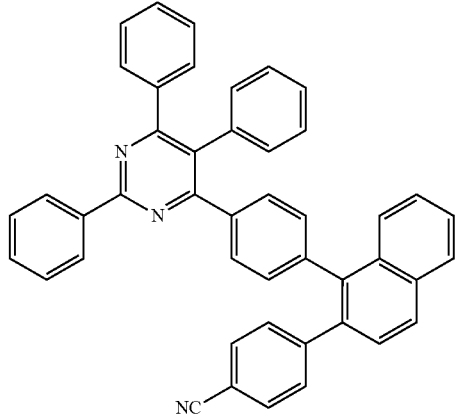
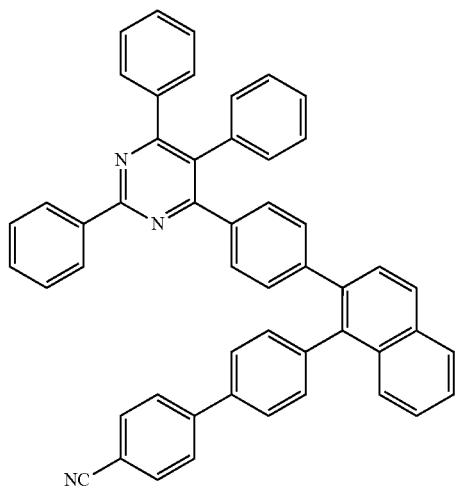

US 11,737,358 B2
21
-continued
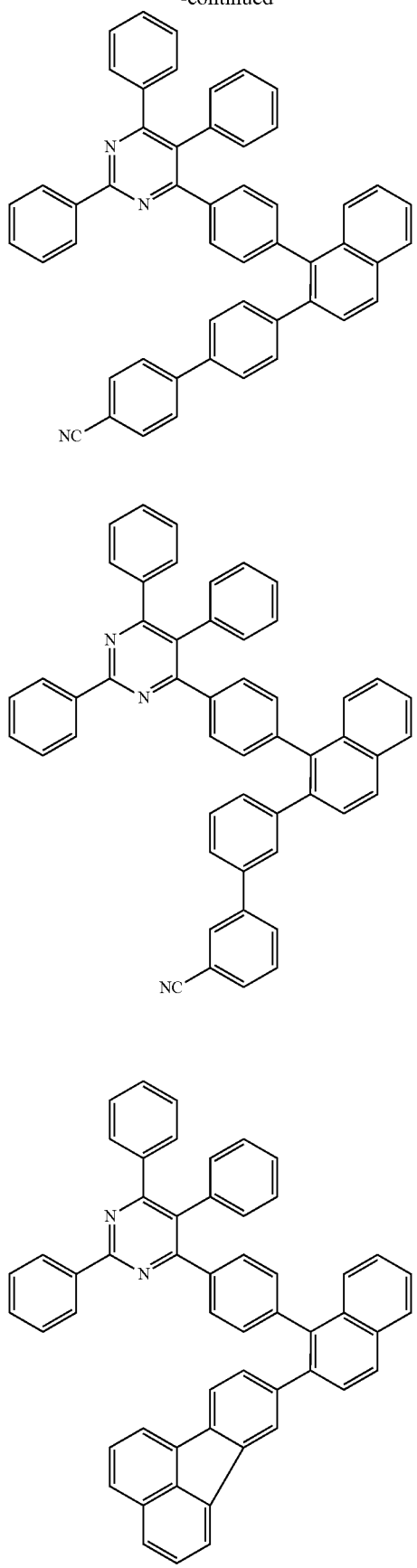
22
-continued
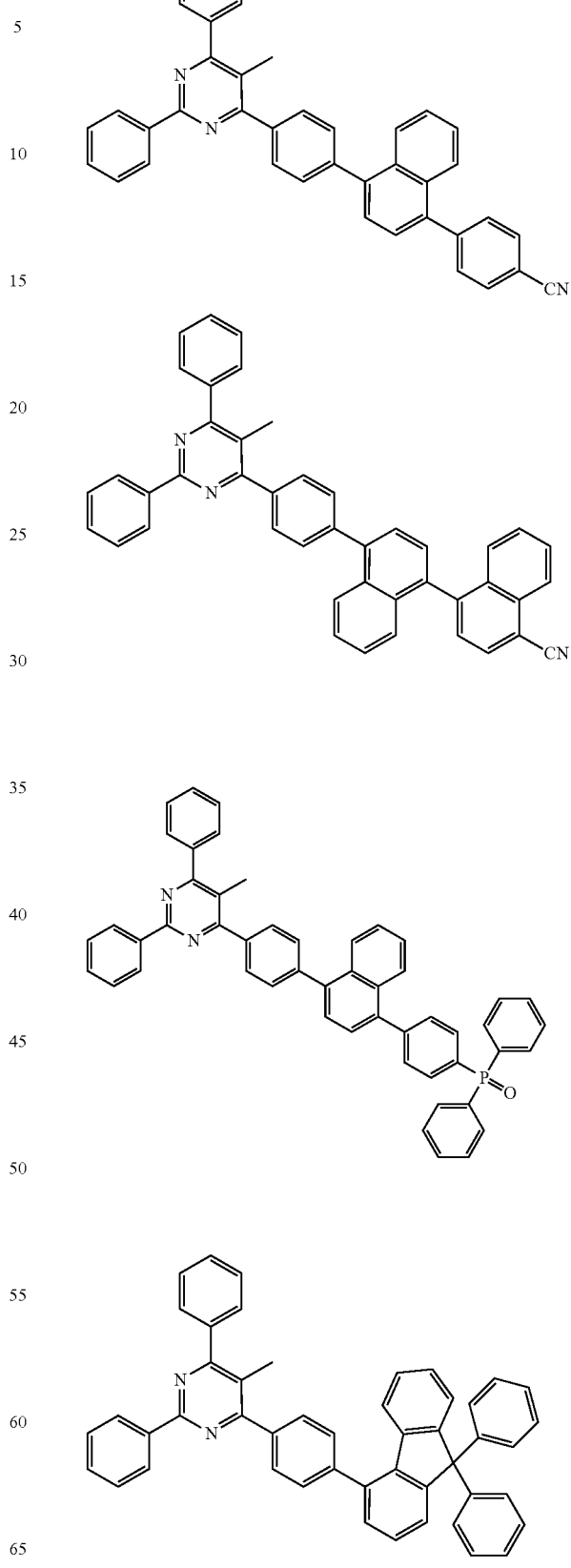

-continued
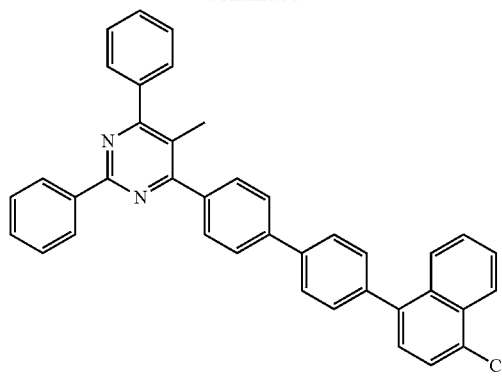
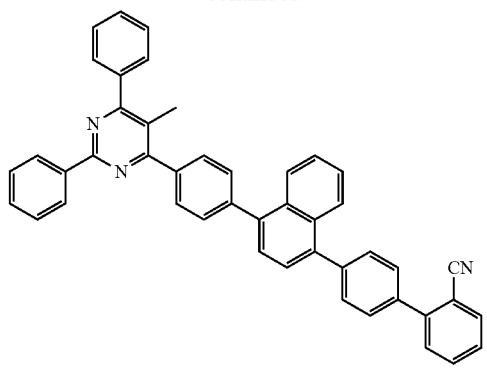
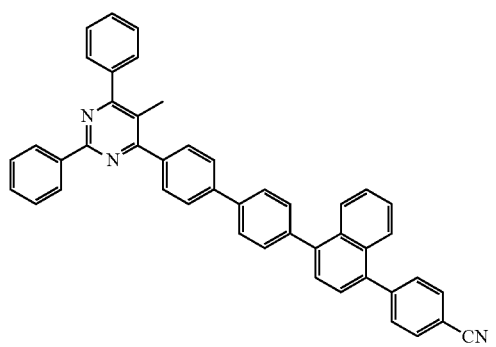
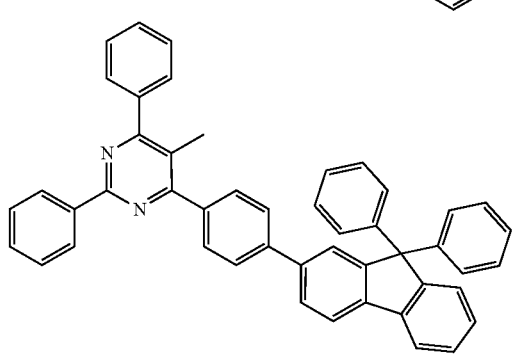
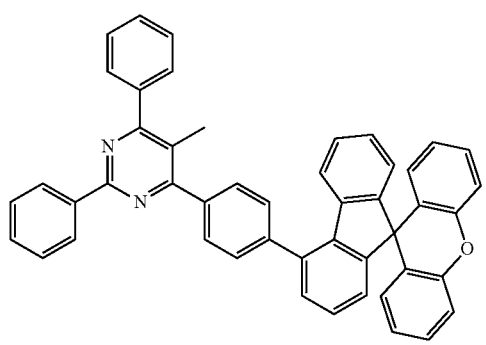
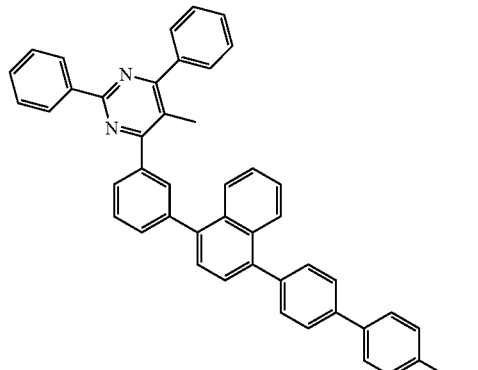
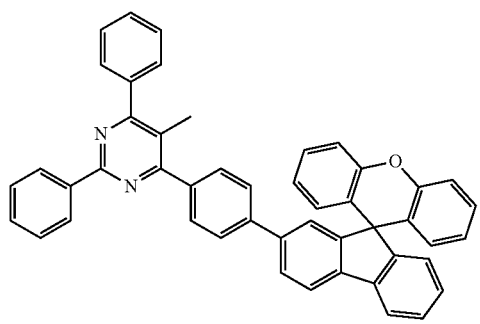
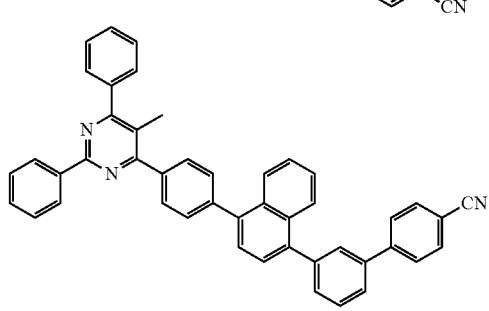
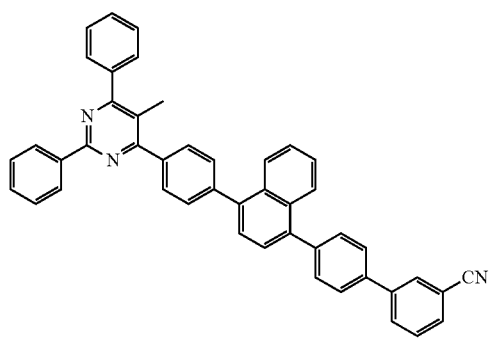
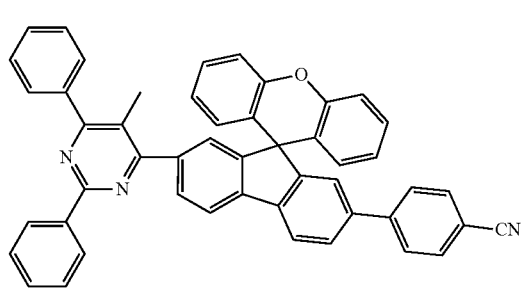

25
-continued
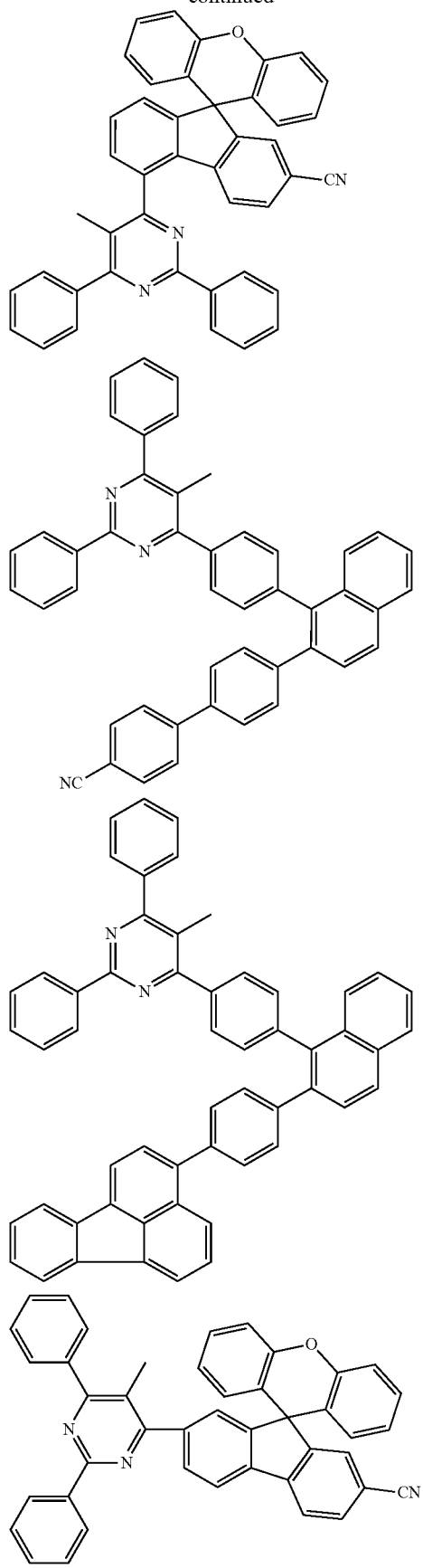
26
-continued
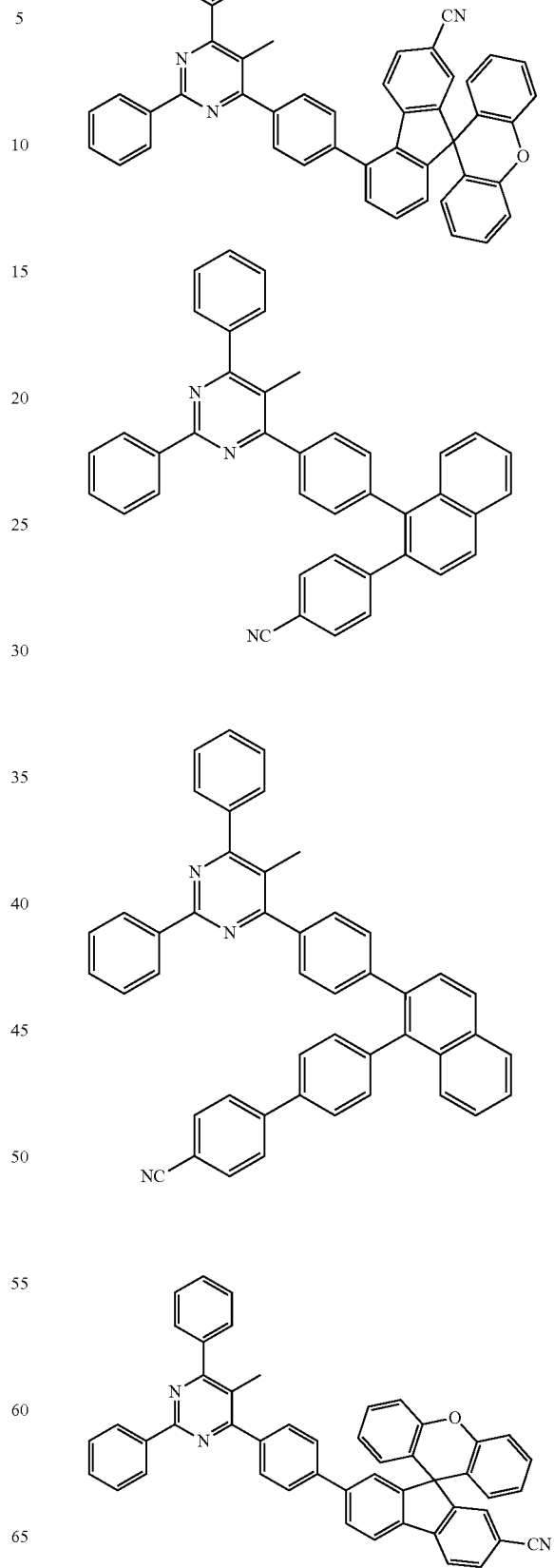

-continued
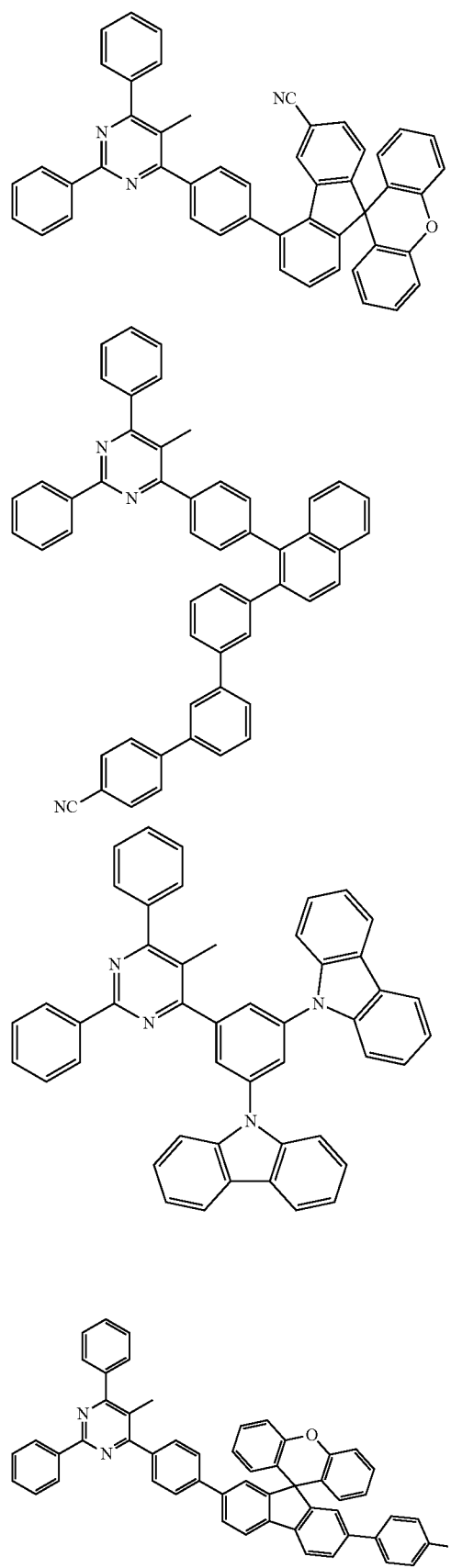
-continued
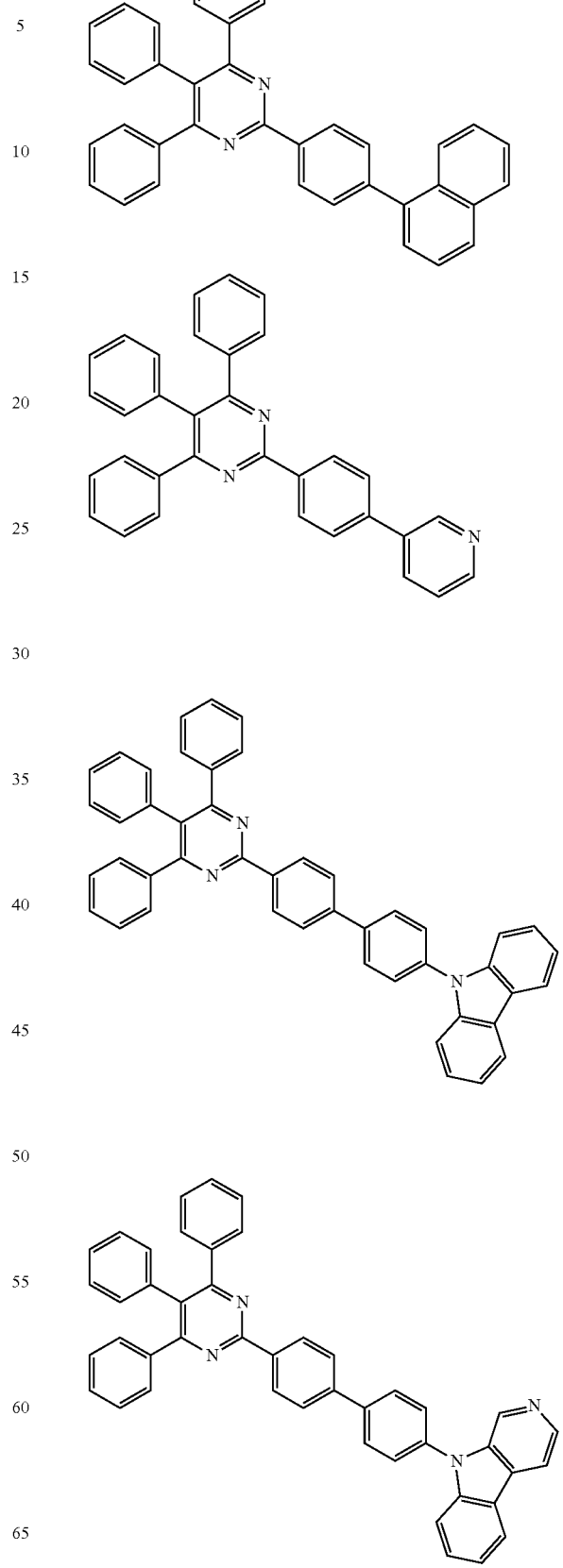

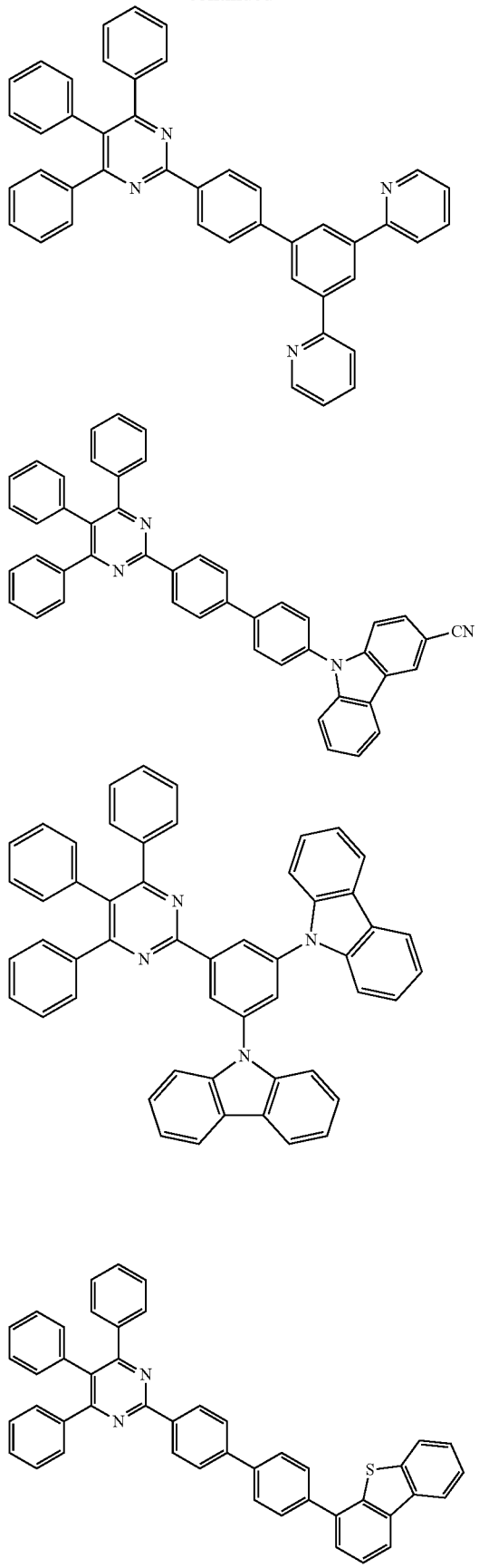
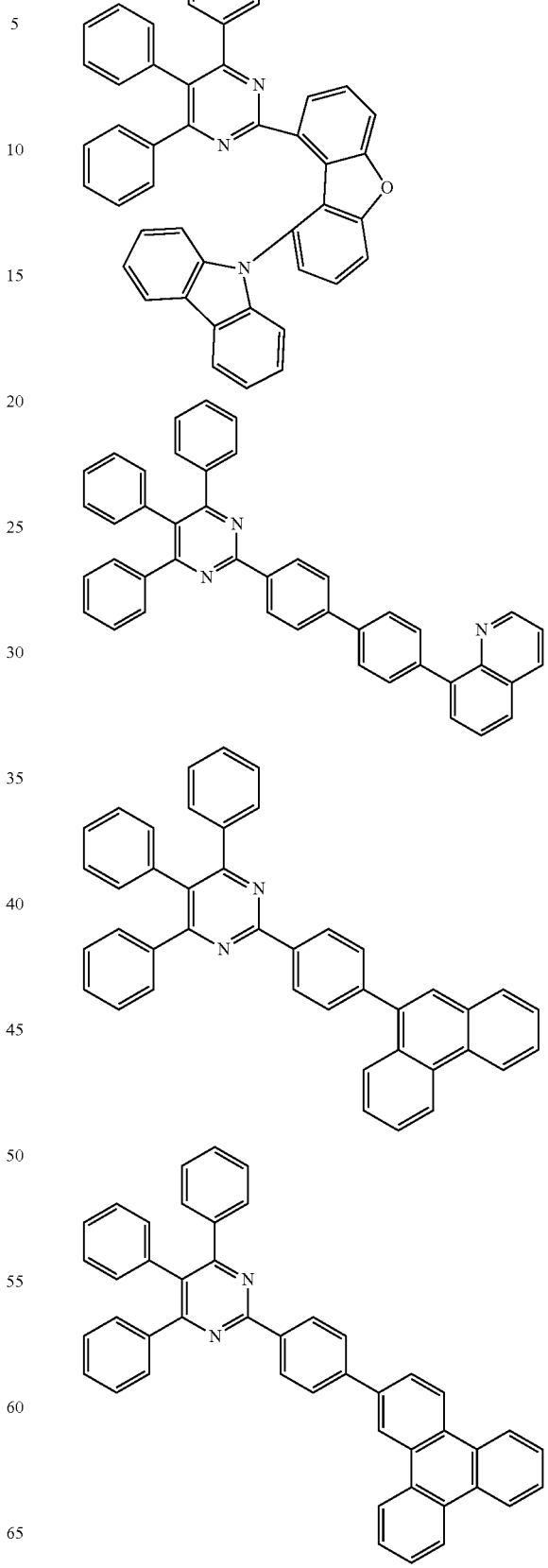

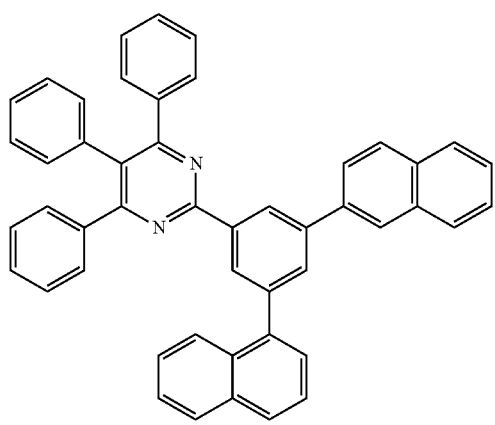
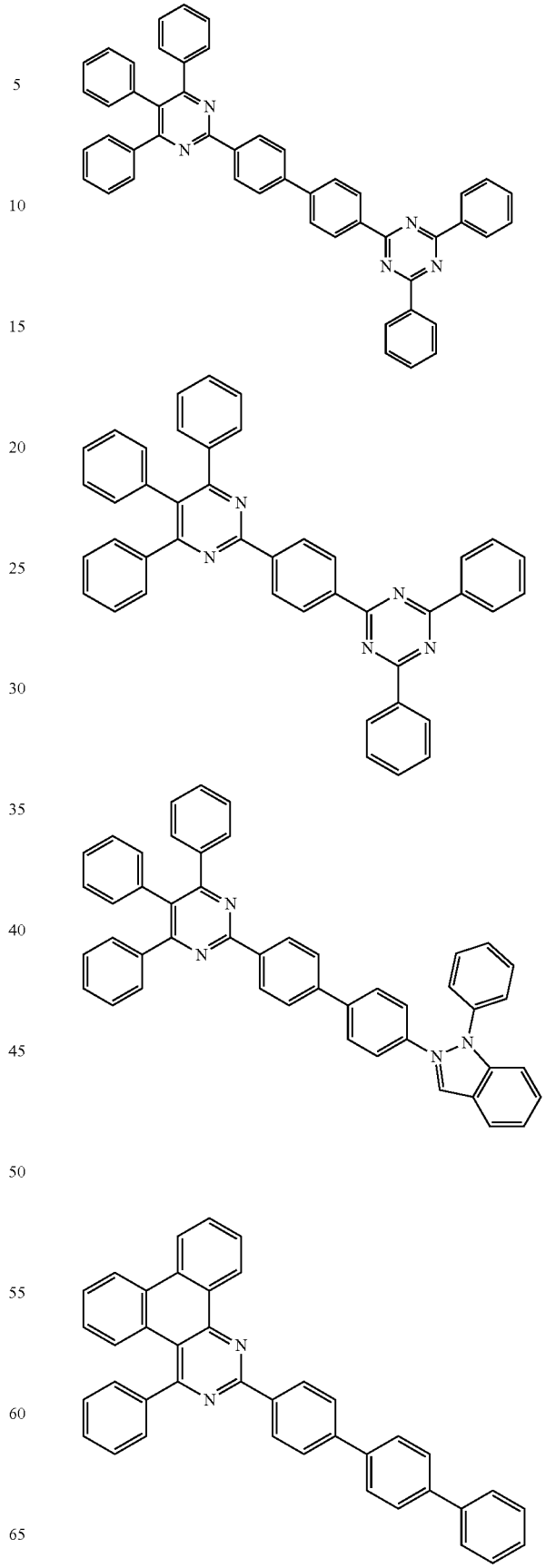

33
-continued
34
-continued
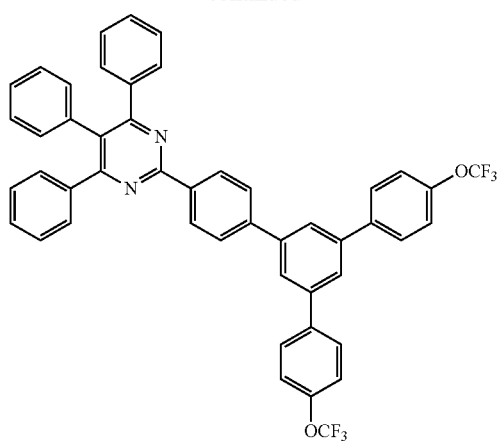
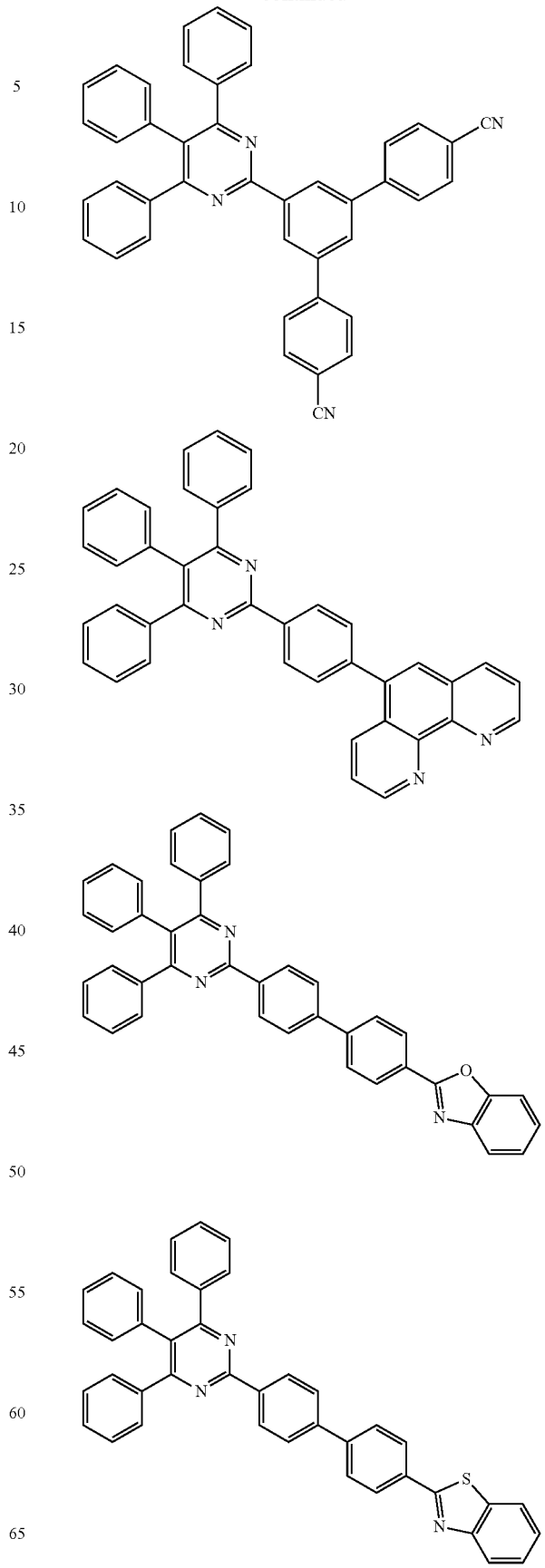

35
-continued
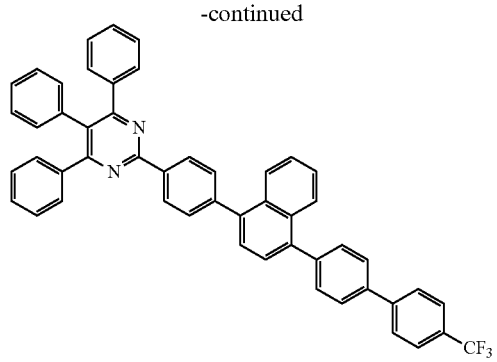
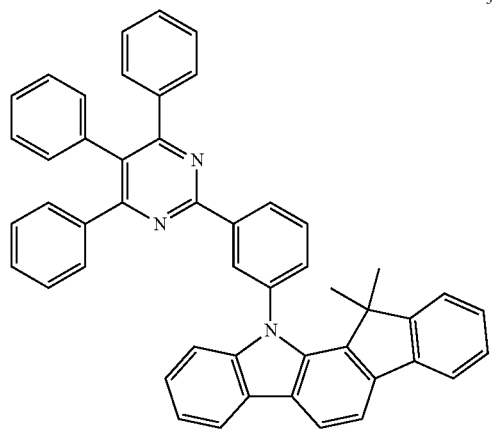
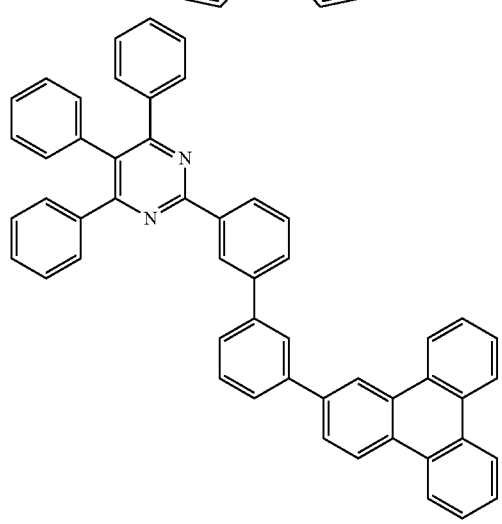
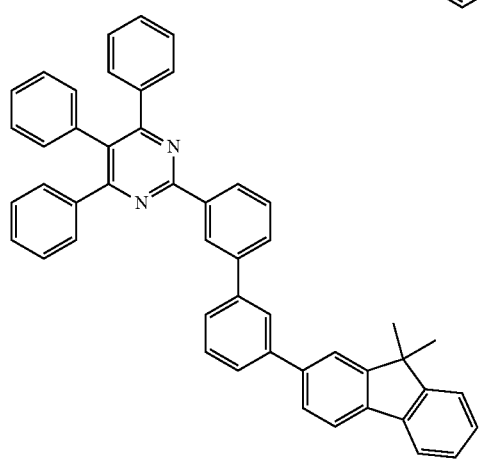
36
-continued
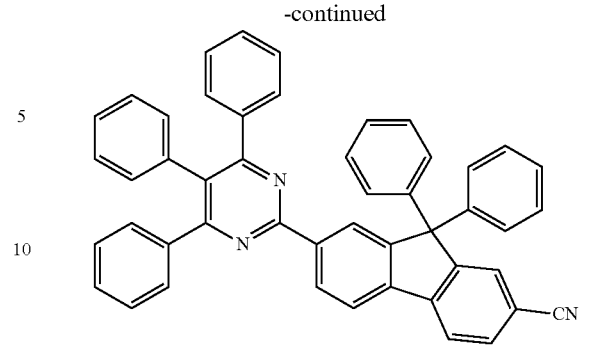
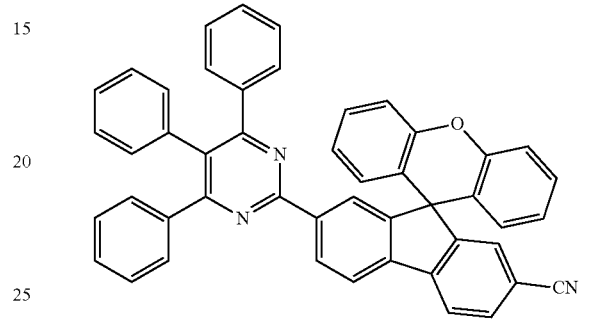
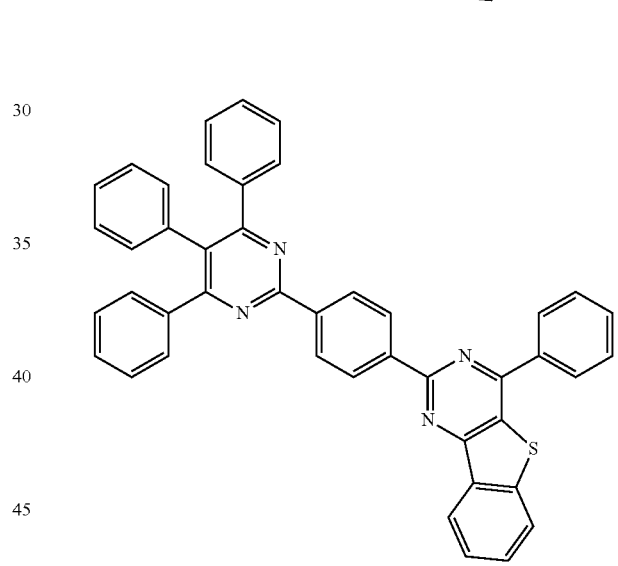
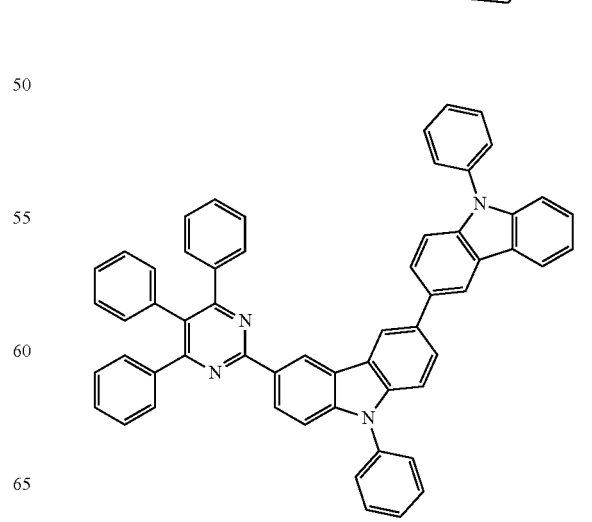

37
-continued
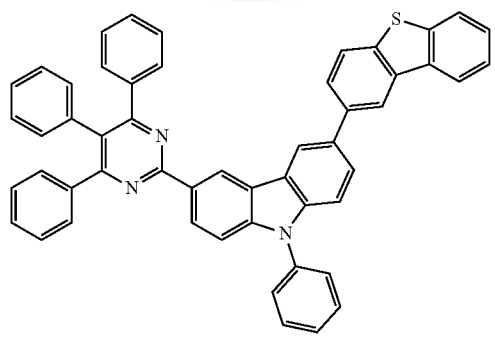
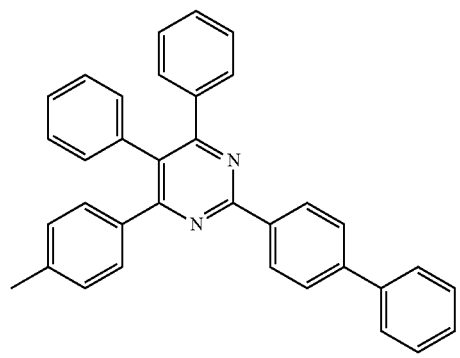
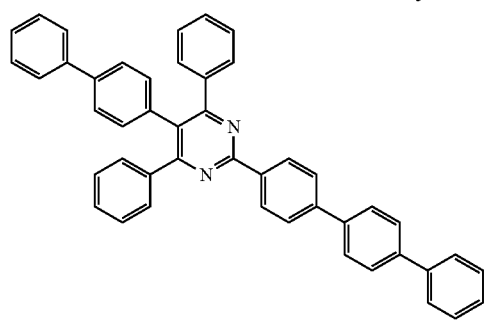
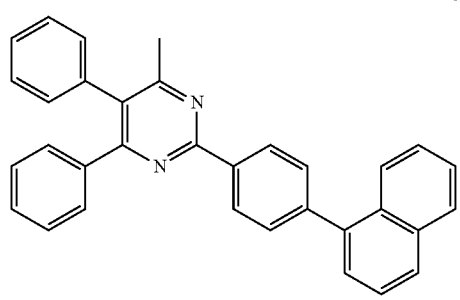
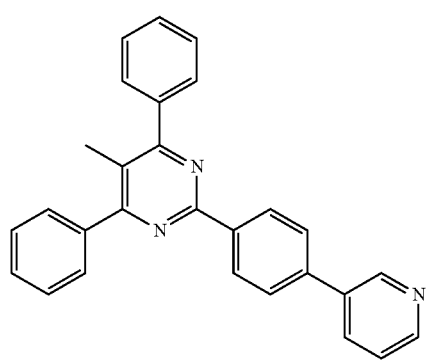
38
-continued
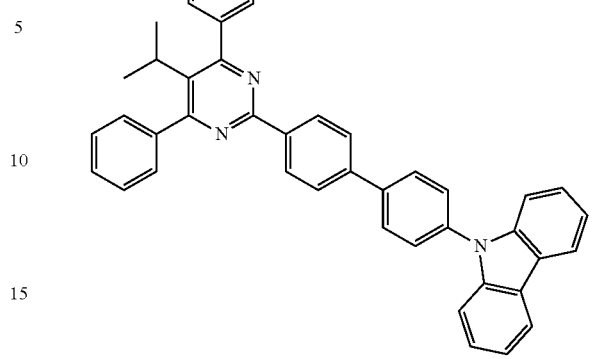
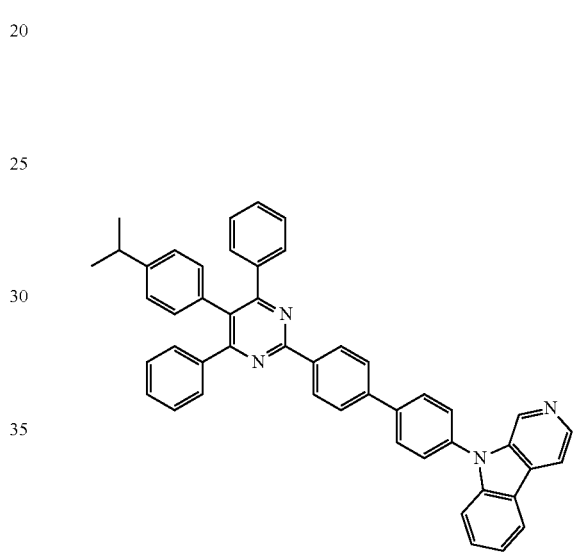
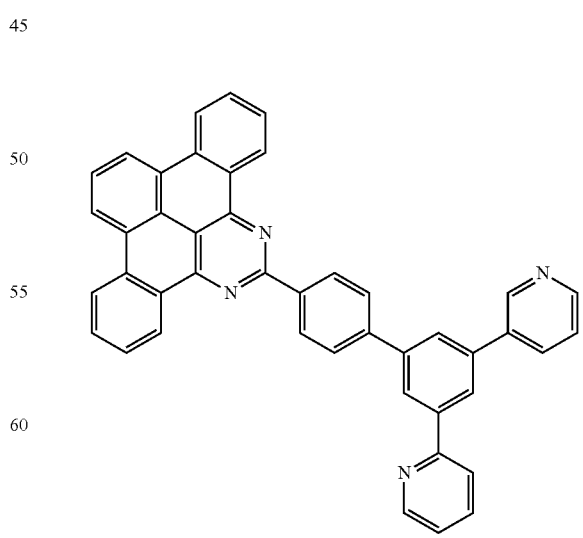

39
-continued
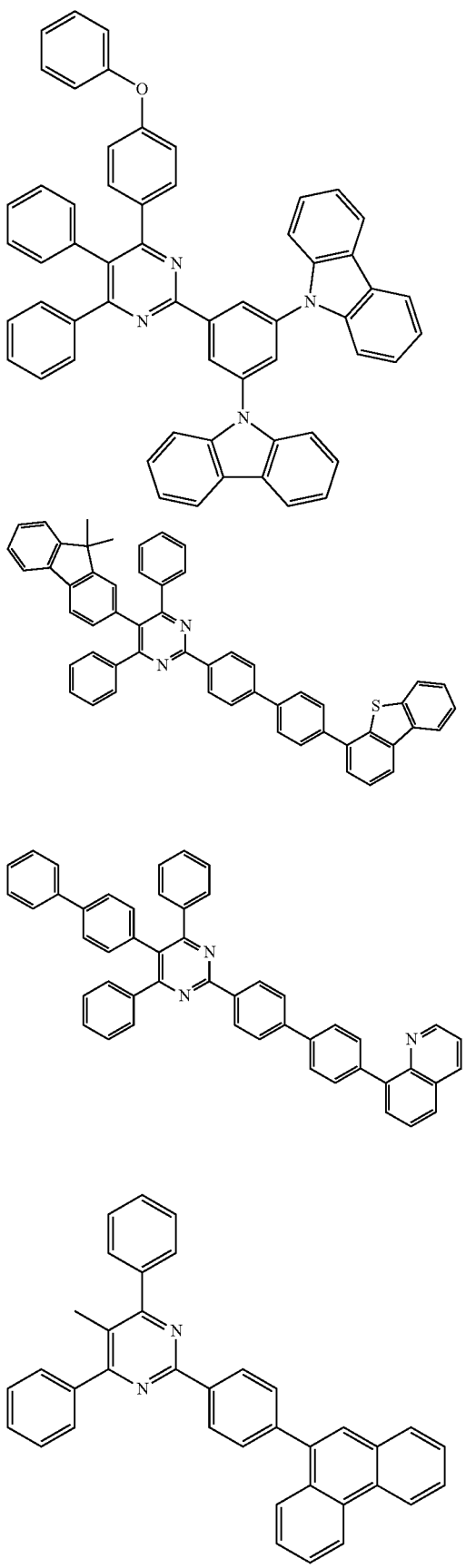
40
-continued
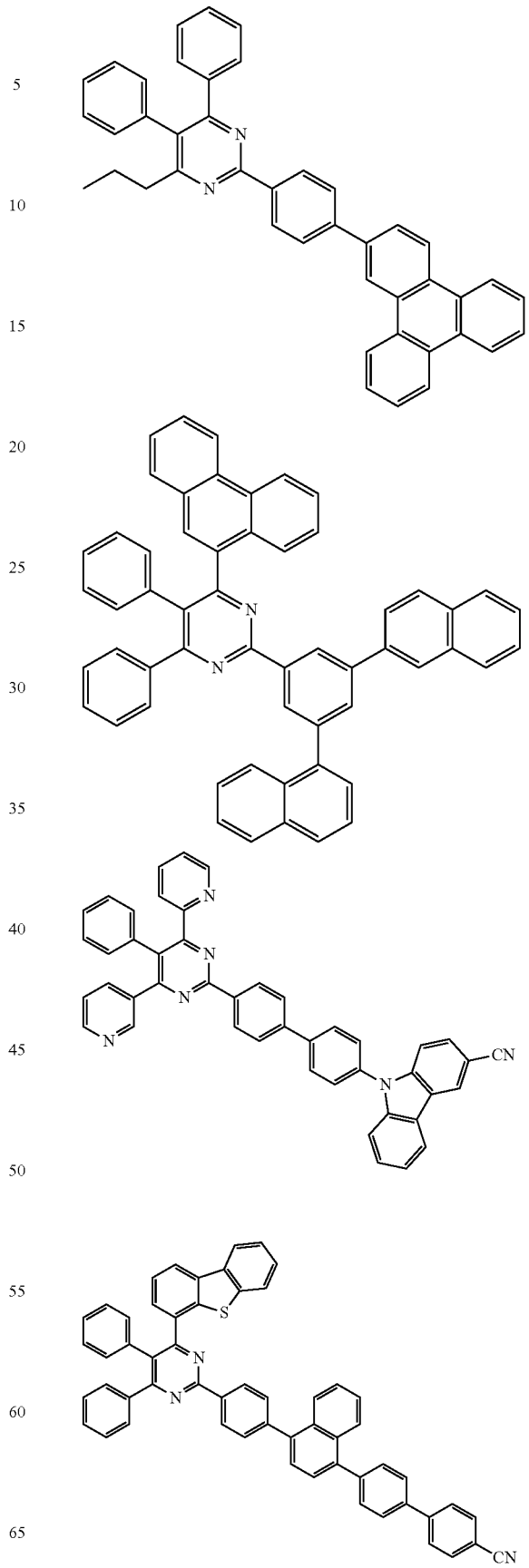

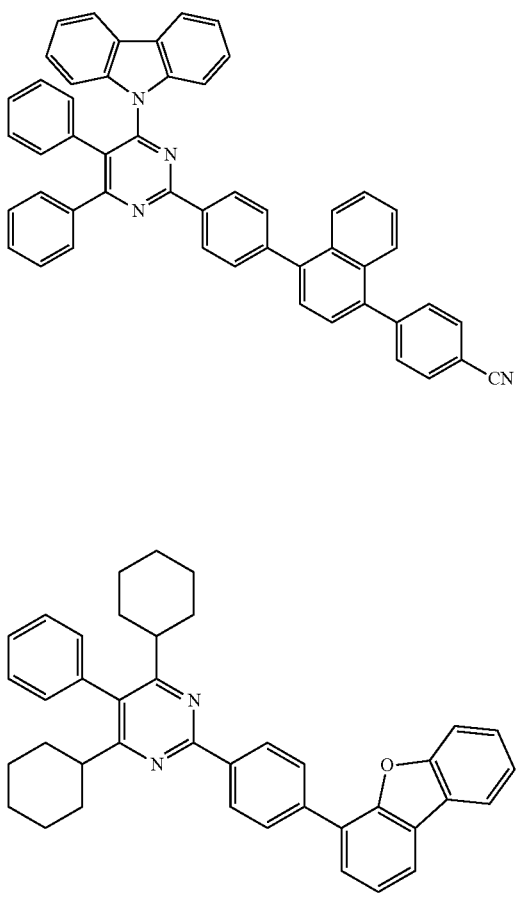
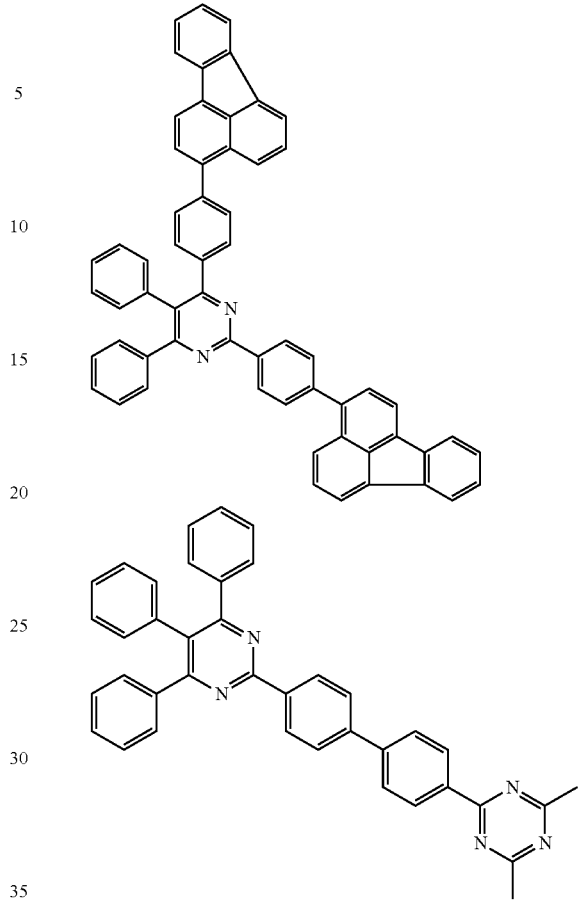
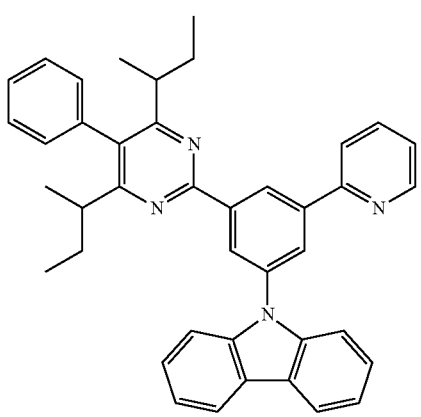
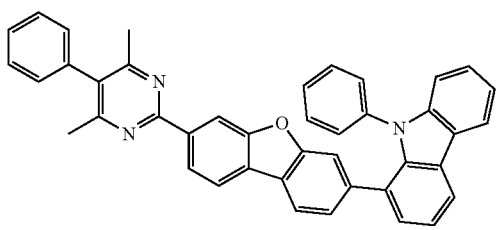

One embodiment of the present specification provides an organic light emitting device comprising the compound described above.

According to one embodiment of the present specification, the organic light emitting device comprises a first electrode; a second electrode provided opposite to the first electrode; and one or more organic material layers provided between the first electrode and the second electrode, wherein the organic material layer comprises the compound of Chemical Formula 1.

The organic material layer of the organic light emitting device of the present specification can be formed in a single layer structure, but can also be formed in a multilayer structure in which two or more organic material layers are laminated. For example, the organic light emitting device of the present disclosure can have a structure comprising a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can comprise a larger number of organic layers.

For example, the organic light emitting device of the present specification can have structures as illustrated in FIG. 1, FIG. 2 and FIG. 8, however, the structure is not limited thereto.

FIG. 1 illustrates a structure of the organic light emitting device in which a substrate (1), an anode (2), a hole injection layer (3), a hole transfer layer (4), a light emitting layer (6), a hole blocking layer (7), an electron injection and transfer layer (8) and a cathode (11) are consecutively laminated. In such a structure, the compound of Chemical Formula 1 can be included in the electron injection and transfer layer (8).

FIG. 2 illustrates a structure of the organic light emitting device in which a substrate (1), an anode (2), a hole injection layer (3), a hole transfer layer (4), an electron blocking layer (5), a light emitting layer (6), an electron injection and transfer layer (8) and a cathode (11) are consecutively laminated. In such a structure, the compound of Chemical Formula 1 can be included in the electron injection and transfer layer (8).

FIG. 8 illustrates a structure of the organic light emitting device in which a substrate (1), an anode (2), a p-doped hole transfer layer (4*p*), a hole transfer layer (4R, 4G, 4B), a light emitting layer (6RP, 6GP, 6BF), a first electron transfer layer (9*a*), a second electron transfer layer (9*b*), an electron injection layer (10), a cathode (11) and a capping layer (14) are consecutively laminated. In such a structure, the compound of Chemical Formula 1 can be included in one or more of the first electron transfer layer (9*a*) and the second electron transfer layer (9*b*).

According to one embodiment of the present specification, the organic light emitting device can have a tandem structure in which two or more independent devices are connected in series. In one embodiment, the tandem structure can have a form in which each organic light emitting device are connected by a charge generating layer. A device having a tandem structure can be driven at a lower current than a unit device based on the same brightness, and therefore, there is an advantage in that device lifetime properties are greatly enhanced.

According to one embodiment of the present specification, the organic material layer comprises a first stack comprising one or more light emitting layers; a second stack comprising one or more light emitting layers; and one or more charge generating layers provided between the first stack and the second stack.

According to another embodiment of the present specification, the organic material layer comprises a first stack comprising one or more light emitting layers; a second stack comprising one or more light emitting layers; and a third stack comprising one or more light emitting layers, and comprises one or more charge generating layers provided between each of the first stack and the second stack; and the second stack and the third stack.

In the present specification, the charge generating layer means a layer in which holes and electrons are generated when applying a voltage. The charge generating layer can be an N-type charge generating layer or a P-type charge generating layer. In the present specification, the N-type charge generating layer means a charge generating layer locating closer to an anode than the P-type charge generating layer, and the P-type charge generating layer means a charge generating layer locating closer to a cathode than the N-type charge generating layer.

The N-type charge generating layer and the P-type charge generating layer can be provided in contact with each other, and in this case, an NP junction is formed. By the NP junction, holes are readily formed in the P-type charge generating layer, and electrons are readily formed in the N-type charge generating layer. The electrons are transferred toward an anode through a LUMO level of the N-type charge generating layer, and the holes are transferred toward a cathode through a HOMO level of the P-type organic material layer.

The first stack, the second stack and the third stack each comprise one or more light emitting layers, and can further comprise one or more of a hole injection layer, a hole transfer layer, an electron blocking layer, an electron injection layer, an electron transfer layer, a hole blocking layer, a layer carrying out hole transfer and hole injection at the same time (hole injection and transfer layer), and a layer carrying out electron transfer and electron injection at the same time (electron injection and transfer layer).

The organic light emitting device comprising the first stack and the second stack is illustrated in FIG. 3.

FIG. 3 illustrates a structure of the organic light emitting device in which a substrate (1), an anode (2), a hole injection layer (3), a first hole transfer layer (4*a*), an electron blocking layer (5), a first light emitting layer (6*a*), a first electron transfer layer (9*a*), an N-type charge generating layer (12), a P-type charge generating layer (13), a second hole transfer layer (4*b*), a second light emitting layer (6*b*), an electron injection and transfer layer (8) and a cathode (11) are consecutively laminated. In such a structure, the compound of Chemical Formula 1 can be included in the electron injection and transfer layer (8).

The organic light emitting device including the first stack to the third stack is illustrated in FIGS. 4 to 7.

FIG. 4 illustrates a structure of the organic light emitting device in which a substrate (1), an anode (2), a hole injection layer (3), a first hole transfer layer (4*a*), an electron blocking layer (5), a first light emitting layer (6*a*), a first electron transfer layer (9*a*), a first N-type charge generating layer (12*a*), a first P-type charge generating layer (13*a*), a second hole transfer layer (4*b*), a second light emitting layer (6*b*), a second electron transfer layer (9*b*), a second N-type charge generating layer (12*b*), a second P-type charge generating layer (13*b*), a third hole transfer layer (4*c*), a third light emitting layer (6*c*), a third electron transfer layer (9*c*) and a cathode (11) are consecutively laminated. In such a structure, the compound of Chemical Formula 1 can be included in one or more of the first electron transfer layer (9*a*), the second electron transfer layer (9*b*) and the third electron transfer layer (9*c*).

FIG. 5 illustrates a structure of the organic light emitting device in which a substrate (1), an anode (2), a hole injection layer (3), a first hole transfer layer (4*a*), a second hole transfer layer (4*b*), a first blue fluorescent light emitting layer (6BFa), a first electron transfer layer (9*a*), a first N-type charge generating layer (12*a*), a first P-type charge generating layer (13*a*), a third hole transfer layer (4*c*), a red phosphorescent light emitting layer (6RP), a yellow green phosphorescent light emitting layer (6YGP), a green phosphorescent light emitting layer (6GP), a second electron transfer layer (9*b*), a second N-type charge generating layer (12*b*), a second P-type charge generating layer (13*b*), a fourth hole transfer layer (4*d*), a fifth hole transfer layer (4*e*), a second blue fluorescent light emitting layer (6BFb), a third electron transfer layer (9*c*), an electron injection layer (10), a cathode (11) and a capping layer (14) are consecutively laminated. In such a structure, the compound of Chemical Formula 1 can be included in one or more of the third electron transfer layer (9*c*), the second electron transfer layer (9*b*) and the first electron transfer layer (9*a*).

FIG. 6 illustrates a structure of the organic light emitting device in which a substrate (1), an anode (2), a hole injection layer (3), a first hole transfer layer (4*a*), a second hole transfer layer (4*b*), a first blue fluorescent light emitting layer (6BFa), a first electron transfer layer (9*a*), a first N-type charge generating layer (12*a*), a first P-type charge generating layer (13*a*), a third hole transfer layer (4*c*), a red phosphorescent light emitting layer (6RP), a green phosphorescent light emitting layer (6GP), a second electron transfer layer (9*b*), a second N-type charge generating layer (12*b*), a second P-type charge generating layer (13*b*), a fourth hole transfer layer (4*d*), a fifth hole transfer layer (4*e*), a second blue fluorescent light emitting layer (6BFb), a third electron transfer layer (9*c*), an electron injection layer (10), a cathode (11) and a capping layer (14) are consecutively laminated. In such a structure, the compound of Chemical Formula 1 can be included in one or more of the third electron transfer layer (9*c*), the second electron transfer layer (9*b*) and the first electron transfer layer (9*a*).

FIG. 7 illustrates a structure of the organic light emitting device in which a substrate (1), an anode (2), a first p-doped hole transfer layer (4*pa*), a first hole transfer layer (4*a*), a second hole transfer layer (4*b*), a first blue fluorescent light emitting layer (6BFa), a first electron transfer layer (9*a*), a first N-type charge generating layer (12*a*), a first P-type charge generating layer (13*a*), a third hole transfer layer (4*c*), a fourth hole transfer layer (4*d*), a second blue fluorescent light emitting layer (6BFb), a second electron transfer layer (9*b*), a second N-type charge generating layer (12*b*), a second P-type charge generating layer (13*b*), a fifth hole transfer layer (4*e*), a sixth hole transfer layer (4*f*), a third blue fluorescent light emitting layer (6BFc), a third electron transfer layer (9*c*), an electron injection layer (10), a cathode (11) and a capping layer (14) are consecutively laminated. In such a structure, the compound of Chemical Formula 1 can be included in one or more of the first electron transfer layer (9*a*), the second electron transfer layer (9*b*), and the third electron transfer layer (9*c*).

The N-type charge generating layer can be 2,3,5,6-tetrafluoro-7,7,8,8-tetracyanoquinodimethane (F4TCNQ), fluorine-substituted 3,4,9,10-perylenetetracarboxylic dianhydride (PTCDA), cyano-substituted PTCDA, naphthalenete-tracarboxylic dianhydride (NTCDA), fluorine-substituted NTCDA, cyano-substituted NTCDA, a hexaazatriphenylene derivative and the like, but is not limited thereto. In one embodiment, the N-type charge generating layer can include both a benzimidazophenanthridine-based derivative and a Li metal.

The P-type charge generating layer can include both an arylamine-based derivative and a compound including a cyano group.

The organic light emitting device of the present specification can be manufactured using common organic light emitting device manufacturing methods and materials except that one or more organic material layers are formed using the compound of Chemical Formula 1 described above.

When manufacturing an organic light emitting device formed with an organic material layer including the compound of Chemical Formula 1, the compound of Chemical Formula 1 can be formed into the organic material layer using a solution coating method as well as a vacuum deposition method. Herein, the solution coating method means spin coating, dip coating, inkjet printing, screen printing, a spray method, roll coating and the like, but is not limited thereto.

The organic material layer of the organic light emitting device of the present specification can be formed in a single layer structure, but can also be formed in a multilayer structure in which two or more organic material layers are laminated. For example, the organic light emitting device of the present disclosure can have a structure including one or more of a hole transfer layer, a hole injection layer, an electron blocking layer, a layer carrying out hole transfer and hole injection at the same time, an electron transfer layer, an electron injection layer, a hole blocking layer, and a layer carrying out electron transfer and electron injection at the same time. However, the structure of the organic light emitting device of the present specification is not limited thereto, and can include a smaller or a larger number of organic material layers.

According to one embodiment of the present specification, the organic material layer comprises a light emitting layer, the light emitting layer comprises a host and a dopant, and the dopant has a maximum light emission wavelength of 400 nm to 520 nm.

According to another embodiment, the dopant of the light emitting layer is a blue fluorescent dopant.

According to one embodiment of the present specification, the organic material layer comprises two or more light emitting layers, and at least one of the two or more light emitting layers comprises a blue fluorescent dopant.

According to another embodiment, at least two of the two or more light emitting layers have a different maximum light emission wavelength.

In another embodiment, at least one of the two or more light emitting layers comprises a phosphorescent dopant, and at least one of the remaining layers comprises a fluorescent dopant.

When the organic light emitting device comprises two or more light emitting layers, each of the light emitting layers can be vertically laminated as illustrated in FIGS. 4 to 7, or each of the light emitting layers can be horizontally laminated as illustrated in FIG. 8.

In the organic light emitting device of the present specification, the organic material layer comprises a hole transfer layer, a hole injection layer, or a layer carrying out hole transfer and hole injection at the same time, and the hole transfer layer, the hole injection layer, or the layer carrying out hole transfer and hole injection at the same time can comprise the compound of Chemical Formula 1 described above.

In another organic light emitting device of the present specification, the organic material layer comprises an electron transfer layer, an electron injection layer, or a layer carrying out electron transfer and electron injection at the same time, and the electron transfer layer, the electron injection layer, or the layer carrying out electron transfer and electron injection at the same time can include the compound of Chemical Formula 1 described above.

According to another embodiment, the electron transfer layer, the electron injection layer, or the layer carrying out electron transfer and electron injection at the same time comprises the compound of Chemical Formula 1, and the light emitting layer can comprise a blue fluorescent dopant.

In another organic light emitting device of the present specification, the organic material layer comprises a light emitting layer, and the light emitting layer can comprise the compound of Chemical Formula 1 described above.

According to another embodiment, the organic material layer comprises a light emitting layer, and the light emitting layer can comprise the compound of Chemical Formula 1 as a host of the light emitting layer.

According to another embodiment, the organic material layer comprises a light emitting layer, and the light emitting layer can comprise the compound of Chemical Formula 1 as a dopant.

In one embodiment of the present specification, the organic material layer comprises a light emitting layer, and the light emitting layer comprises a host and a dopant. Herein, the dopant can be included in 1 parts by weight to 20 parts by weight, and preferably in 1 parts by weight to 10 parts by weight based on 100 parts by weight of the host.

In one embodiment of the present specification, the first electrode is an anode, and the second electrode is a cathode.

According to another embodiment, the first electrode is a cathode, and the second electrode is an anode.

According to one embodiment of the present specification, the organic material layer comprises a hole blocking layer, and the hole blocking layer comprises the compound of Chemical Formula 1.

According to one embodiment of the present specification, the organic material layer further comprises, in addition to the organic material layer comprising the compound of Chemical Formula 1, a hole injection layer or a hole transfer layer comprising a compound comprising an arylamino group, a carbazolyl group or a benzocarbazolyl group.

The organic light emitting device of the present specification can be manufactured using materials and methods known in the art, except that one or more layers of the organic material layers comprise the compound of the present specification, that is, the compound of Chemical Formula 1.

When the organic light emitting device comprises a plurality of organic material layers, the organic material layers can be formed with the same material or with different materials.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as a sputtering method or an e-beam evaporation method, forming an organic material layer comprising a hole injection layer, a hole transfer layer, a light emitting layer and an electron transfer layer thereon, and then depositing a material usable as a second electrode thereon. In addition to such a method, the organic light emitting device can be manufactured by consecutively depositing a cathode material, an organic material layer and a first electrode material on a substrate. In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such methods, the organic light emitting device can also be manufactured by consecutively depositing a cathode material, an organic material layer and an anode material on a substrate. However, the manufacturing method is not limited thereto.

As the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

In one embodiment of the present specification, the p-doped hole transfer layer means a hole transfer layer including a p-type dopant.

The light emitting material of the light emitting layer is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

In one embodiment of the present specification, an anthracene derivative unsubstituted or substituted with deuterium can be used as a host of the light emitting layer. In one embodiment, a lifetime is enhanced when an anthracene derivative is deuterated, which has an advantage of being usable as a host material in more diverse device structures.

According to one embodiment of the present specification, the host can be a compound of the following Chemical Formula H1 or H2, but is not limited thereto. When including the following compound, an energy level between the organic material layer and the light emitting layer is properly controlled, and quantities of electrons migrating from the organic material layer to the light emitting layer are readily controlled, which is effective in improving a lifetime of an organic light emitting device:

Chemical Formula H1

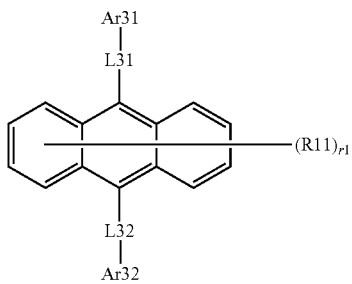

Chemical Formula H2

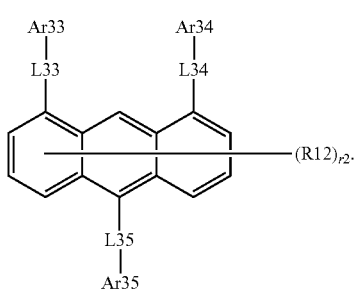

In Chemical Formulae H1 and H2:

L31 to L35 are the same as or different from each other, and each independently is a direct bond, a substituted or unsubstituted arylene group, or a substituted or unsubstituted heteroarylene group;

Ar31 to Ar35 are the same as or different from each other, and each independently is a substituted or unsubstituted aryl group, or a substituted or unsubstituted heteroaryl group;

R11 and R12 are the same as or different from each other, and each independently is hydrogen, or a substituted or unsubstituted aryl group;

r1 is an integer of 1 to 8;

r2 is an integer of 1 to 7;

when r1 is 2 or greater, the R11s are the same as or different from each other; and when r2 is 2 or greater, the R12s are the same as or different from each other.

According to one embodiment of the present specification, L31 to L35 are the same as or different from each other, and each independently is a direct bond, or an arylene group.

According to one embodiment of the present specification, L31 to L35 are the same as or different from each other, and each independently is a direct bond, or a $C_{6-22}$ arylene group.

According to one embodiment of the present specification, L31 to L35 are the same as or different from each other, and each independently is a direct bond, or a $C_{6-18}$ arylene group.

According to one embodiment of the present specification, L31 to L35 are the same as or different from each other, and each independently is a direct bond, or a $C_{6-14}$ arylene group.

According to one embodiment of the present specification, L31 to L35 are the same as or different from each other, and each independently is a direct bond, a phenylene group, a divalent naphthyl group, or a divalent anthracenyl group.

According to one embodiment of the present specification, Ar31 to Ar35 are the same as or different from each other, and each independently is an aryl group that is unsubstituted or substituted with deuterium; or a heteroaryl group that is unsubstituted or substituted with an aryl group.

According to one embodiment of the present specification, Ar31 to Ar35 are the same as or different from each other, and each independently is a $C_{6-22}$ aryl group that is unsubstituted or substituted with deuterium; or a $C_{2-24}$ heteroaryl group.

According to one embodiment of the present specification, Ar31 to Ar35 are the same as or different from each other, and each independently is a $C_{6-18}$ aryl group that is unsubstituted or substituted with deuterium; or a $C_{2-20}$ heteroaryl group.

According to one embodiment of the present specification, Ar31 to Ar35 are the same as or different from each other, and each independently is a $C_{6-14}$ aryl group that is unsubstituted or substituted with deuterium; or a $C_{2-16}$ heteroaryl group.

According to one embodiment of the present specification, Ar31 to Ar35 are the same as or different from each other, and each independently is a phenyl group that is unsubstituted or substituted with deuterium; a biphenyl group; a naphthyl group; a phenanthrenyl group; a thiophenyl group that is unsubstituted or substituted with a phenyl group; a dibenzofuranyl group; a dibenzothiophenyl group; a benzo[b]naphtho[1,2-d]furanyl group; a benzo[b]naphtho[2,3-d]furanyl group; a benzo[d]naphtho[1,2-b]furanyl group; a benzo[b]naphtho[2,1-d]thiophenyl group; a benzo[b]naphtho-[1,2-d]thiophenyl group; or a benzo[b]naphtho[2,3-d]thiophenyl group.

According to one embodiment of the present specification, R11 is hydrogen; or an aryl group that is unsubstituted or substituted with an aryl group.

According to one embodiment of the present specification, R11 is hydrogen; or a $C_{6-16}$ aryl group that is unsubstituted or substituted with a $C_{6-16}$ aryl group.

According to one embodiment of the present specification, R11 is hydrogen; or a $C_{6-12}$ aryl group that is unsubstituted or substituted with a $C_{6-12}$ aryl group.

According to one embodiment of the present specification, R11 is hydrogen; or a naphthyl group that is unsubstituted or substituted with a phenyl group.

According to one embodiment of the present specification, R12 is hydrogen.

According to one embodiment of the present specification, the host is any one or more selected from among the following compounds:

-continued
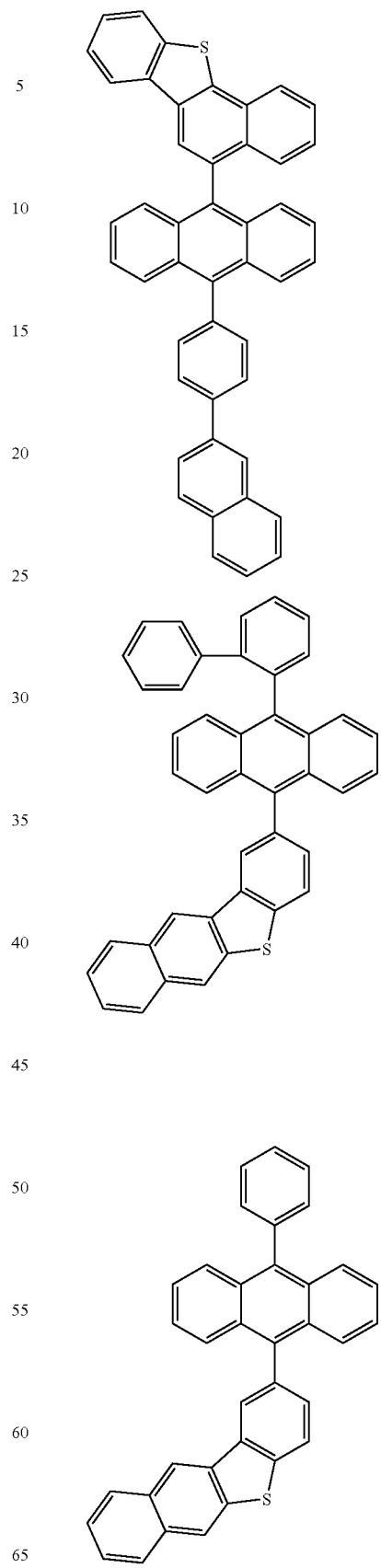

-continued
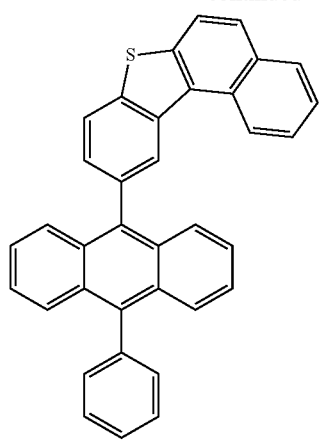
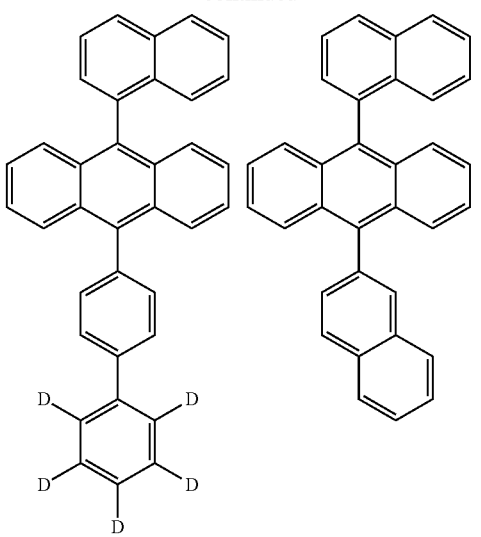
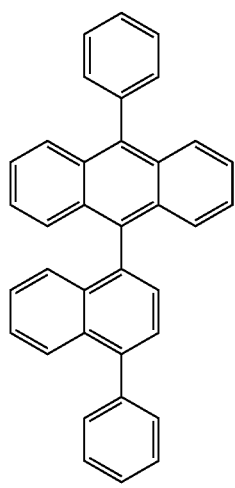
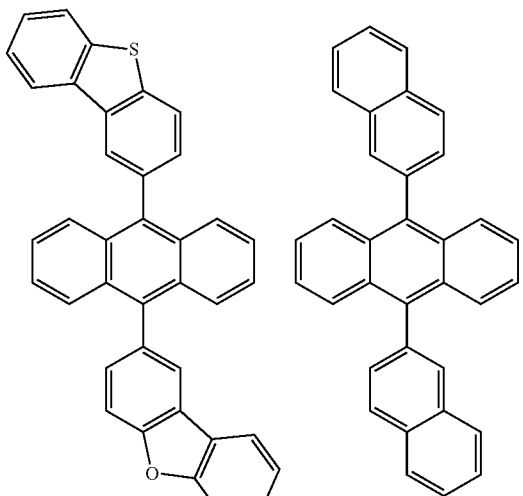
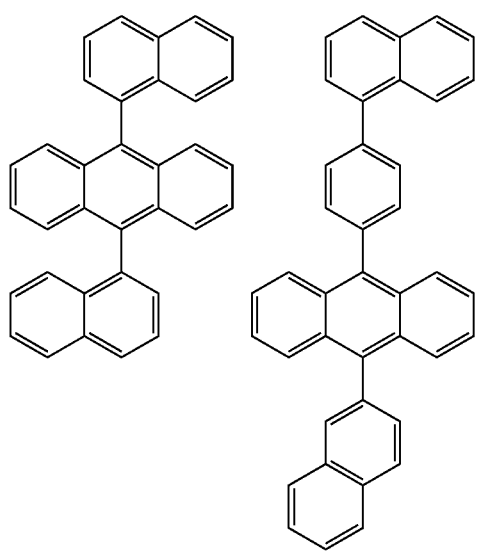
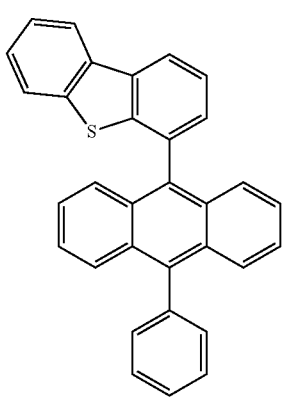 [SMILES: c1ccc(-c2c3ccccc3c(-c3cccc4c3sc3ccccc34)c3ccccc23)cc1]

-continued
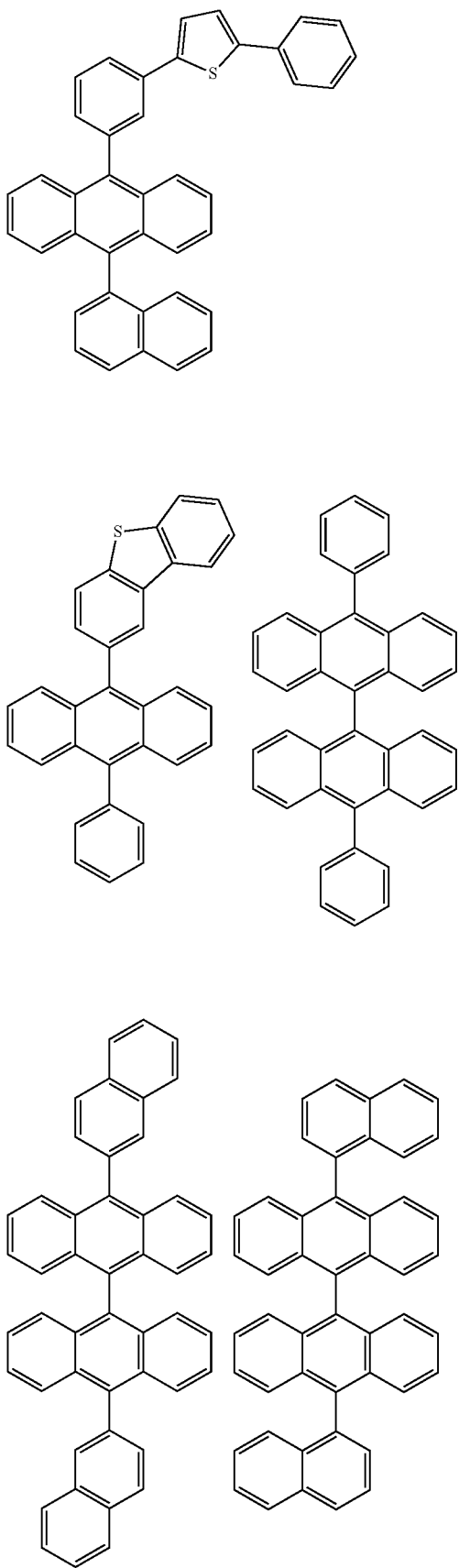
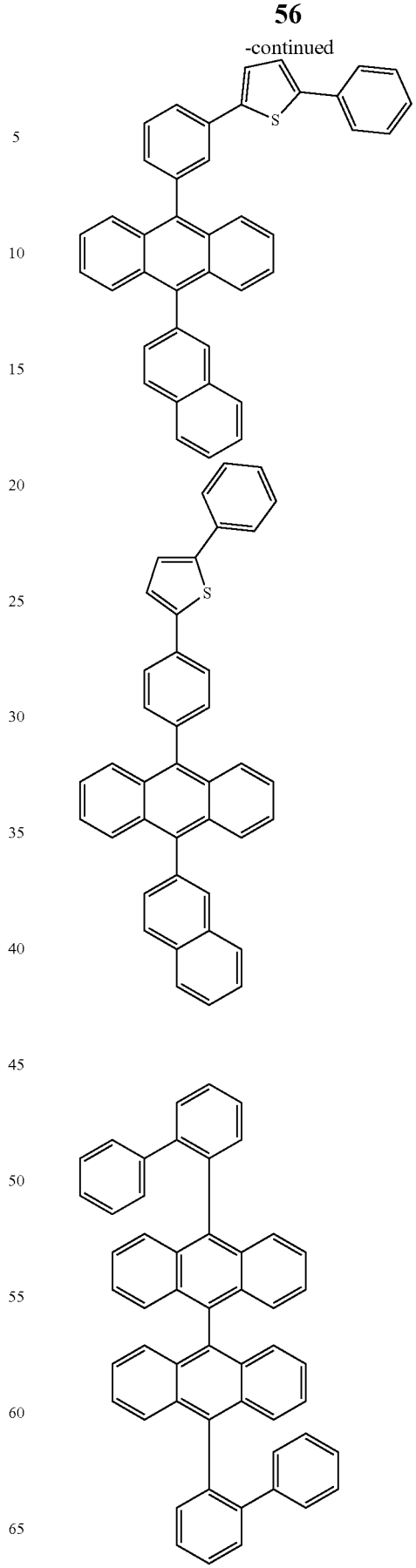

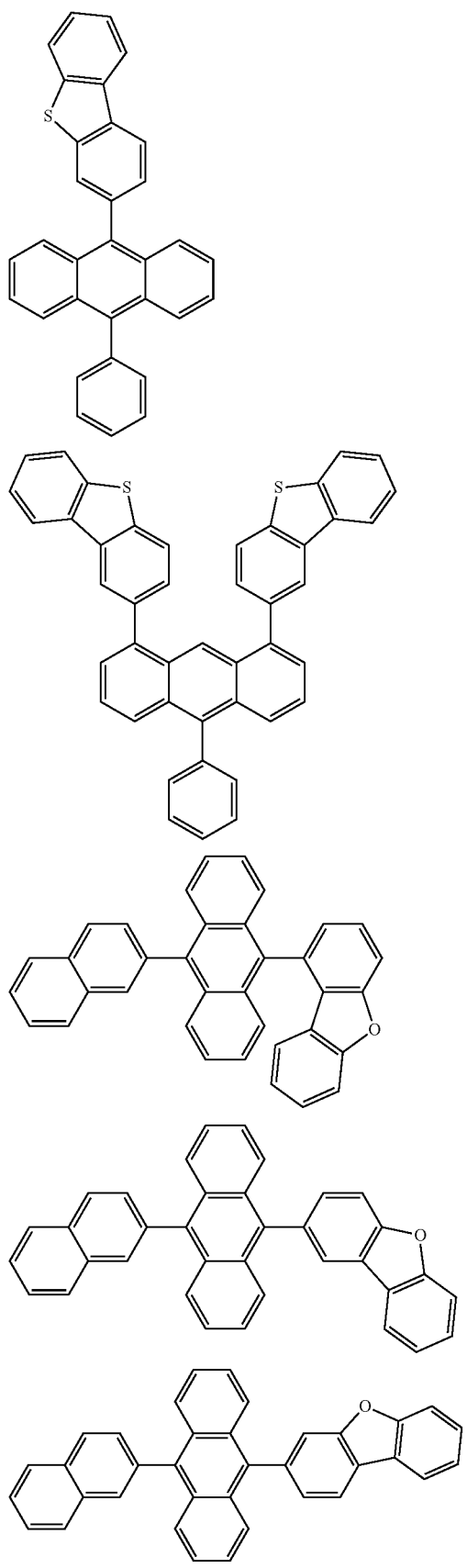
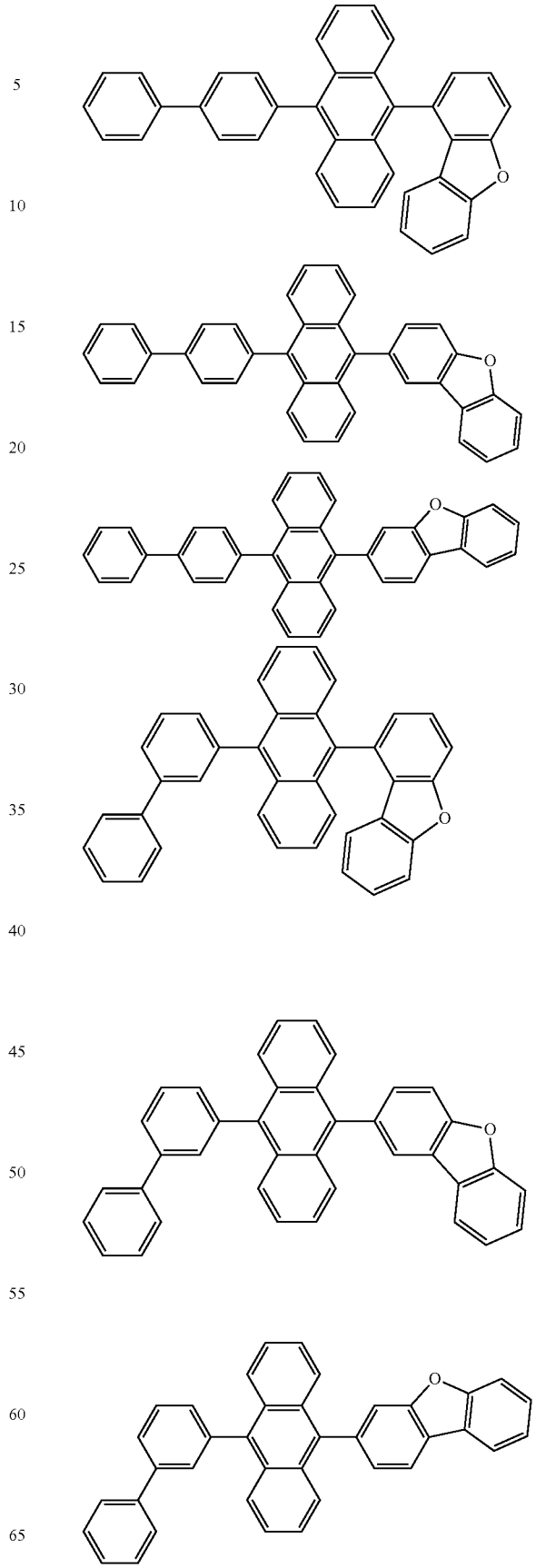

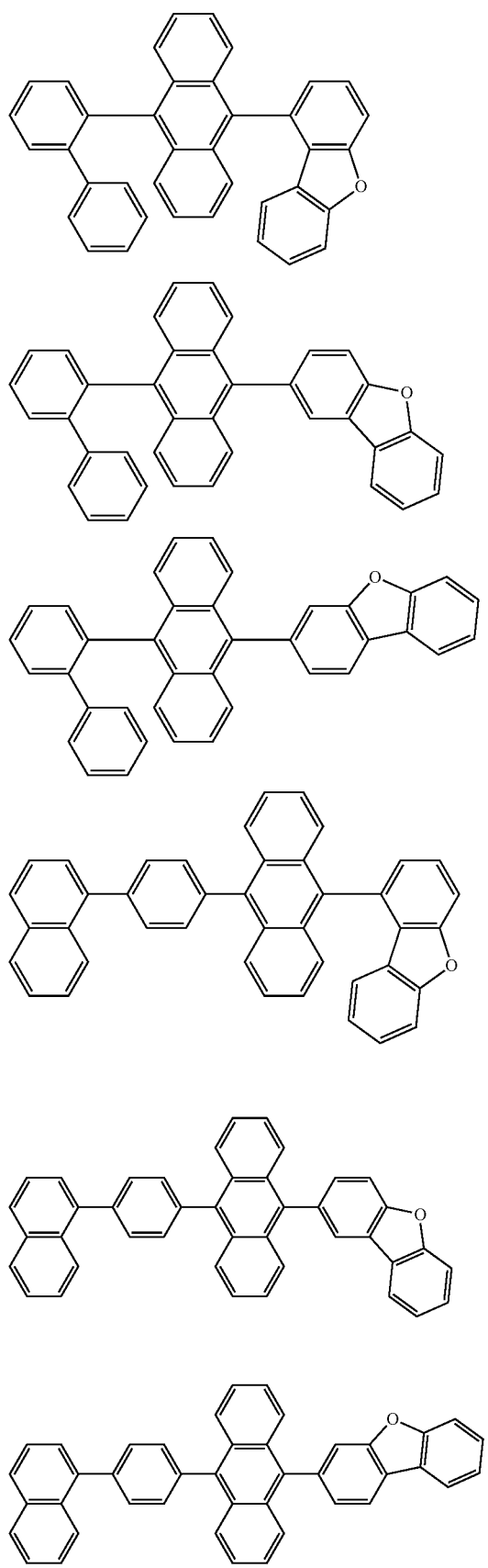

61
-continued
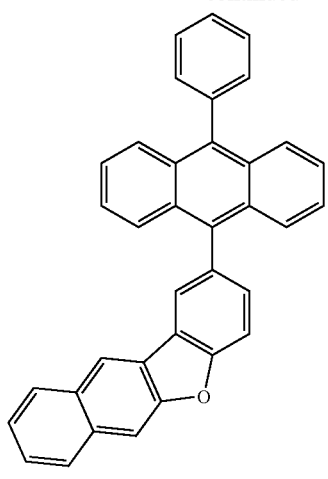
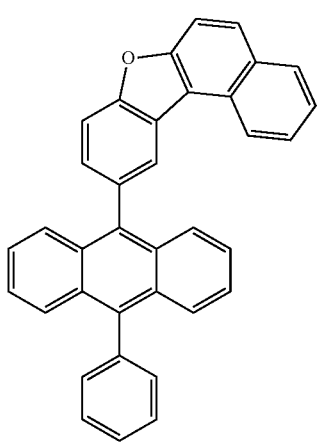
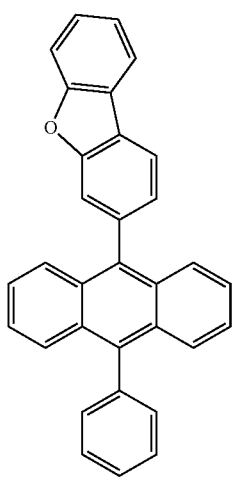
62
-continued
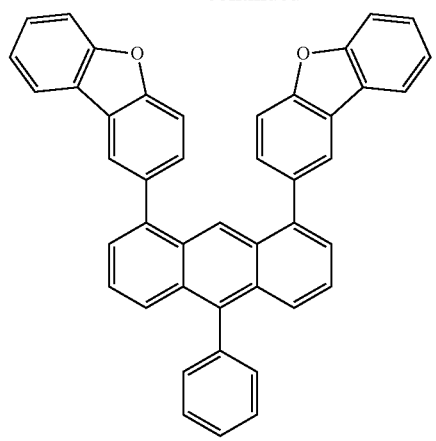
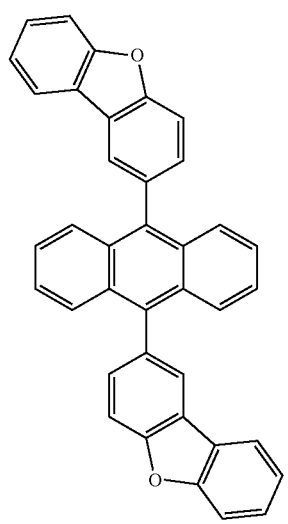
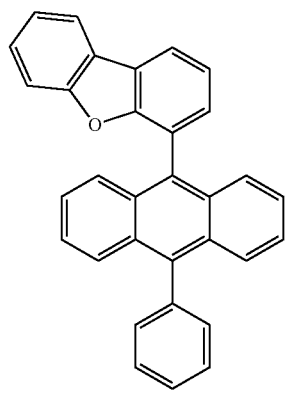

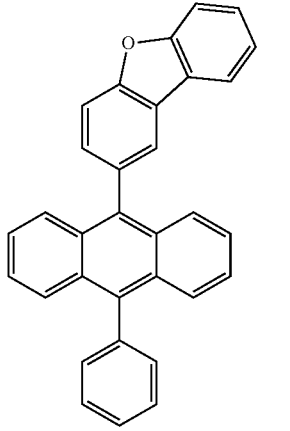
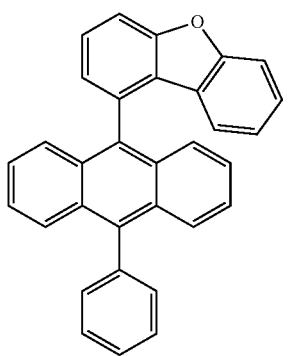
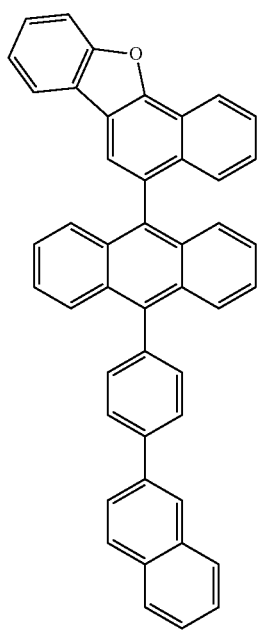
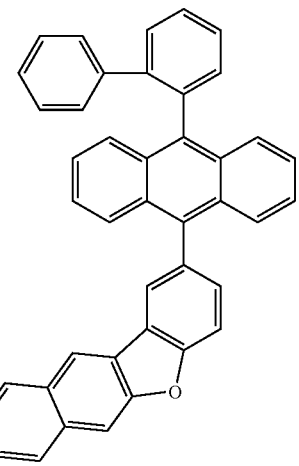
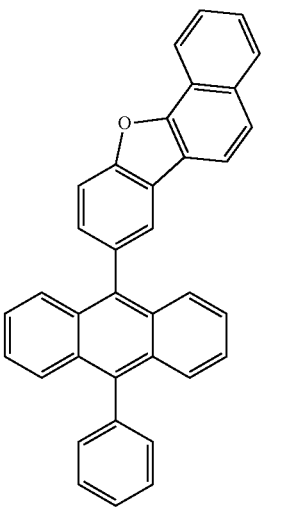
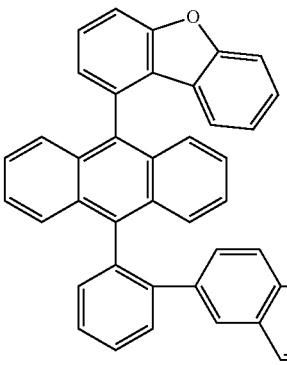
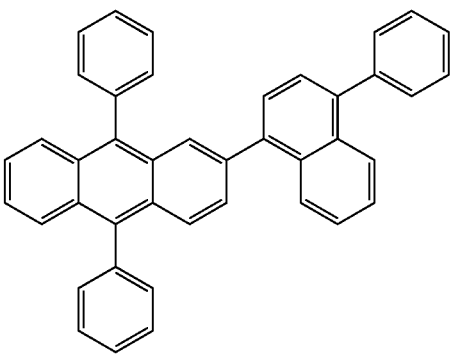

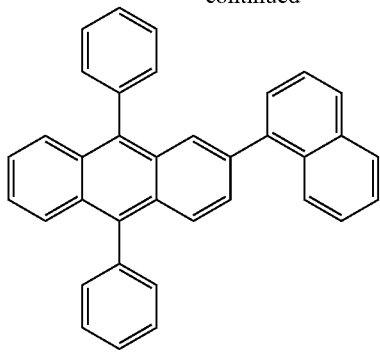

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and those in which one, two or more substituents selected from the group consisting of an aryl group, a silyl group, an alkyl group, a cycloalkyl group and an arylamino group that is substituted or unsubstituted can be used. Specifically, styrylamine, styryldiamine, styryltriamine, styryltetramine and the like can be included, however, the styrylamine compound is not limited thereto. In addition, as the metal complex, iridium complexes, platinum complexes and the like can be included, however, the metal complex is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including Alq$_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxy-benzo[h]quinolinato)zinc, bis(2-methyl-8-quinolinato)-chlorogallium, bis(2-methyl-8-quinolinato) (o-cresolato)-gallium, bis(2-methyl-8-quinolinato)(1-naphtholato) aluminum, bis(2-methyl-8-quinolinato) (2-naphtholato) gallium and the like, but is not limited thereto.

The capping layer (14) can perform a role of preventing inflow of oxygen and moisture inflowing from the outside by covering an organic light emitting device, and enhancing efficiency of light passing through the cathode (11). The capping layer is a functional layer formed to be thin enough to have almost no optical effect, and the capping layer can be formed to have a thickness of 5 nm or less, and can be an insulating layer formed with an organic material or an inorganic material.

The organic light emitting device according to the present specification can be a top-emission type, a bottom-emission type or a dual-emission type depending on the materials used.

According to one embodiment of the present specification, the compound of Chemical Formula 1 can be included in an organic solar cell or an organic transistor in addition to an organic light emitting device.

EXAMPLES

<Synthesis Example 1> Preparation of Compound 1

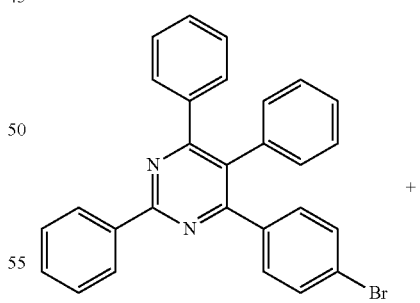

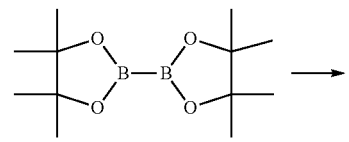

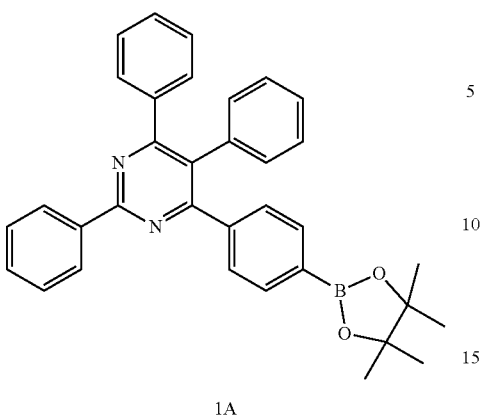

1A

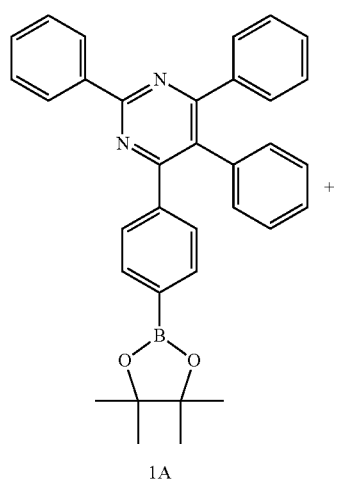

1A

+

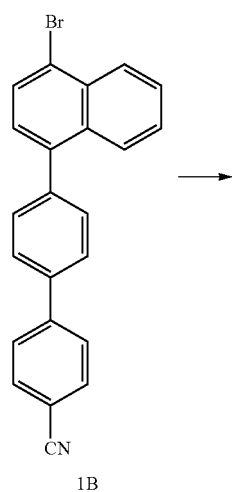

1B

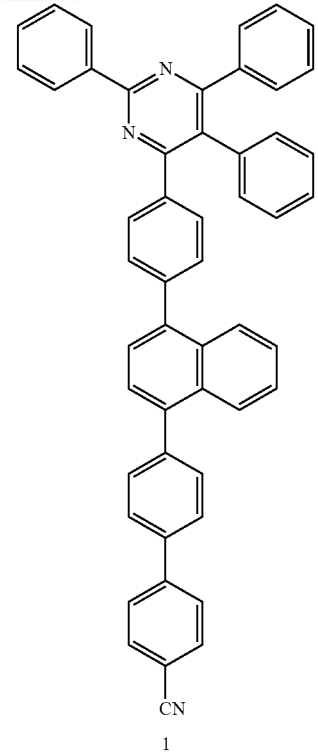 [SMILES: N#Cc1ccc(-c2ccc(-c3ccc(-c4ccc(-c5nc(-c6ccccc6)nc(-c6ccccc6)c5-c5ccccc5)cc4)c4ccccc34)cc2)cc1]

1

(1) Preparation of Compound 1A 4-(4-Bromophenyl)-2,5,6-triphenylpyrimidine (30 g, 64.8 mmol), bispinacolatodiborane (18.1 g, 71.3 mmol) and potassium acetate (19.1 g, 213.9 mmol) were dissolved in dioxin (700 and heated to 130° C. Bisdibenzylideneacetone palladium (Pd(dba$_2$)) (1.12 g, 1.94 mmol) and tricyclohexylphosphine (PCy$_3$) (1.12 g, 3.88 mmol) were added thereto, and the result was refluxed for 4 hours. After cooling the result to room temperature, the solvent was removed. The result was purified using column chromatography to obtain Compound 1A (28 g, yield 85%).

MS: [M+H]$^+$=510

(2) Preparation of Compound 1

Compound 1A (12.8 g, 25 mmol), Compound 1B (5.8 g, 25 mmol) and potassium carbonate (K$_2$CO$_3$) (10.4 g, 75 mmol) were dissolved in tetrahydrofuran (THF) (300 mL) and H$_2$O (100 ml), and heated to 90° C. Tetrakis(triphenylphosphine)palladium (Pd(PPh$_3$)$_4$) (0.58 g, 0.5 mmol) was added thereto, and the result was refluxed for 4 hours. After cooling the result to room temperature, the water layer was removed. Magnesium sulfate (MgSO$_4$) was introduced to the organic layer, and the layer was filtered. The result was concentrated, and then purified using column chromatography to obtain Compound 1 (15 g, yield 87%).

MS: [M+H]$^+$=687

<Synthesis Example 2> Preparation of Compound 2

<Synthesis Example 3> Preparation of Compound 3

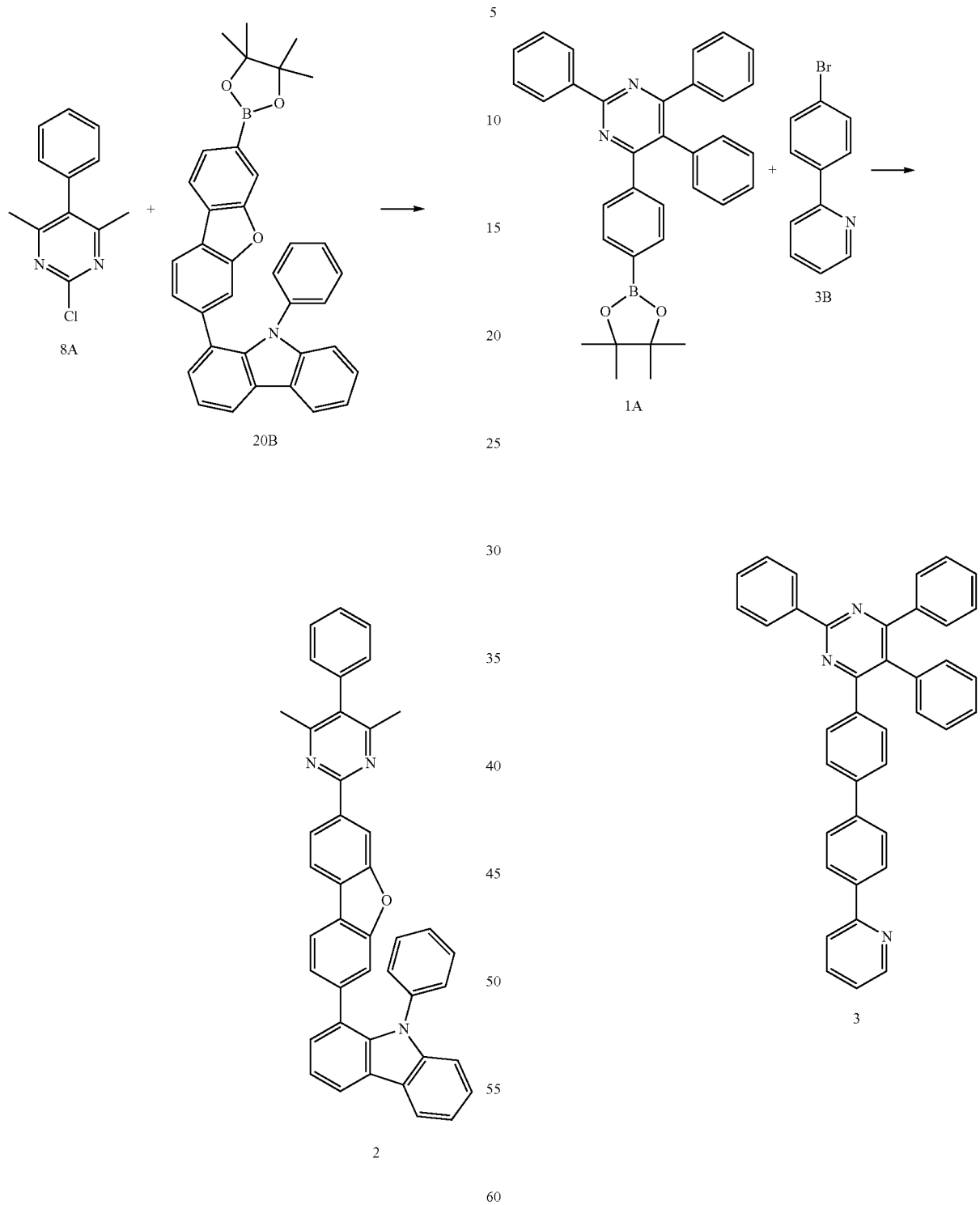

Compound 2 (11.5 g, yield 78%) was obtained in the same manner as in the preparation of Compound 1 except that Compound 8A was used instead of Compound 1A, and Compound 20B was used instead of Compound 1B.

MS: [M+H]$^+$=591

Compound 3 (10 g, yield 75%) was obtained in the same manner as in the preparation of Compound 1 except that Compound 3B was used instead of Compound 1B.

MS: [M+H]$^+$=537

<Synthesis Example 4> Preparation of Compound 4
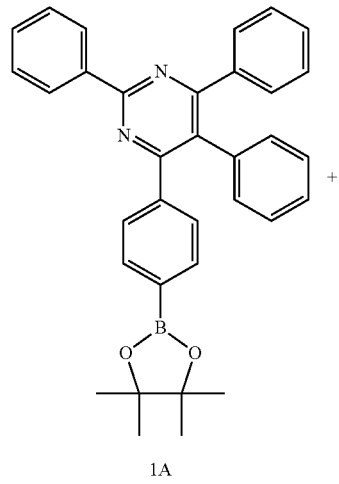
1A
+
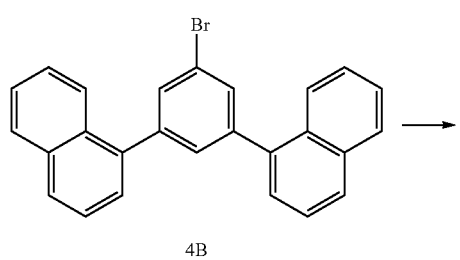
4B
→
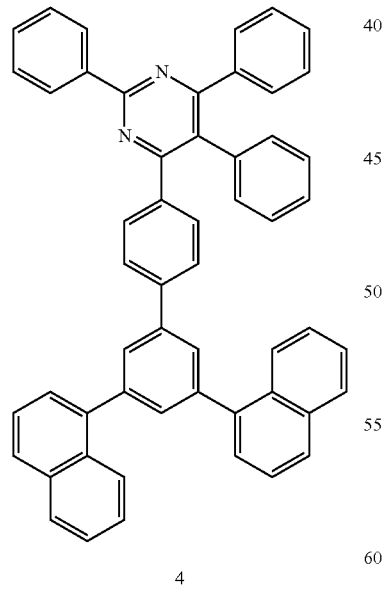
4
Compound 4 (14 g, yield 79%) was obtained in the same manner as in the preparation of Compound 1 except that Compound 4B was used instead of Compound 1B.
MS: [M+H]$^+$=712
<Synthesis Example 5> Preparation of Compound 5
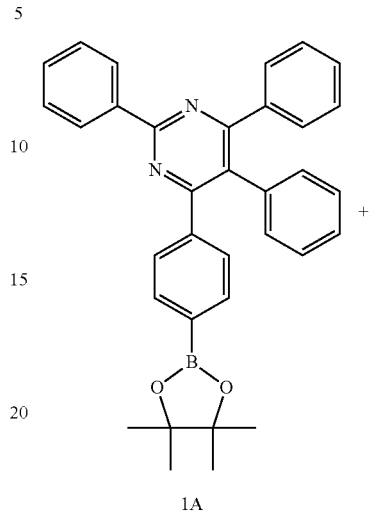
1A
+
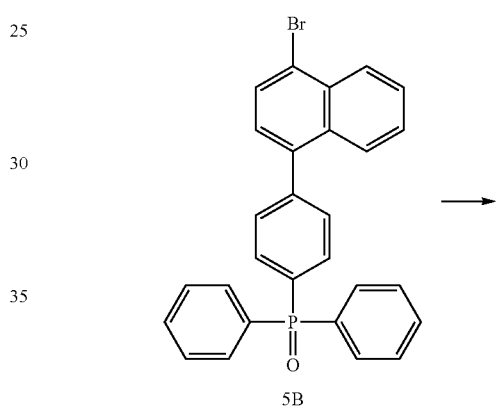
5B
→
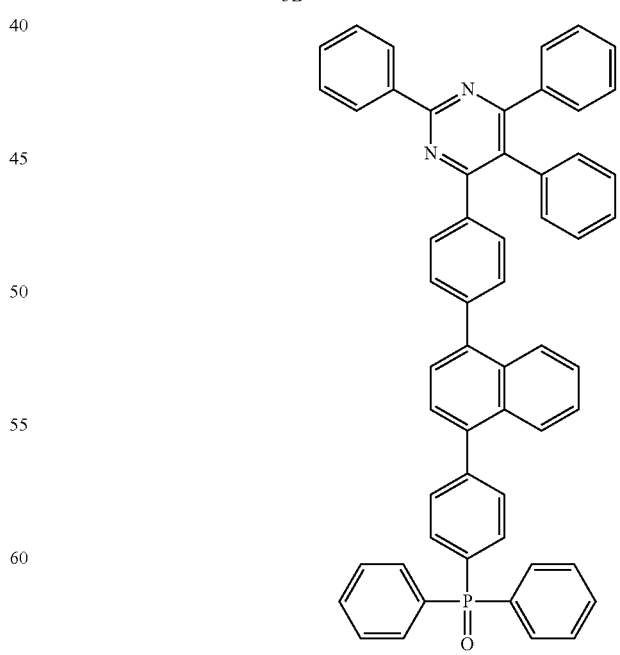
5

Compound 5 (13.5 g, yield 69%) was obtained in the same manner as in the preparation of Compound 1 except that Compound 5B was used instead of Compound 1B.

MS: [M+H]$^+$=786

<Synthesis Example 6> Preparation of Compound 6

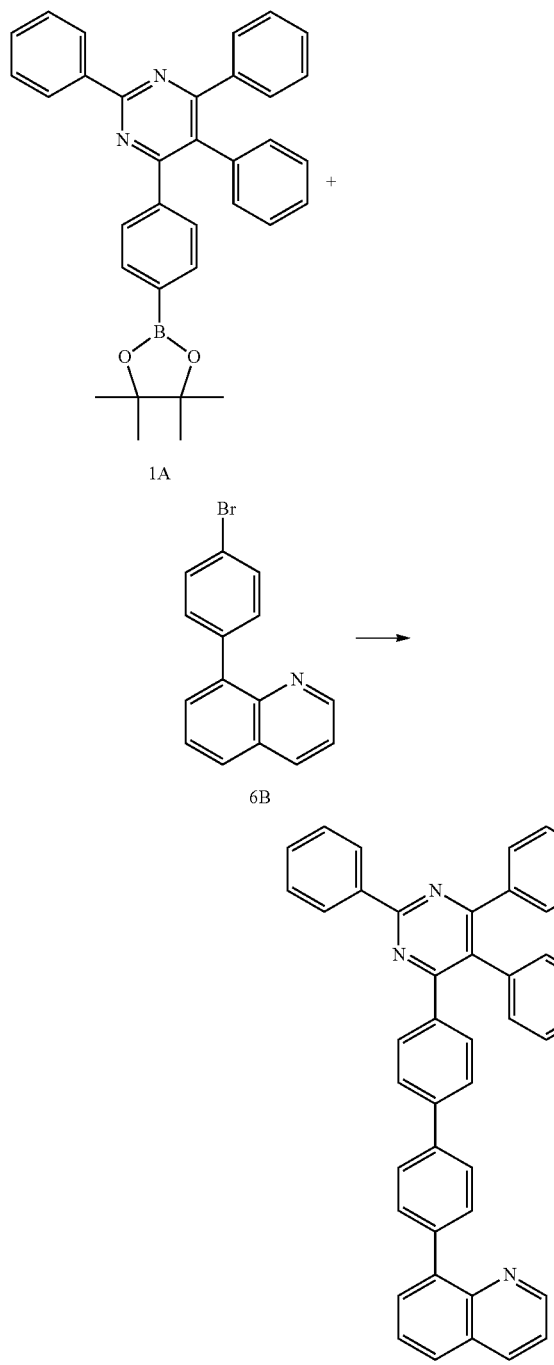

Compound 6 (12 g, yield 82%) was obtained in the same manner as in the preparation of Compound 1 except that Compound 6B was used instead of Compound 1B.

MS: [M+H]$^+$=587

<Synthesis Example 7> Preparation of Compound 7

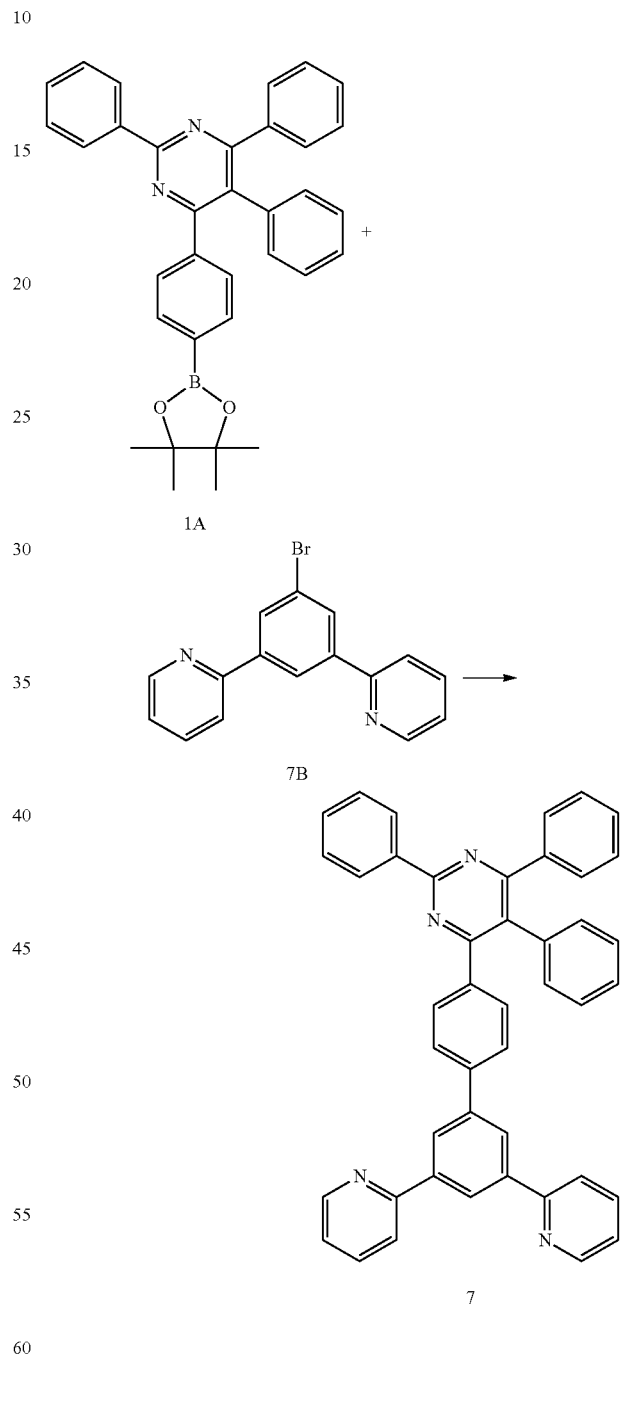

Compound 7 (10 g, yield 65%) was obtained in the same manner as in the preparation of Compound 1 except that Compound 7B was used instead of Compound 1B.

MS: [M+H]$^+$=614

\<Synthesis Example 8\> Preparation of Compound 8

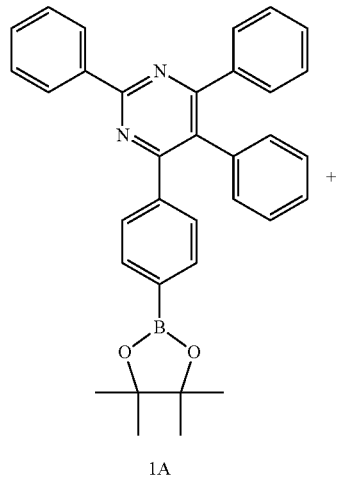

Compound 8 (12 g, yield 79%) was obtained in the same manner as in the preparation of Compound 1 except that Compound 8B was used instead of Compound 1B.

MS: $[M+H]^+$=611

\<Synthesis Example 9\> Preparation of Compound 9

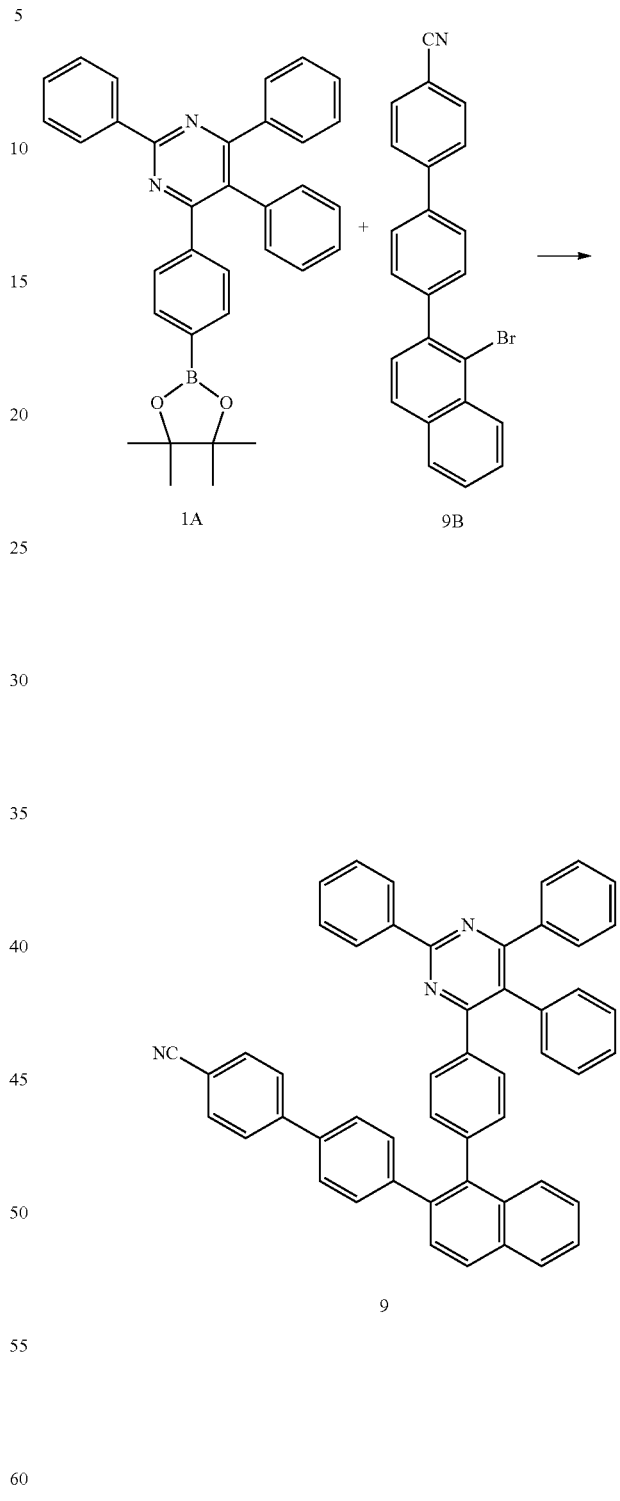

Compound 9 (14.5 g, yield 84%) was obtained in the same manner as in the preparation of Compound 1 except that Compound 9B was used instead of Compound 1B.

MS: $[M+H]^+$=687

<Synthesis Example 10> Preparation of Compound 10

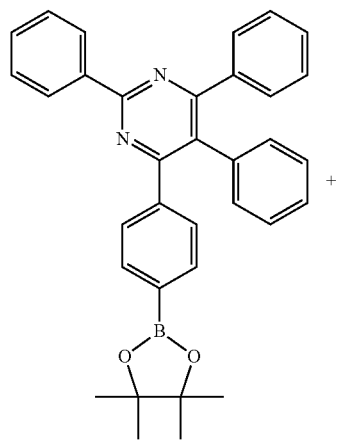

1A

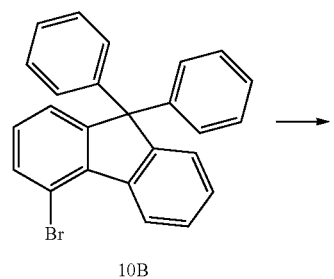

10B

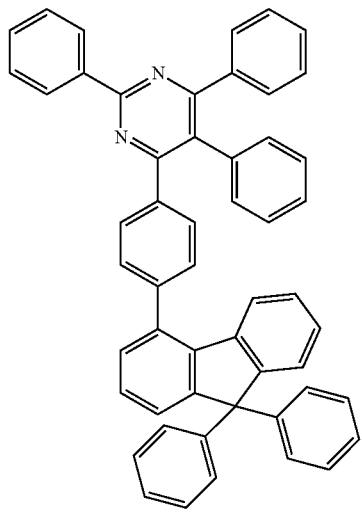

10

Compound 10 (16 g, yield 91%) was obtained in the same manner as in the preparation of Compound 1 except that Compound 10B was used instead of Compound 1B.

MS: [M+H]$^+$=700

<Synthesis Example 11> Preparation of Compound 11

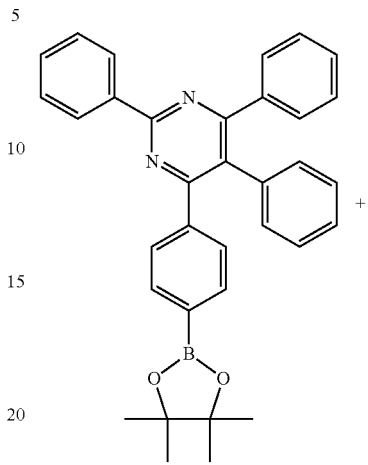

1A

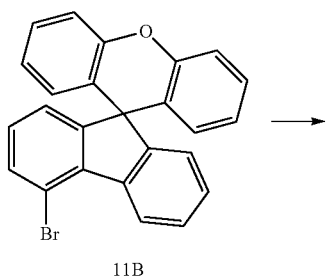

11B

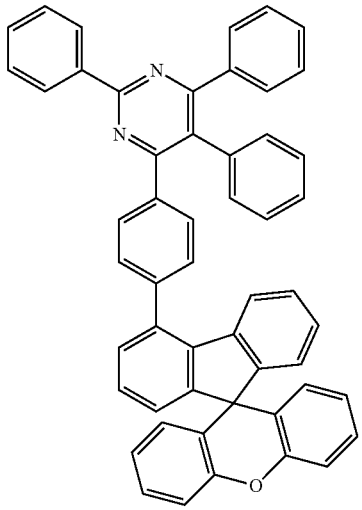

11

Compound 11 (15 g, yield 84%) was obtained in the same manner as in the preparation of Compound 1 except that Compound 11B was used instead of Compound 1B.

MS: [M+H]$^+$=714

<Synthesis Example 12> Preparation of Compound 12

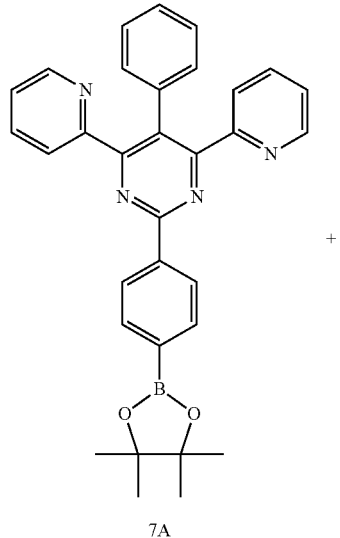

7A

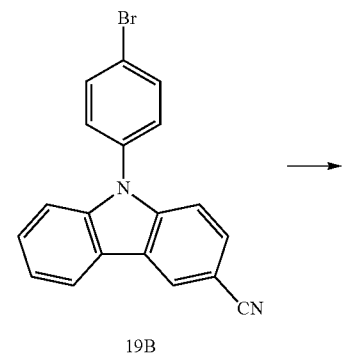

19B

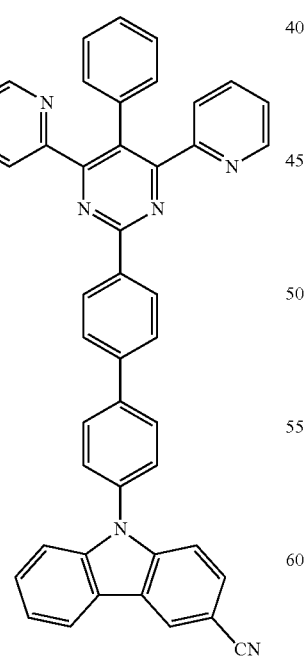

12

Compound 12 (9.8 g, yield 60%) was obtained in the same manner as in the preparation of Compound 1 except that Compound 7A was used instead of Compound 1A, and Compound 19B was used instead of Compound 1B.

MS: [M+H]⁺=652

<Synthesis Example 13> Preparation of Compound 13

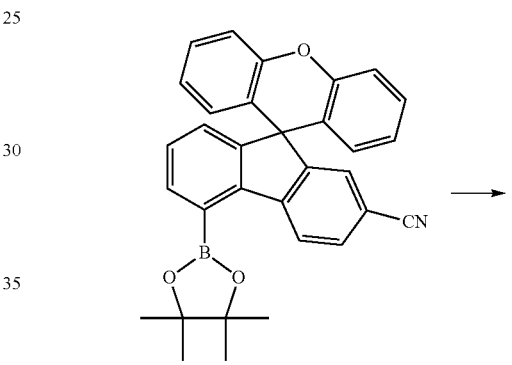

2A

13B

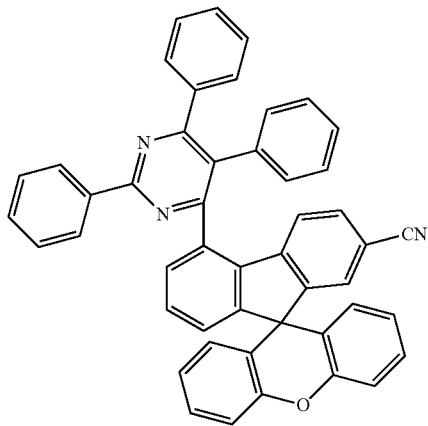

13

Compound 13 (13 g, yield 78%) was obtained in the same manner as in the preparation of Compound 1 except that Compound 2A was used instead of Compound 1A, and Compound 13B was used instead of Compound 1B.

MS: [M+H]⁺=663

<Synthesis Example 14> Preparation of Compound 14

<Synthesis Example 15> Preparation of Compound 15

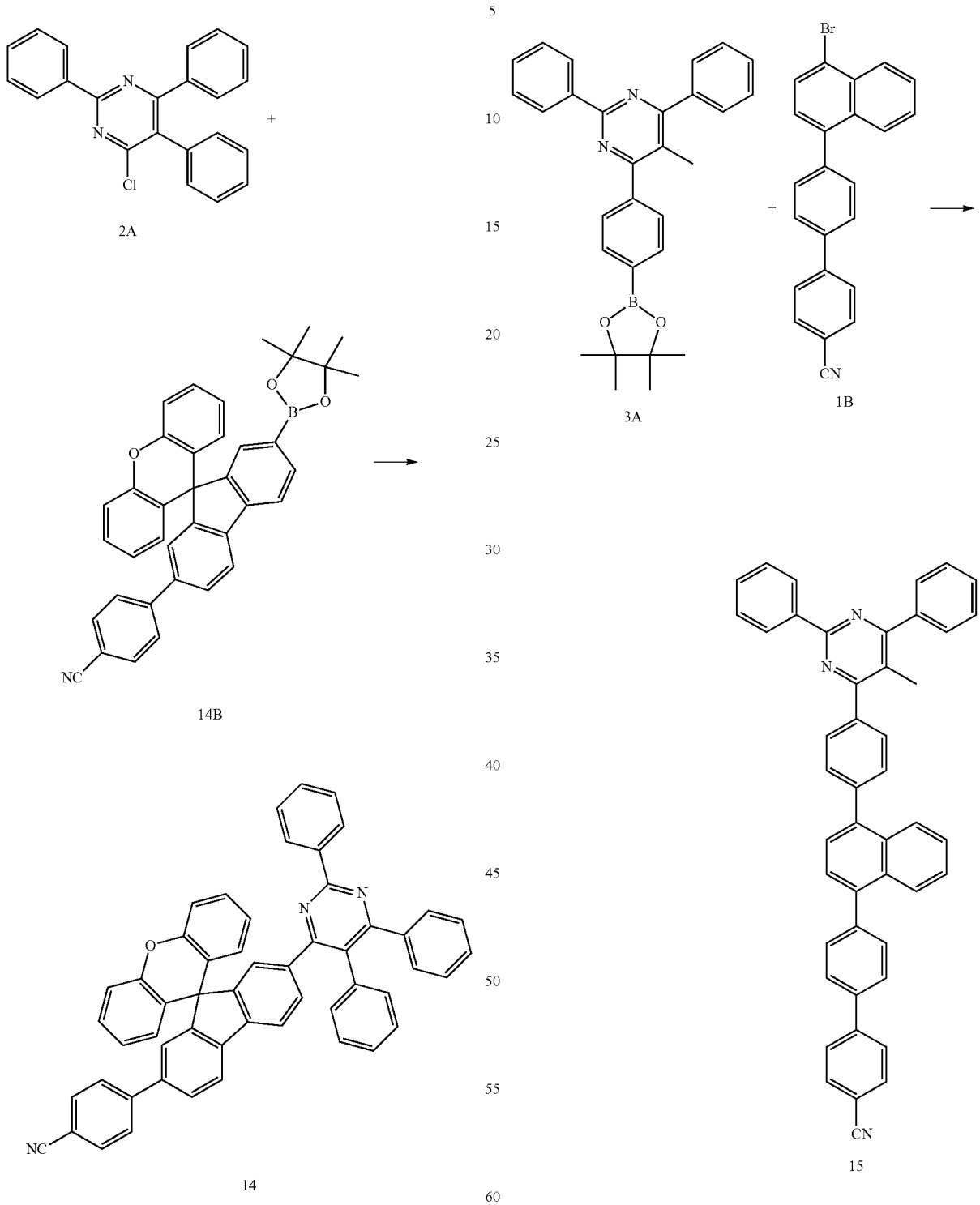

Compound 14 (16 g, yield 87%) was obtained in the same manner as in the preparation of Compound 1 except that Compound 2A was used instead of Compound 1A, and Compound 14B was used instead of Compound 1B.

MS: [M+H]⁺=739

Compound 15 (12 g, yield 77%) was obtained in the same manner as in the preparation of Compound 1 except that Compound 3A was used instead of Compound 1A.

MS: [M+H]⁺=625

\<Synthesis Example 16\> Preparation of Compound 16
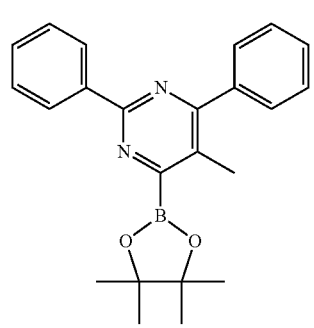
3A
+
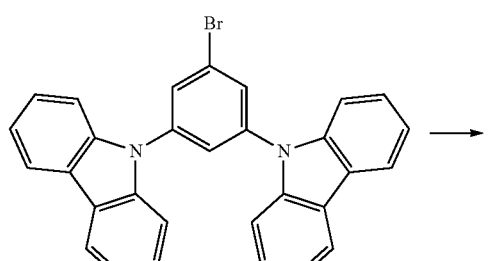
15B
→
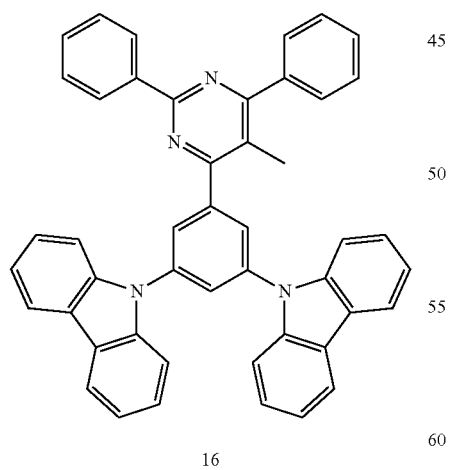
16
Compound 16 (10 g, yield 61%) was obtained in the same manner as in the preparation of Compound 15 except that Compound 15B was used instead of Compound 1B.
MS: [M+H]$^+$=652
\<Synthesis Example 17\> Preparation of Compound 17
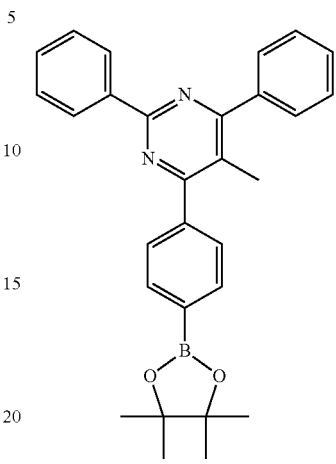
3A
+
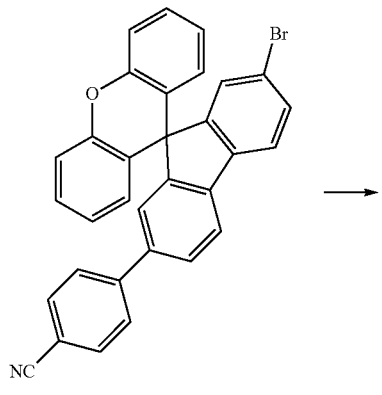
16B
→
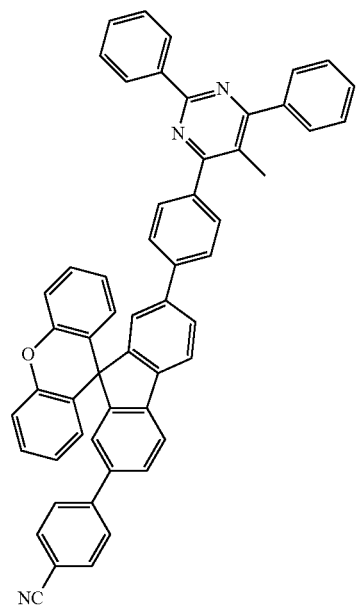
17

Compound 17 (15 g, yield 80%) was obtained in the same manner as in the preparation of Compound 15 except that Compound 16B was used instead of Compound 1B.

MS: $[M+H]^+$=753

<Synthesis Example 18> Preparation of Compound 18

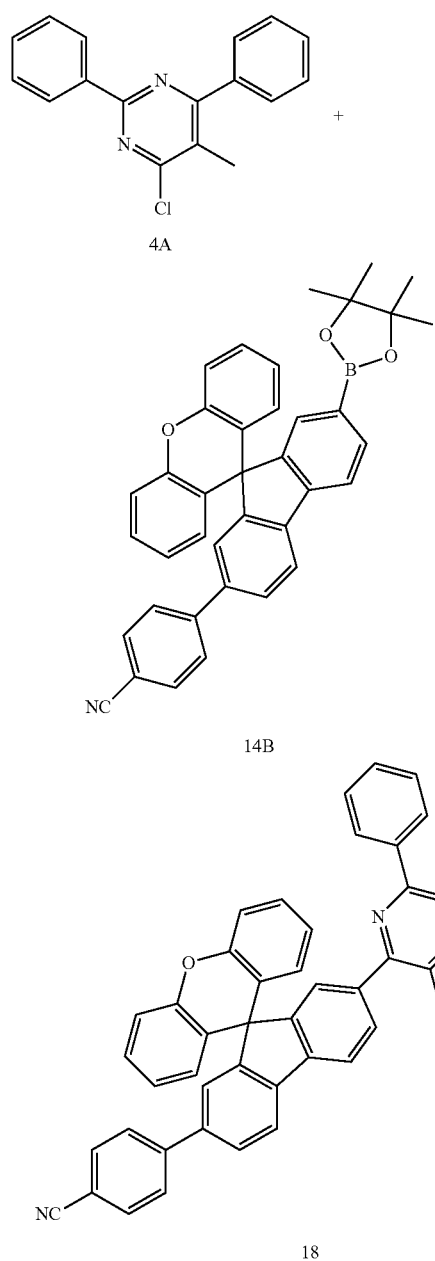

<Synthesis Example 19> Preparation of Compound 19

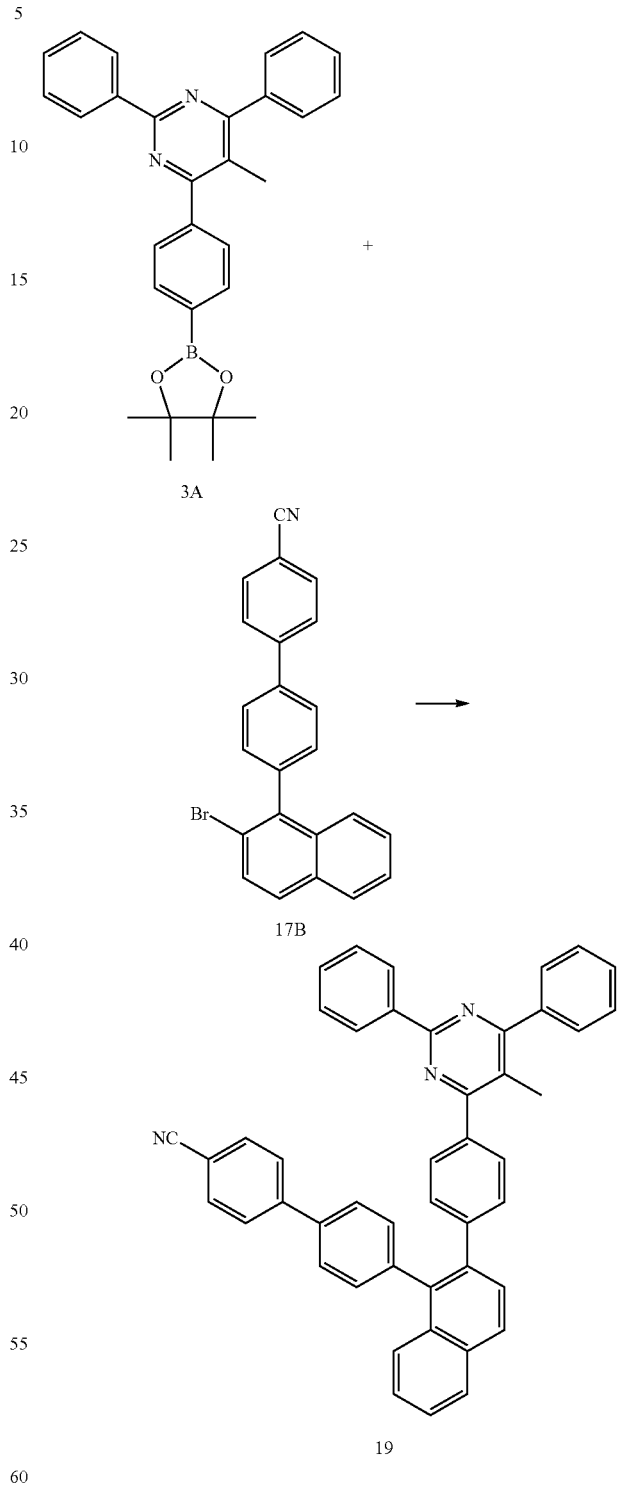

Compound 18 (12.4 g, yield 73%) was obtained in the same manner as in the preparation of Compound 14 except that Compound 4A was used instead of Compound 2A.

MS: $[M+H]^+$=677

Compound 19 (11.2 g, yield 72%) was obtained in the same manner as in the preparation of Compound 15 except that Compound 17B was used instead of Compound 1B.

MS: $[M+H]^+$=625

<Synthesis Example 20> Preparation of Compound 20

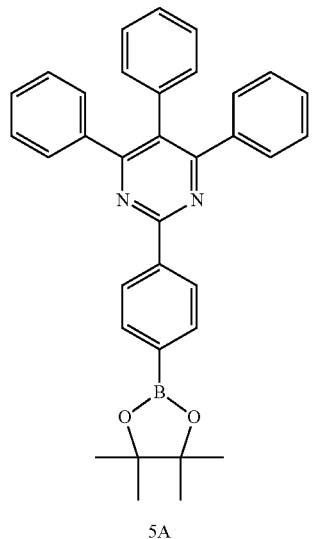

5A

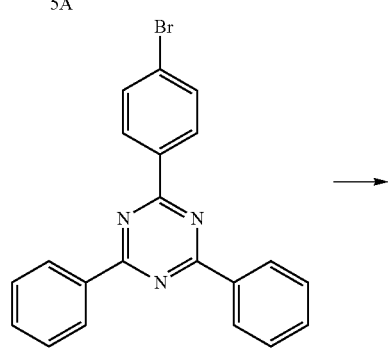

18B

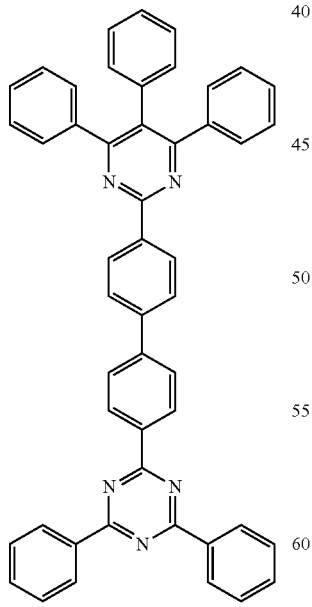

20

Compound 20 (11.2 g, yield 65%) was obtained in the same manner as in the preparation of Compound 1 except that Compound 5A was used instead of Compound 1A, and Compound 18B was used instead of Compound 1B.

MS: [M+H]$^+$=691

<Synthesis Example 21> Preparation of Compound 21

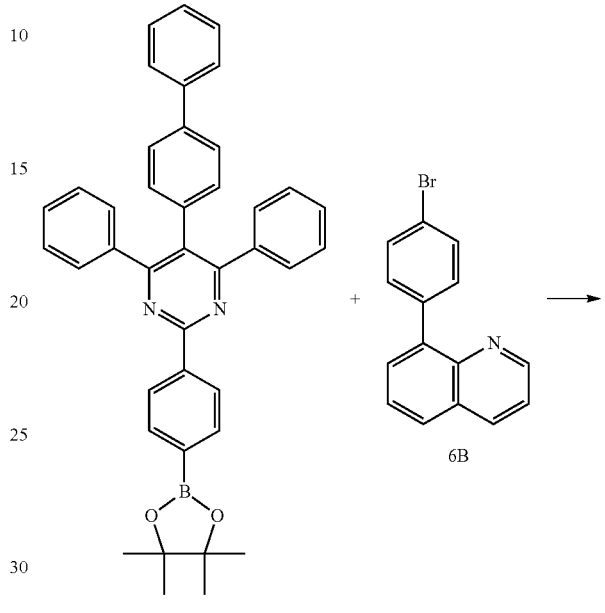

6A          6B

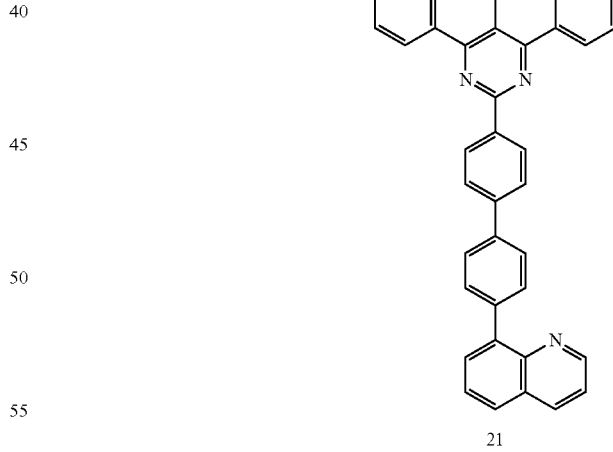

21

Compound 21 (10.1 g, yield 61%) was obtained in the same manner as in the preparation of Compound 6 except that Compound 6A was used instead of Compound 1A.

MS: [M+H]$^+$=663

<Synthesis Example 22> Preparation of Compound 22

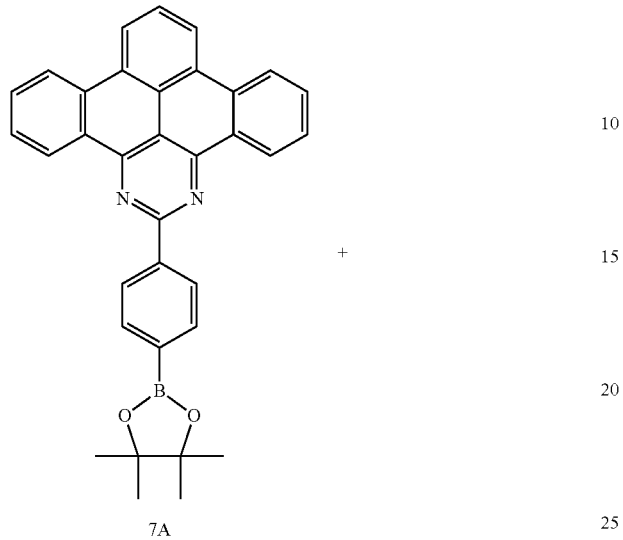

7A

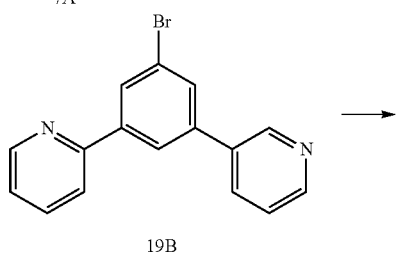

19B

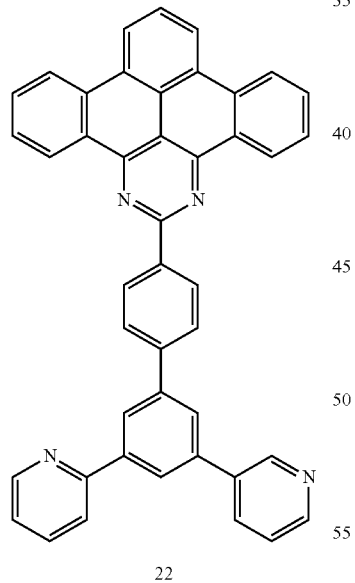

22

Compound 22 (10.5 g, yield 69%) was obtained in the same manner as in the preparation of Compound 21 except that Compound 7A was used instead of Compound 6A, and Compound 19B was used instead of Compound 6B.

MS: [M+H]$^+$=610

<Synthesis Example 23> Preparation of Compound 23

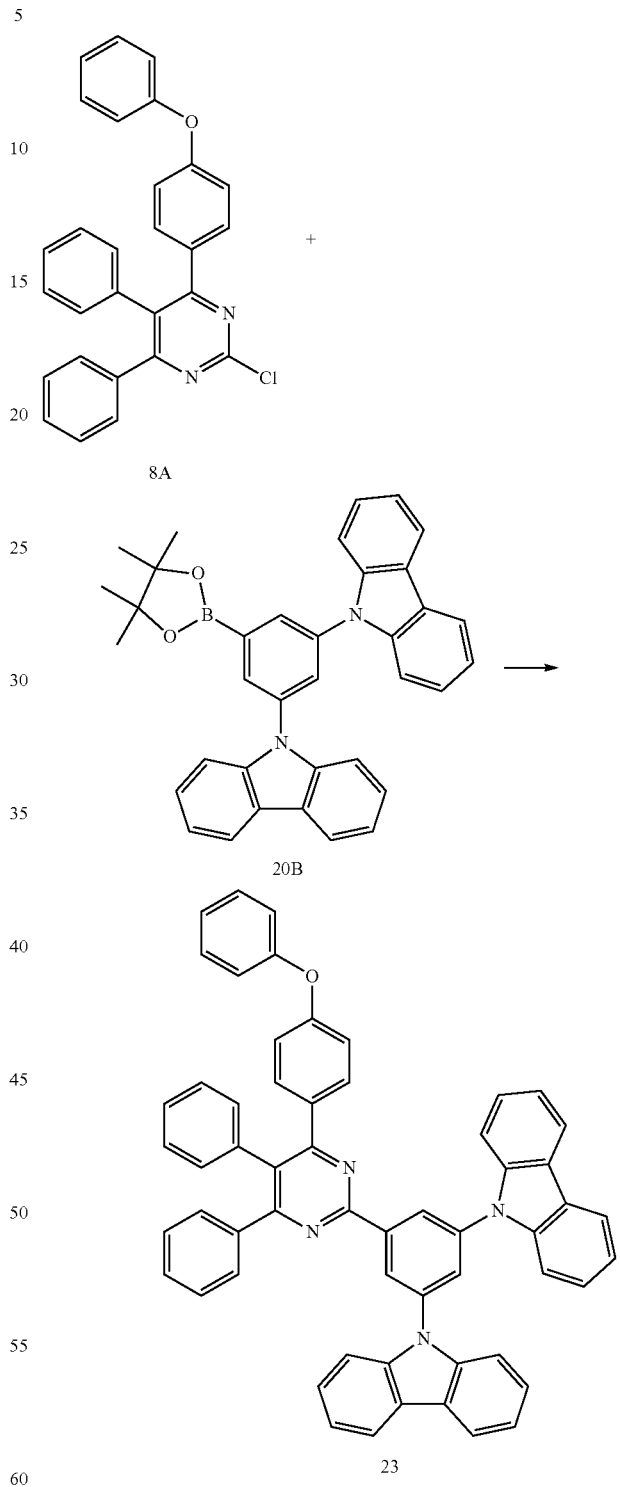

Compound 23 (13 g, yield 65%) was obtained in the same manner as in the preparation of Compound 21 except that Compound 8A was used instead of Compound 6A, and Compound 20B was used instead of Compound 6B.

MS: [M+H]$^+$=806

<Synthesis Example 24> Preparation of Compound 24

<Synthesis Example 25> Preparation of Compound 25

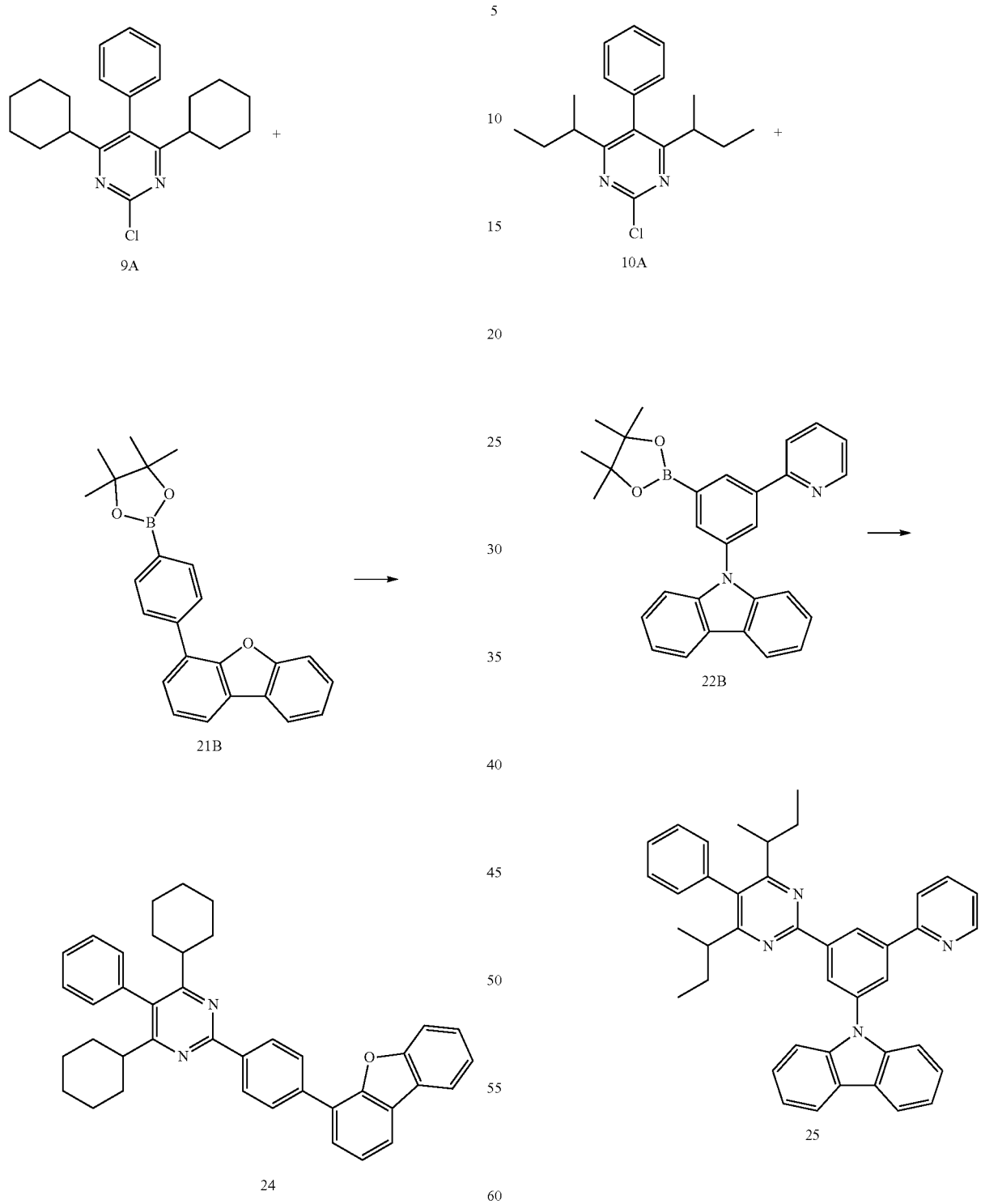

Compound 24 (10 g, yield 71%) was obtained in the same manner as in the preparation of Compound 21 except that Compound 9A was used instead of Compound 6A, and Compound 21B was used instead of Compound 6B.

MS: [M+H]⁺=562

Compound 25 (12 g, yield 82%) was obtained in the same manner as in the preparation of Compound 21 except that Compound 10A was used instead of Compound 6A, and Compound 22B was used instead of Compound 6B.

MS: [M+H]⁺=586

<Synthesis Example 26> Preparation of Compound 26

<Synthesis Example 27> Preparation of Compound 27

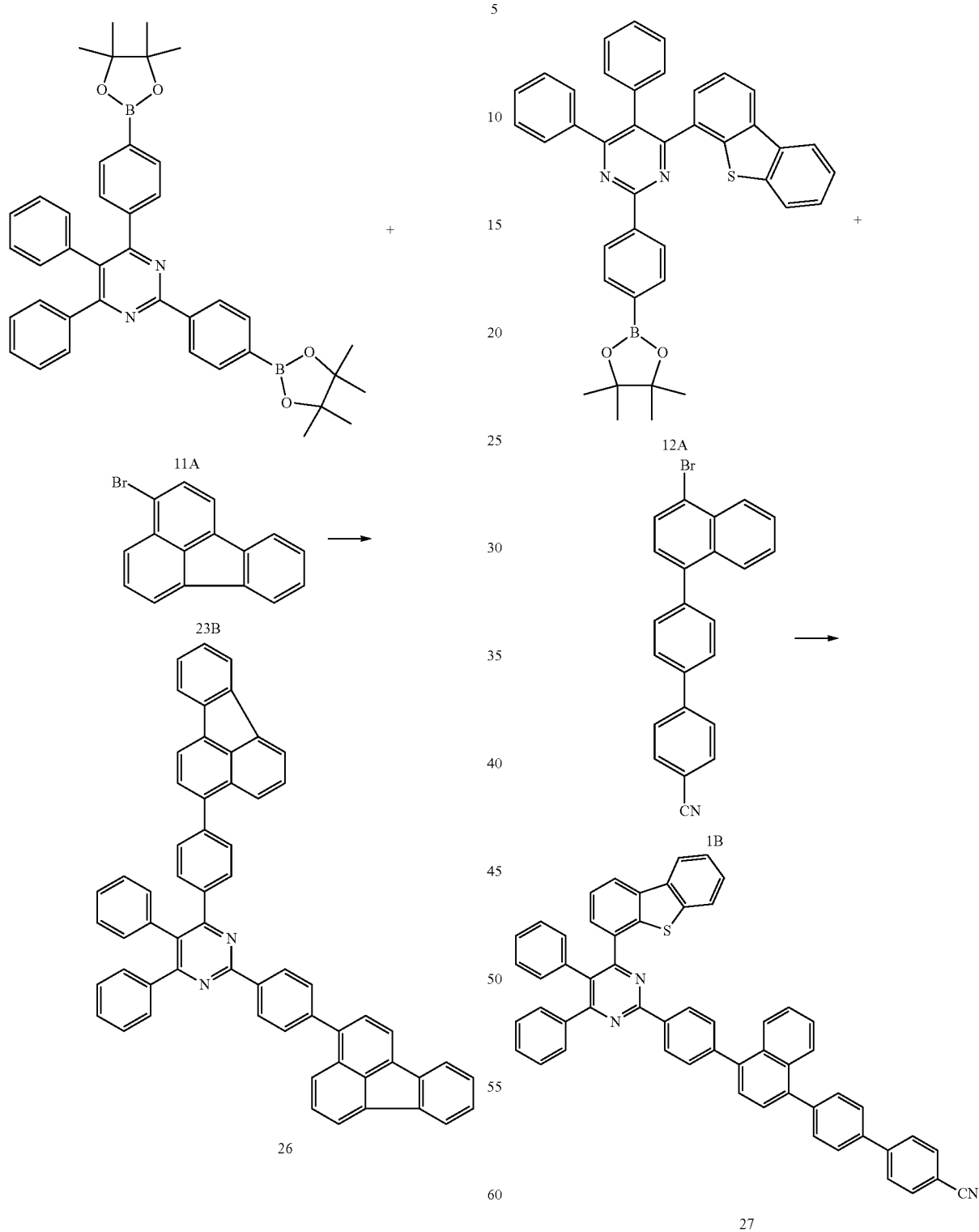

Compound 26 (15 g, yield 77%) was obtained in the same manner as in the preparation of Compound 21 except that Compound 11A was used instead of Compound 6A, and Compound 23B was used instead of Compound 6B.

MS: $[M+H]^+$=784

Compound 27 (12.5 g, yield 63%) was obtained in the same manner as in the preparation of Compound 1 except that Compound 12A was used instead of Compound 1A.

MS: $[M+H]^+$=793

Synthesis Example 28: Preparation of Compound 28

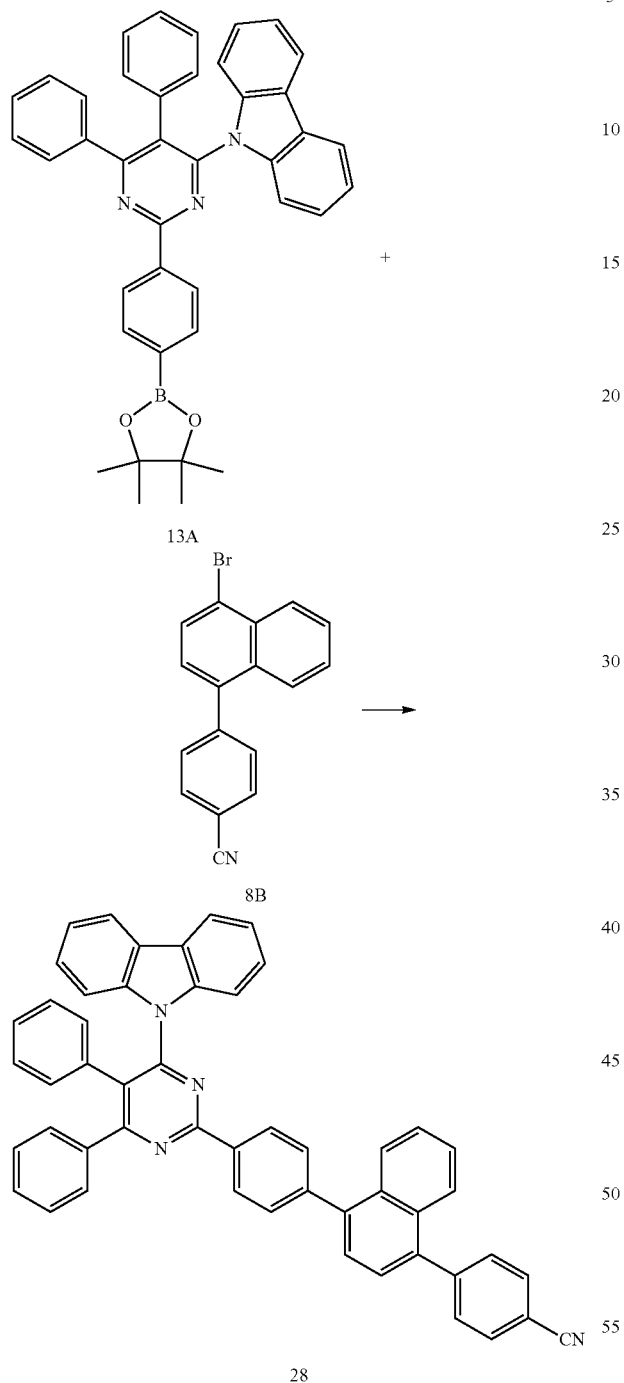

Compound 28 (10 g, yield 57%) was obtained in the same manner as in the preparation of Compound 8 except that Compound 13A was used instead of Compound 1A.

MS: $[M+H]^+ = 700$

Experimental Example 2: Manufacture of Device

Example 1-1

A glass substrate (corning 7059 glass) on which indium tin oxide (ITO) was coated as a thin film to a thickness of 100 nm was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned using solvents in the order of isopropyl alcohol, acetone and methanol solvents, and then dried.

On the transparent ITO electrode prepared as above, a hole injection layer was formed by thermal vacuum depositing hexanitrile hexaazatriphenylene (HAT-CN) shown below to a thickness of 50 nm. Thereon, HT1 (40 nm), shown below, a material transferring holes, was vacuum deposited, and then host BH1 and dopant BD1 compounds, shown below, were deposited to a thickness of 30 nm as a light emitting layer. After forming a hole blocking layer on the light emitting layer by depositing an ET-A compound, shown below, to a thickness of 5 nm, an electron injection and transfer layer was formed to a thickness of 35 nm by vacuum depositing Compound 1 and lithium quinolate (LiQ), shown below, in a weight ratio of 1:1. On the electron injection and transfer layer, a cathode was formed by consecutively depositing lithium fluoride (LiF) to a thickness of 1.2 nm and aluminum to a thickness of 200 nm. An organic light emitting device was manufactured as a result.

In the above-mentioned process, the deposition rates of the organic materials were maintained at 0.04 nm/sec to 0.07 nm/sec, the deposition rates of the lithium fluoride and the aluminum of the cathode were maintained at 0.03 nm/sec and 0.2 nm/sec, respectively. The degree of vacuum during the deposition was maintained at $2 \times 10^{-7}$ torr to $5 \times 10^{-6}$ torr.

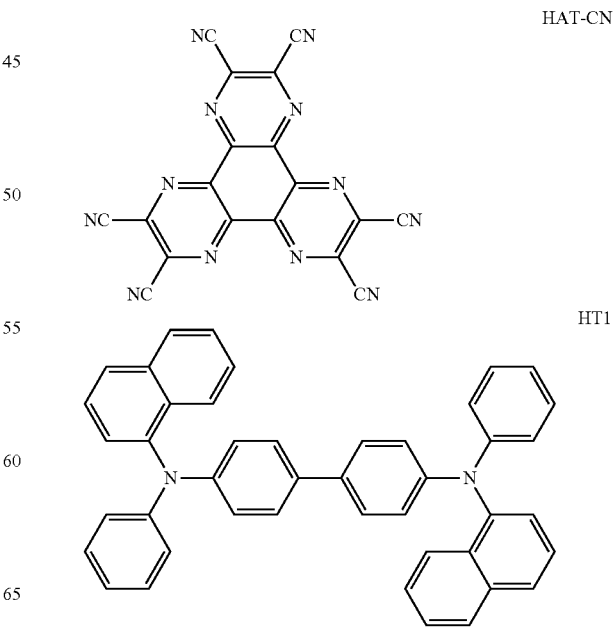

-continued
ET-A
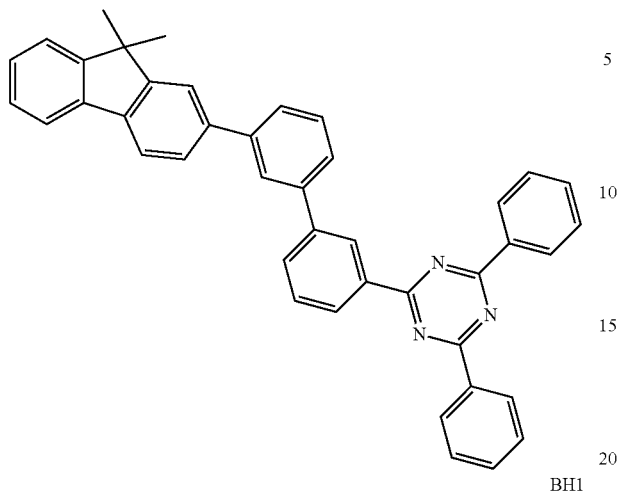
BH1
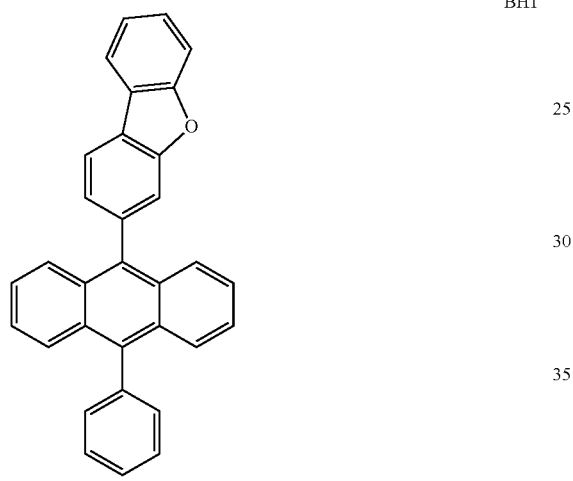
BD1
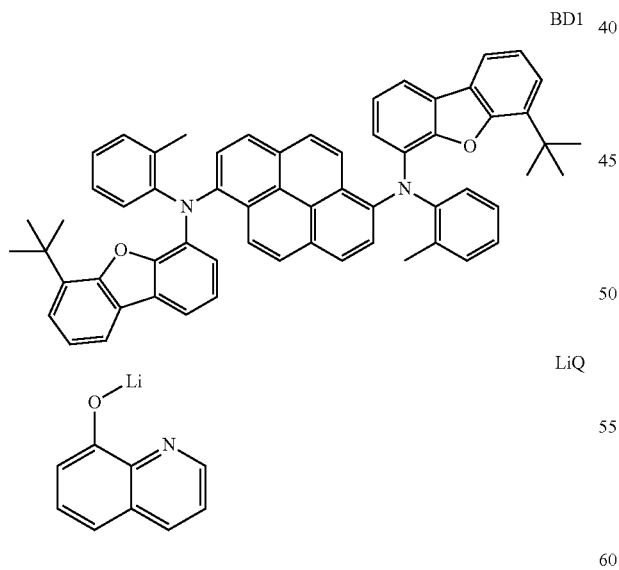
LiQ
the following Table 1 were each used instead of Compound 1 as the electron injection and transfer layer material.
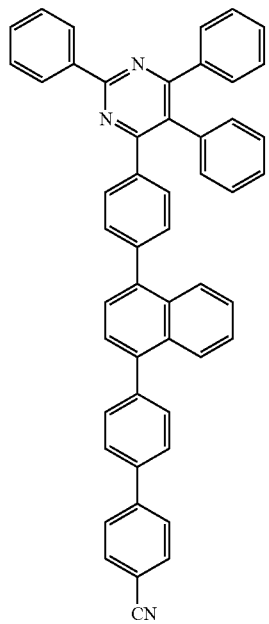
1
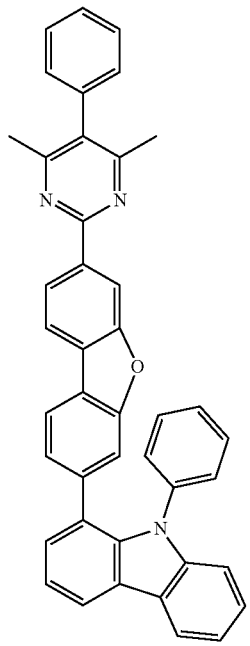
2
Examples 1-2 to 1-28 and Comparative Examples 1-1 to 1-6
An organic light emitting device of each of examples and comparative examples was manufactured in the same manner as in Example 1-1 except that compounds described in

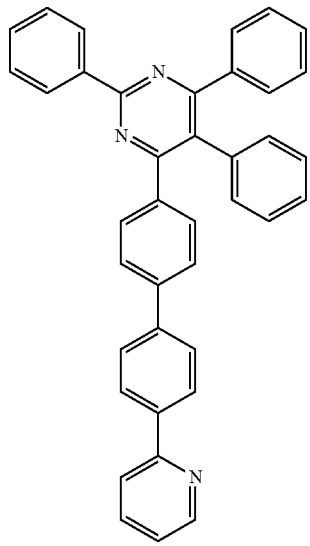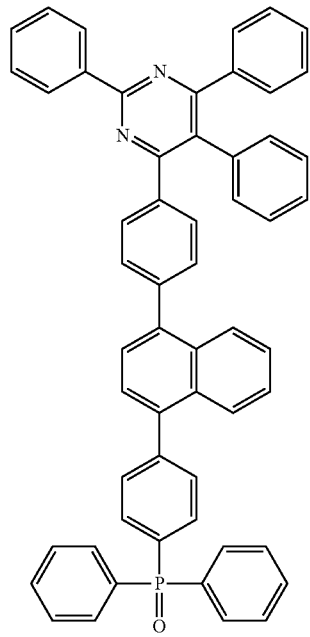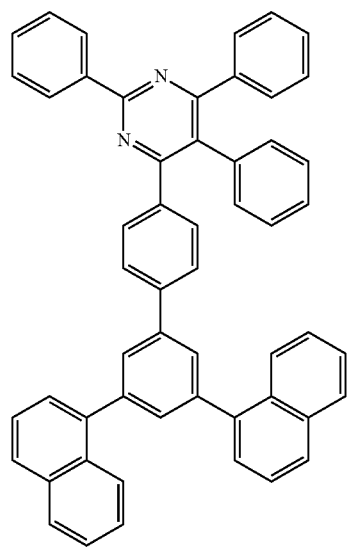

101
-continued
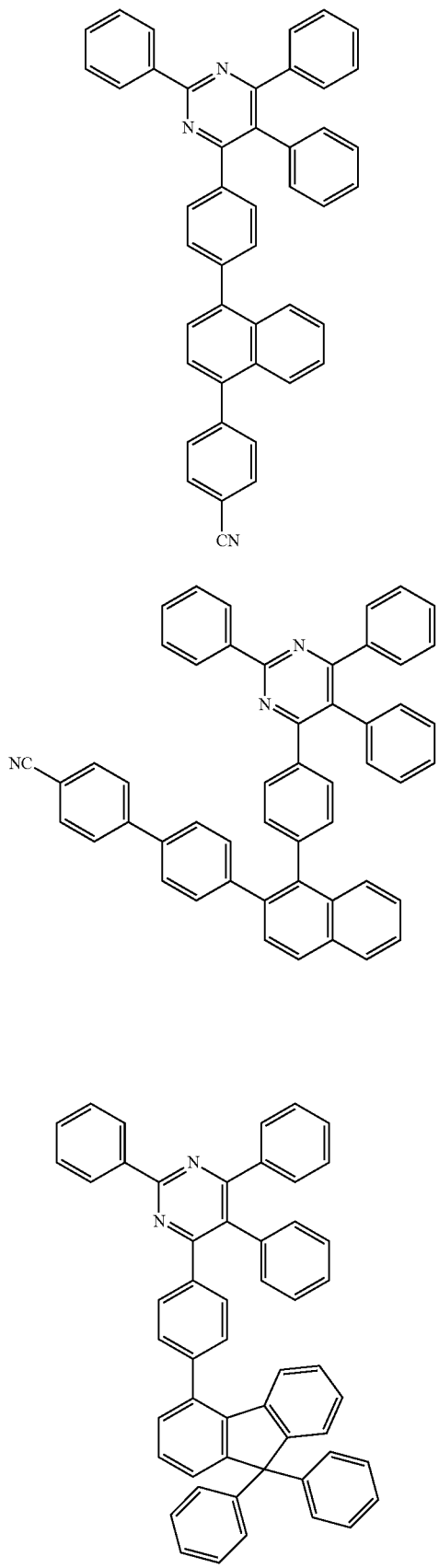
102
-continued
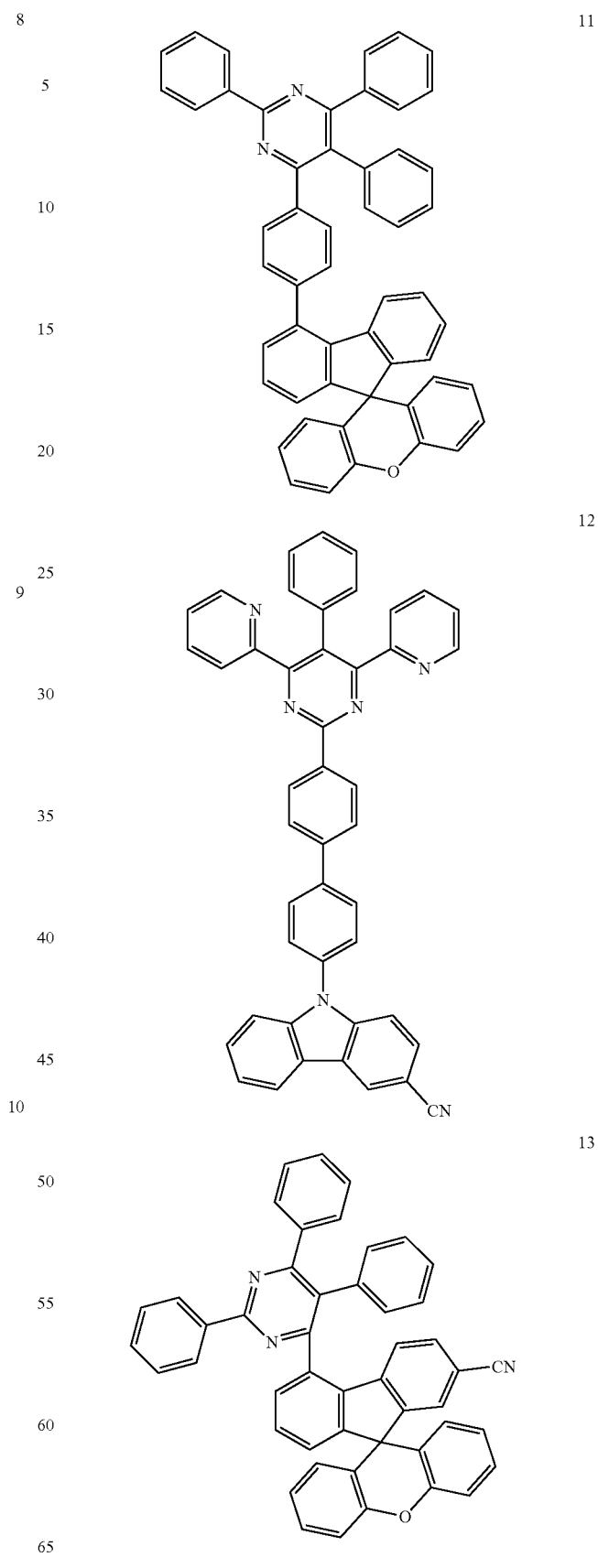

14
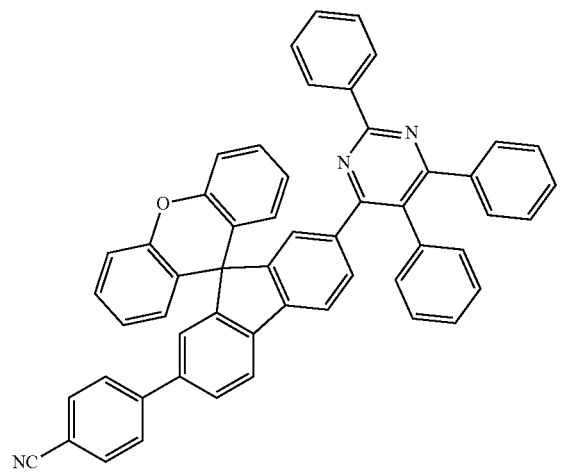
15
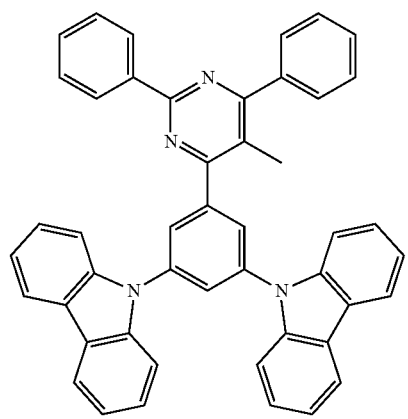
16
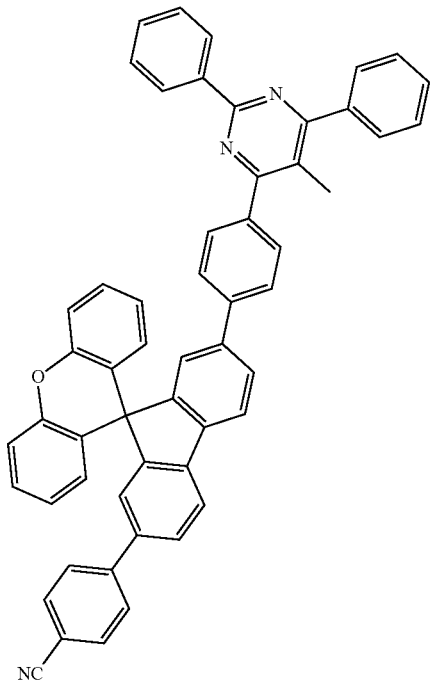
17
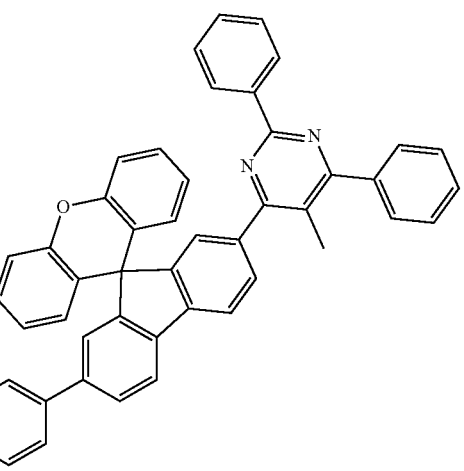
18
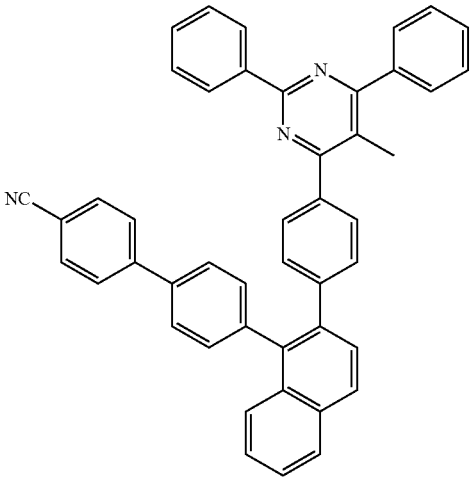
19

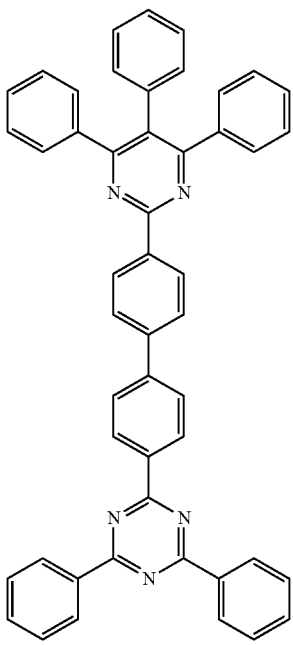
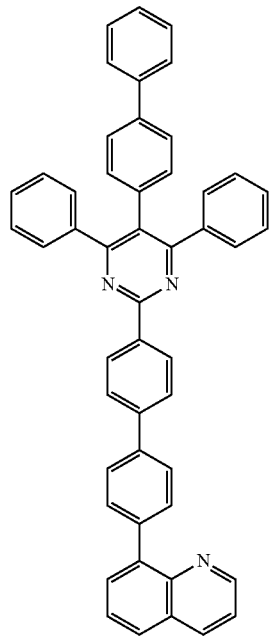
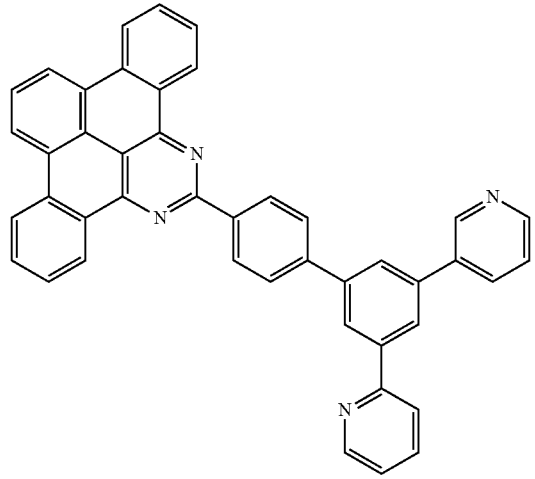
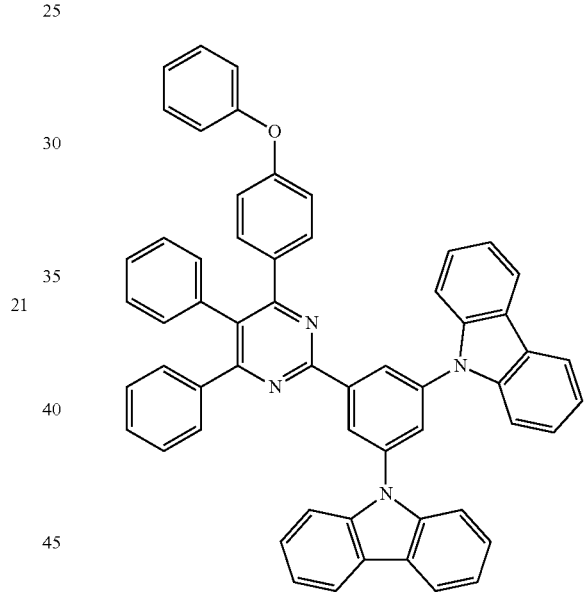
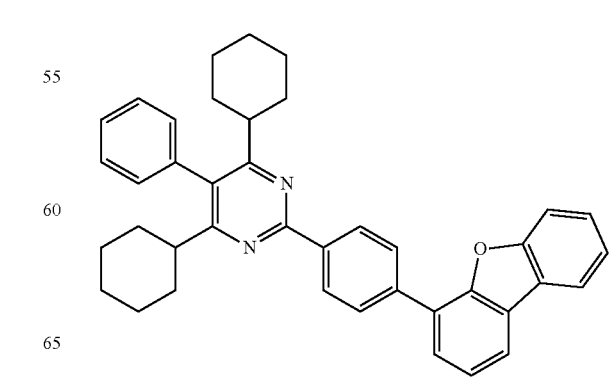

107
-continued
25
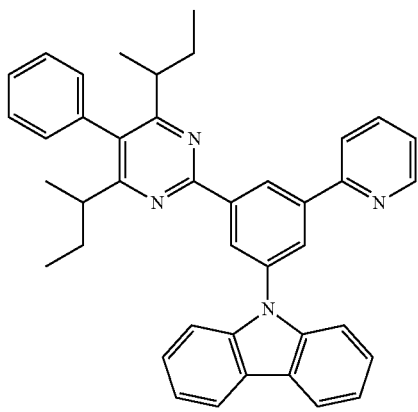
26
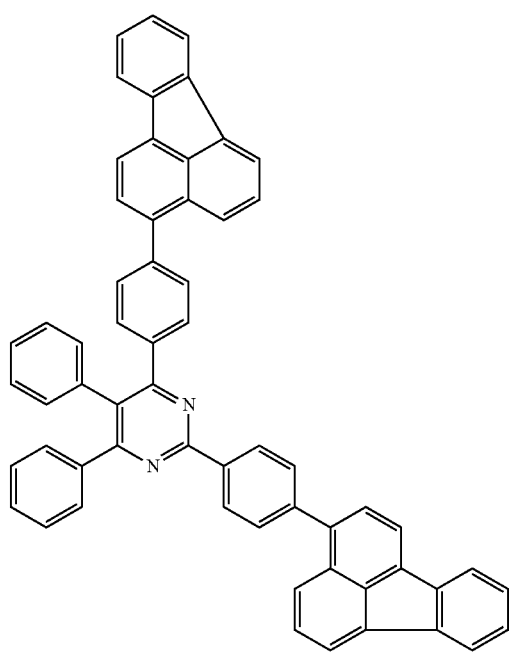
27
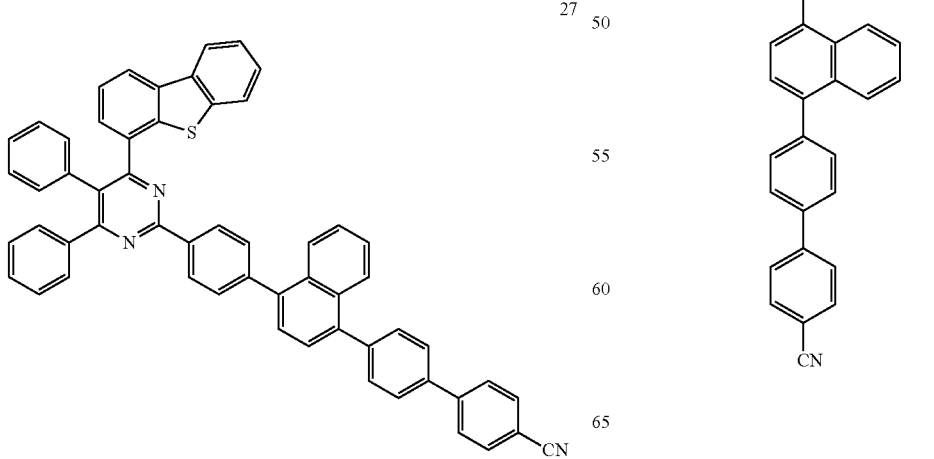
108
-continued
28
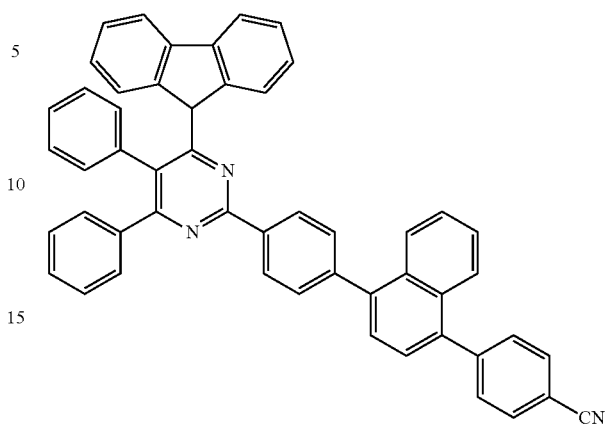

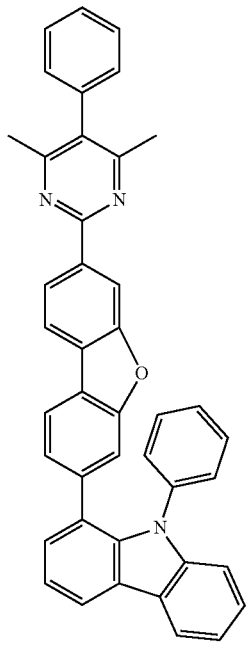
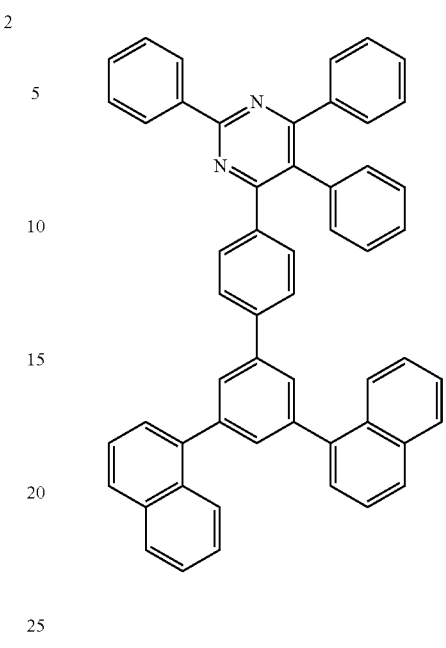
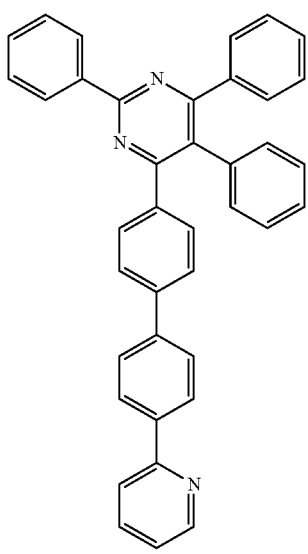
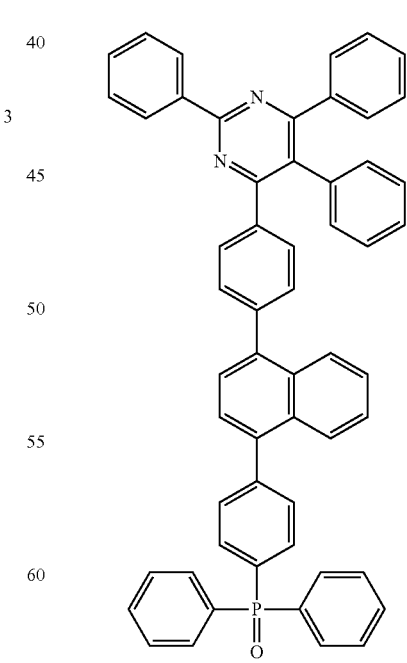

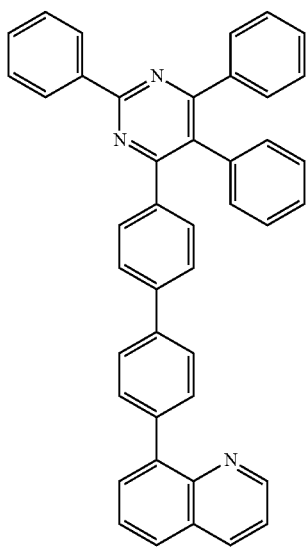
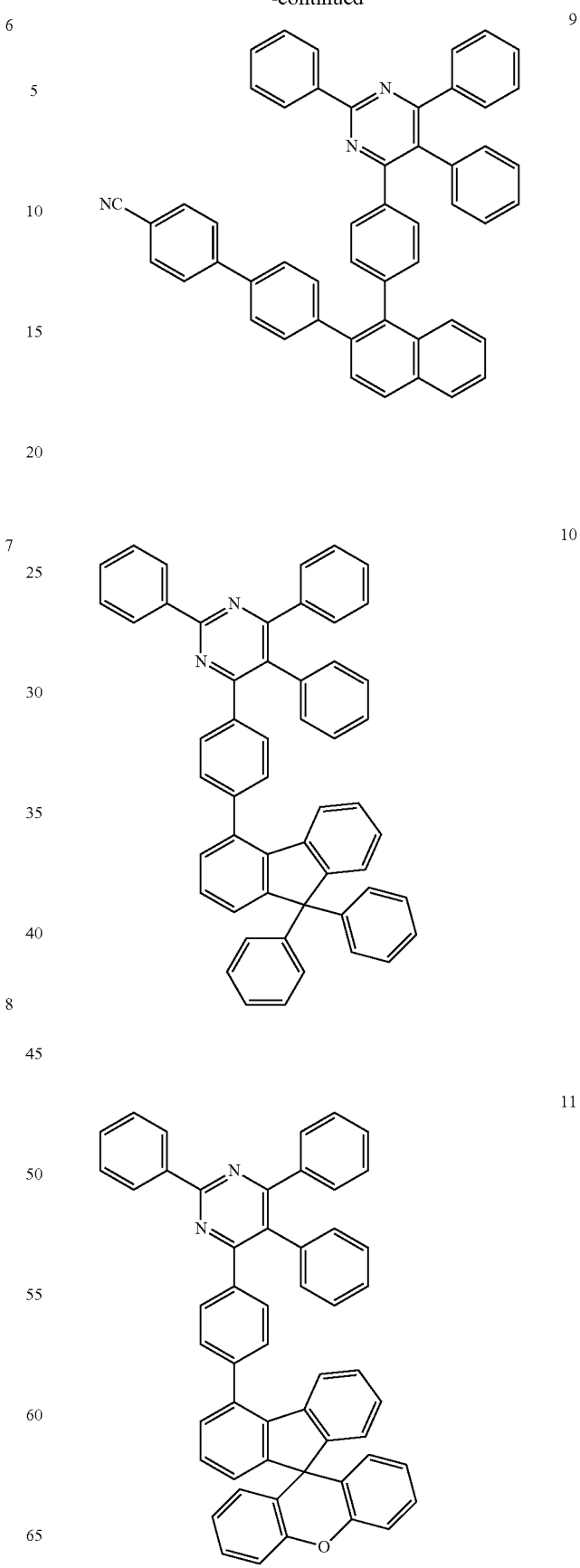

12
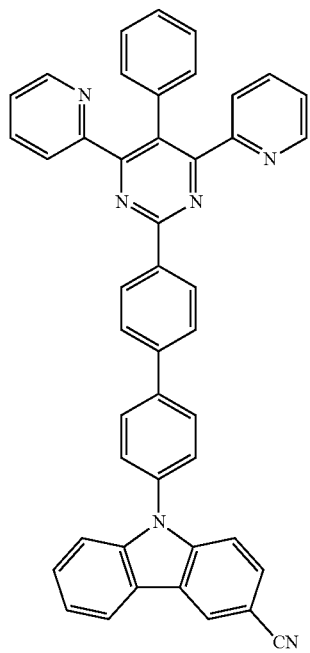
13
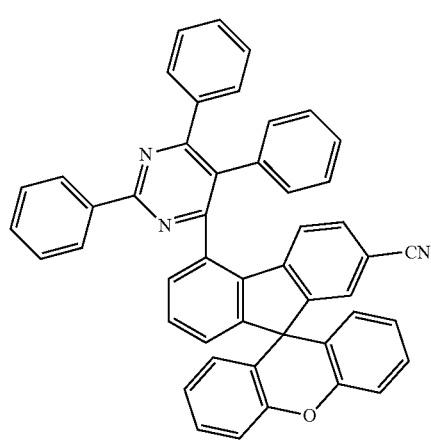
14
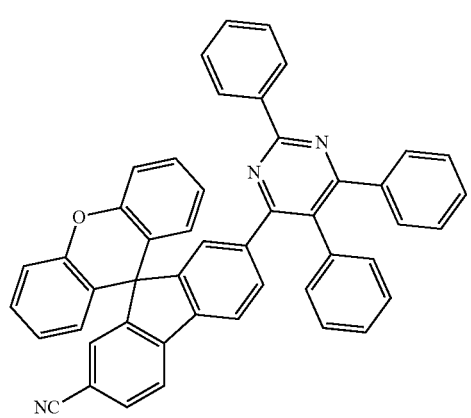
15
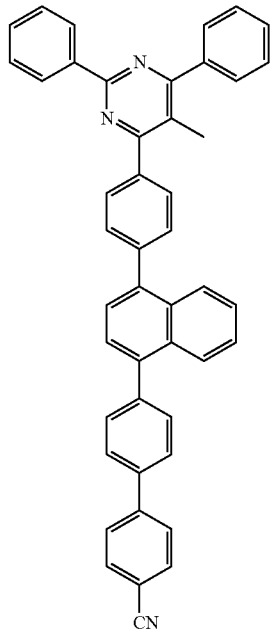
16
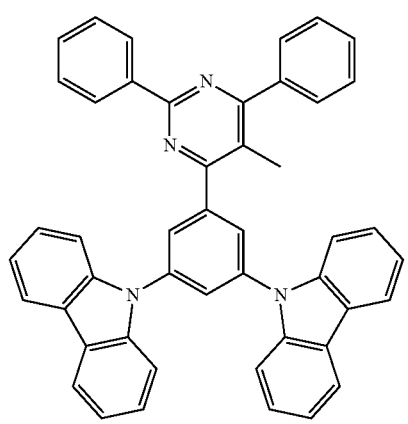

17
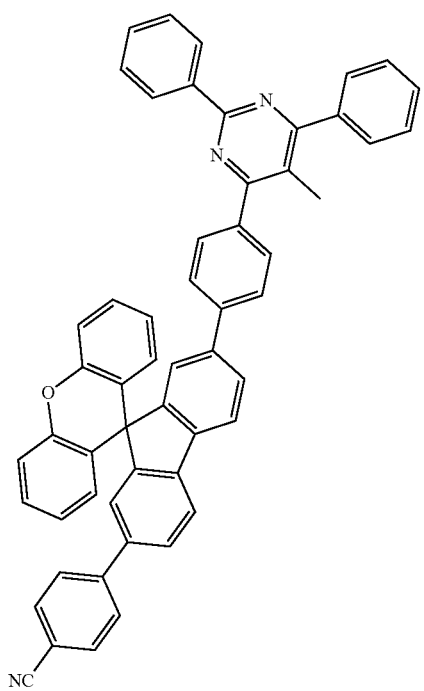
18
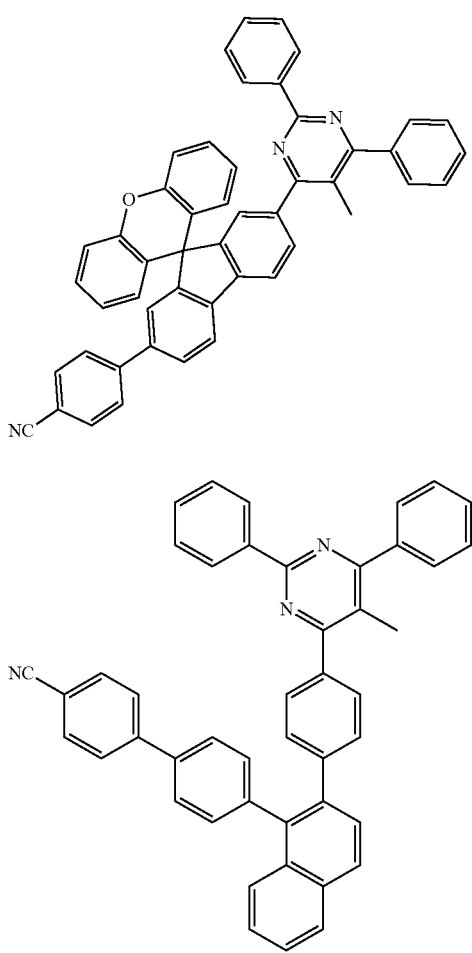
19
20
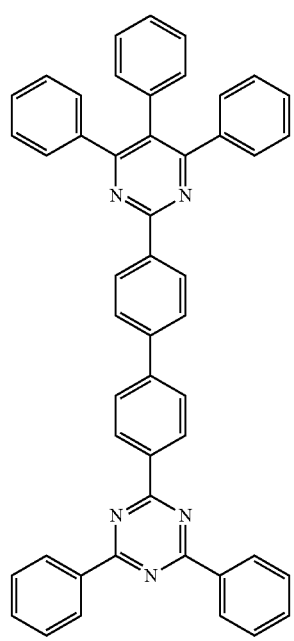
21
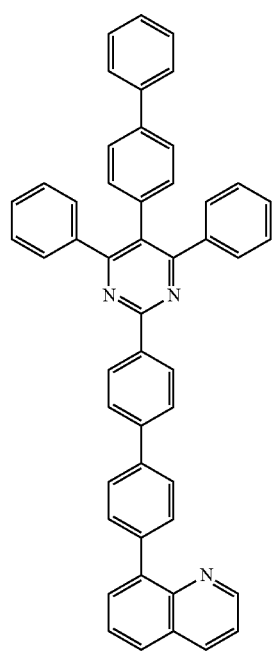

117
-continued
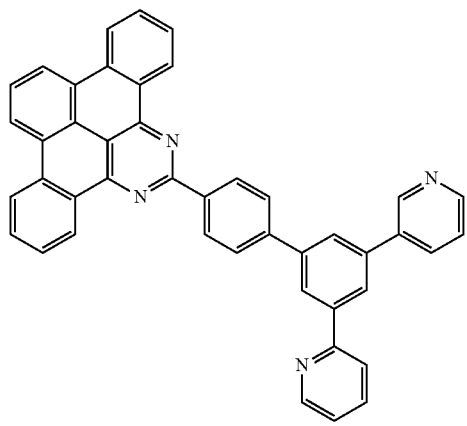
22
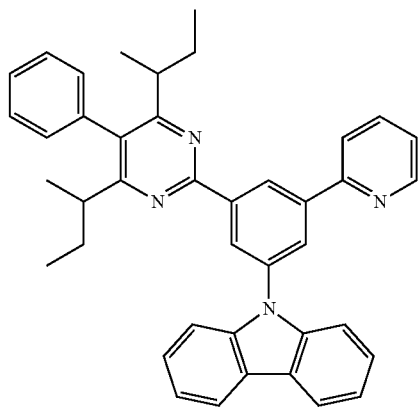
25
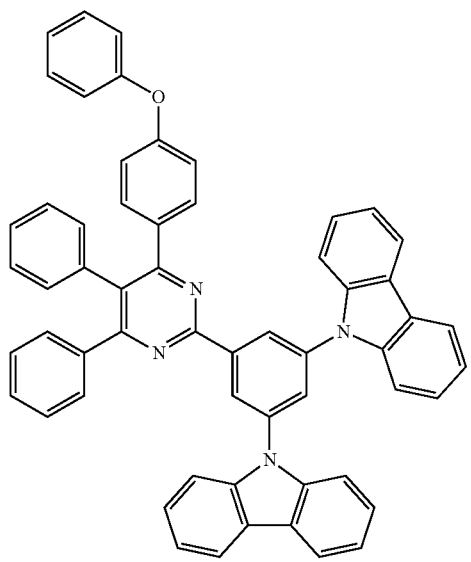
23
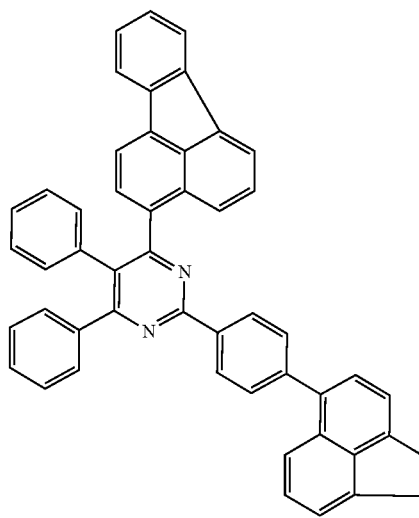
26
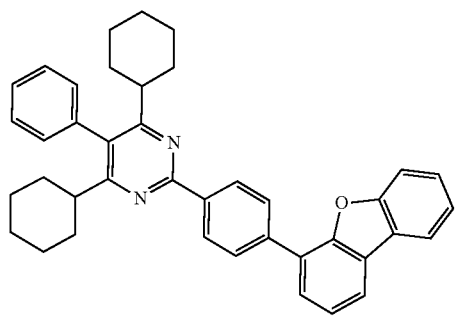
24
118
-continued
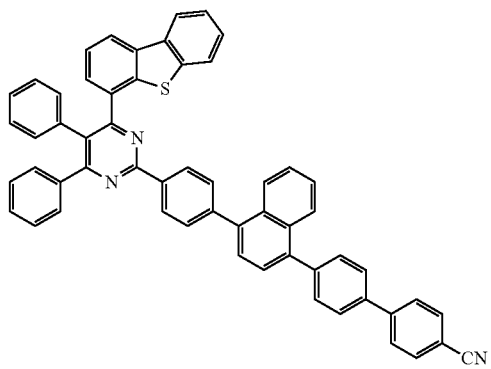
27

28
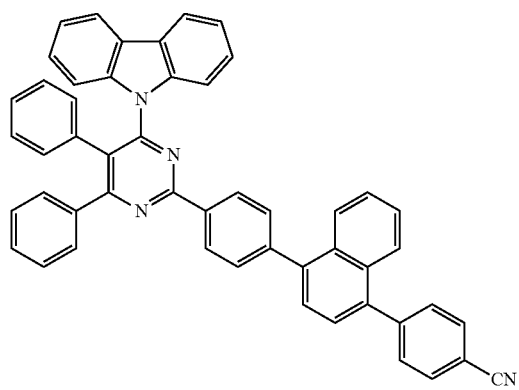
ET1
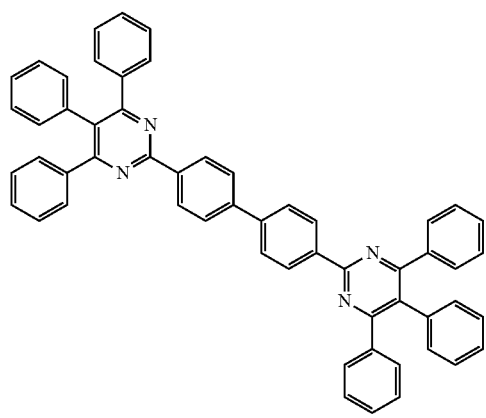
ET2
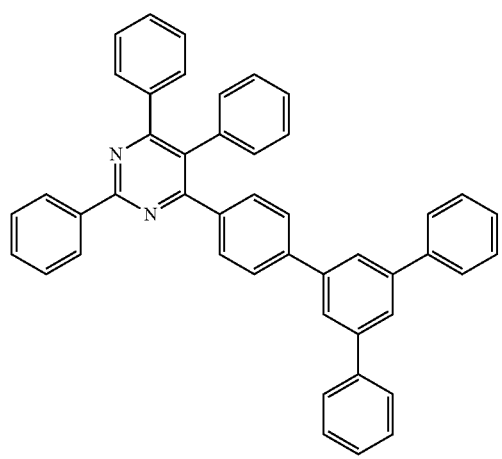
ET3
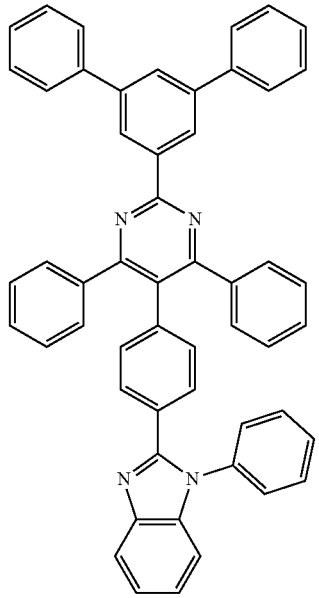
ET4
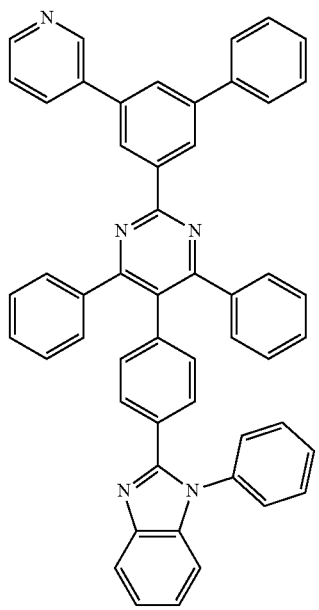

ET5

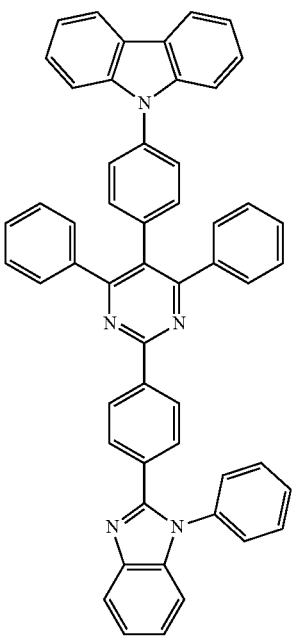

ET6

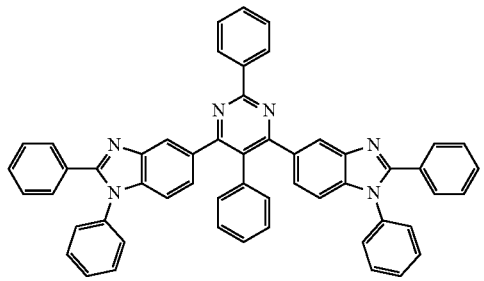

For each of the manufactured organic light emitting devices, driving voltage and light emission efficiency were measured at current density of 10 mA/cm², and the time taken for luminance becoming 98% with respect to initial luminance (LT98) was measured at current density of 20 mA/cm². The results are shown in the following Table 1.

TABLE 1

| Category | Compound | Voltage (V) | Current Efficiency (cd/A) | Color Coordinate (x, y) | LT98 (h) |
| --- | --- | --- | --- | --- | --- |
| Example 1-1 | 1 | 4.01 | 4.81 | (0.138, 0.125) | 75 |
| Example 1-2 | 2 | 3.87 | 4.85 | (0.138, 0.124) | 80 |
| Example 1-3 | 3 | 3.98 | 4.99 | (0.138, 0.126) | 61 |
| Example 1-4 | 4 | 3.97 | 4.85 | (0.138, 0.129) | 66 |
| Example 1-5 | 5 | 4.10 | 4.77 | (0.138, 0.125) | 81 |
| Example 1-6 | 6 | 3.87 | 5.12 | (0.138, 0.124) | 54 |
| Example 1-7 | 7 | 4.01 | 4.91 | (0.138, 0.126) | 64 |
| Example 1-8 | 8 | 4.07 | 4.79 | (0.138, 0.125) | 79 |
| Example 1-9 | 9 | 3.85 | 5.10 | (0.138, 0.126) | 66 |
| Example 1-10 | 10 | 4.00 | 5.19 | (0.139, 0.126) | 60 |
| Example 1-11 | 11 | 3.99 | 5.18 | (0.138, 0.126) | 61 |
| Example 1-12 | 12 | 4.08 | 4.87 | (0.138, 0.129) | 82 |
| Example 1-13 | 13 | 4.08 | 4.88 | (0.138, 0.125) | 77 |
| Example 1-14 | 14 | 4.04 | 4.95 | (0.138, 0.126) | 75 |
| Example 1-15 | 15 | 3.90 | 5.16 | (0.138, 0.125) | 68 |
| Example 1-16 | 16 | 3.98 | 5.18 | (0.138, 0.125) | 61 |
| Example 1-17 | 17 | 3.97 | 5.22 | (0.138, 0.129) | 65 |
| Example 1-18 | 18 | 4.00 | 5.15 | (0.138, 0.127) | 67 |
| Example 1-19 | 19 | 3.85 | 5.12 | (0.138, 0.124) | 59 |

TABLE 1-continued

| Category | Compound | Voltage (V) | Current Efficiency (cd/A) | Color Coordinate (x, y) | LT98 (h) |
| --- | --- | --- | --- | --- | --- |
| Example 1-20 | 20 | 4.11 | 4.99 | (0.138, 0.129) | 79 |
| Example 1-21 | 21 | 3.95 | 5.07 | (0.138, 0.127) | 60 |
| Example 1-22 | 22 | 4.10 | 4.85 | (0.138, 0.125) | 78 |
| Example 1-23 | 23 | 3.98 | 5.01 | (0.138, 0.126) | 70 |
| Example 1-24 | 24 | 3.98 | 4.94 | (0.138, 0.126) | 60 |
| Example 1-25 | 25 | 3.81 | 5.14 | (0.138, 0.126) | 55 |
| Example 1-26 | 26 | 4.09 | 5.01 | (0.138, 0.129) | 75 |
| Example 1-27 | 27 | 4.06 | 4.78 | (0.138, 0.125) | 73 |
| Example 1-28 | 28 | 4.08 | 4.80 | (0.138, 0.125) | 75 |
| Comparative Example 1-1 | ET1 | 4.31 | 4.19 | (0.139, 0.129) | 38 |
| Comparative Example 1-2 | ET2 | 4.12 | 4.60 | (0.138, 0.129) | 19 |
| Comparative Example 1-3 | ET3 | 4.24 | 4.45 | (0.138, 0.127) | 35 |
| Comparative Example 1-4 | ET4 | 4.19 | 4.54 | (0.139, 0.125) | 38 |
| Comparative Example 1-5 | ET5 | 4.34 | 4.26 | (0.139, 0.126) | 39 |
| Comparative Example 1-6 | ET6 | 4.47 | 4.57 | (0.139, 0.125) | 41 |

Based on Table 1, it was identified that the devices including the compound according to one embodiment of the present disclosure had lower driving voltage, higher current efficiency, and, particularly, excellent lifetime properties compared to the devices including ET1 to ET6.

REFERENCE NUMERALS

1: Substrate
2: Anode
3: Hole Injection Layer
4: Hole Transfer Layer
4a: First Hole Transfer Layer
4b: Second Hole Transfer Layer
4c: Third Hole Transfer Layer
4d: Fourth Hole Transfer Layer
4e: Fifth Hole Transfer Layer
4f: Sixth Hole Transfer Layer
4p: p-Doped Hole Transfer Layer
4R: Red Hole Transfer Layer
4G: Green Hole Transfer Layer
4B: Blue Hole Transfer Layer
5: Electron Blocking Layer
6: Light Emitting Layer
6a: First Light Emitting Layer
6b: Second Light Emitting Layer
6c: Third Light Emitting Layer
6BF: Blue Fluorescent Light Emitting Layer
6BFa: First Blue Fluorescent Light Emitting Layer
6BFb: Second Blue Fluorescent Light Emitting Layer
6YGP: Yellow Green Phosphorescent Light Emitting Layer
6RP: Red Phosphorescent Light Emitting Layer
6GP: Green Phosphorescent Light Emitting Layer
7: Hole Blocking Layer
8: Electron Injection and Transfer Layer
9: Electron Transfer Layer
9a: First Electron Transfer Layer
9b: Second Electron Transfer Layer
9c: Third Electron Transfer Layer
10: Electron Injection Layer
11: Cathode
12: N-Type Charge Generating Layer 12a: First N-Type Charge Generating Layer
12b: Second N-Type Charge Generating Layer
13: P-Type Charge Generating Layer
13a: First P-Type Charge Generating Layer
13b: Second P-Type Charge Generating Layer
14: Capping Layer

The invention claimed is:
1. A compound of Chemical Formula 1:

Chemical Formula 1

HAr-L1-L2-Ar1 wherein, in Chemical Formula 1:

HAr represents Chemical Formula A-1 or A-2;

L1 and L2 are selected from among a phenylene group that is unsubstituted or substituted with an aryl group substituted with a cyano group, an aryl group substituted with a fluoroalkoxy group, a heteroaryl group substituted with an alkyl group, an aryl group, or a heteroaryl group; a biphenylene group; a divalent naphthyl group that is unsubstituted or substituted with a cyano group; a divalent fluorenyl group that is unsubstituted or substituted with an alkyl group or an aryl group; a divalent dibenzofuranyl group; a divalent dibenzothiophenyl group; a divalent carbazolyl group that is unsubstituted or substituted with an aryl group, a heteroaryl group, or an arylheteroaryl group; and a divalent spirofluorenexanthenyl group; or one of L1 and L2 is a phenylene group that is unsubstituted or substituted with an aryl group substituted with a cyano group, an aryl group substituted with a fluoroalkoxy group, a heteroaryl group substituted with an alkyl group, an aryl group, or a heteroaryl group; a biphenylene group; a divalent naphthyl group that is unsubstituted or substituted with a cyano group; a divalent fluorenyl group that is unsubstituted or substituted with an alkyl group or an aryl group; a divalent dibenzofuranyl group; a divalent dibenzothiophenyl group; a divalent carbazolyl group that is unsubstituted or substituted with an aryl group, a heteroaryl group, or an arylheteroaryl group; or a divalent spirofluorenexanthenyl group, and the other one is a direct bond;

Ar1 is a cyano group; a phenyl group that is unsubstituted or substituted with a cyano group, an arylphosphine oxide group, an aryl group substituted with a fluoroalkoxy group, an aryl group, or a heteroaryl group; a biphenyl group that is unsubstituted or substituted with a cyano group; a naphthyl group that is unsubstituted or substituted with a cyano group; a fluoranthenyl group; a fluorenyl group that is unsubstituted or substituted with an alkyl group or an aryl group; a triphenylenyl group; a spiro[fluorene-9,9'-xanthen]yl group that is unsubstituted or substituted with a cyano group; a pyridinyl group that is unsubstituted or substituted with an alkyl group; a triazinyl group that is unsubstituted or substituted with an alkyl group or an aryl group; a quinolinyl group; an indenocarbazolyl group that is unsubstituted or substituted with an alkyl group; a beta-carbolinyl group; a pyridoindolyl group; a benzothienopyrimidinyl group that is unsubstituted or substituted with an aryl group; a benzimidazolyl group that is unsubstituted or substituted with an aryl group; a benzoxazolyl group; a benzothiazolyl group; a dibenzofuranyl group; a dibenzothiophenyl group; a carbazolyl group that is unsubstituted or substituted with a cyano group or an aryl group; or a phenanthrolinyl group;

with the proviso that at least one of L1 and L2 is a biphenylene group; a divalent naphthyl group that is unsubstituted or substituted with a cyano group; a divalent fluorenyl group that is unsubstituted or substituted with an alkyl group or an aryl group; a divalent dibenzofuranyl group; a divalent dibenzothiophenyl group; a divalent carbazolyl group that is unsubstituted or substituted with an aryl group, a heteroaryl group, or an arylheteroaryl group; or a divalent spirofluorenexanthenyl group; or Ar1 is a cyano group; a biphenyl group that is unsubstituted or substituted with a cyano group; a naphthyl group that is unsubstituted or substituted with a cyano group; a fluoranthenyl group; a fluorenyl group that is unsubstituted or substituted with an alkyl group or an aryl group; a triphenylenyl group; a spiro[fluorene-9,9'-xanthen]yl group that is unsubstituted or substituted with a cyano group; a pyridinyl group that is unsubstituted or substituted with an alkyl group; a triazinyl group that is unsubstituted or substituted with an alkyl group or an aryl group; a quinolinyl group; an indenocarbazolyl group that is unsubstituted or substituted with an alkyl group; a beta-carbolinyl group; a pyridoindolyl group; a benzothienopyrimidinyl group that is unsubstituted or substituted with an aryl group; a benzimidazolyl group that is unsubstituted or substituted with an aryl group; a benzoxazolyl group; a benzothiazolyl group; a dibenzofuranyl group; a dibenzothiophenyl group; or a phenanthrolinyl group;

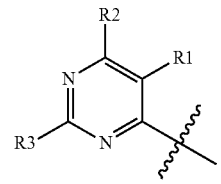

Chemical Formula A-1 wherein in Chemical Formula A-1:
one of R1 to R3 is a phenyl group, and the remaining two are the same as or different from each other and each independently is a substituted or unsubstituted cycloalkyl group, a substituted or unsubstituted branched alkyl group, a methyl group, or a substituted or unsubstituted monocyclic heteroaryl group; or two of R1 to R3 are the same as or different from each other and each independently is a phenyl group that is unsubstituted or substituted with an alkyl group, and the remaining one is a substituted or unsubstituted linear or branched alkyl group; a monocyclic or polycyclic aryl group that is unsubstituted or substituted with an alkyl group, an aryl group or an aryloxy group; a pyridinyl group; a dibenzothiophenyl group; a dibenzofuranyl group; or a carbazolyl group;

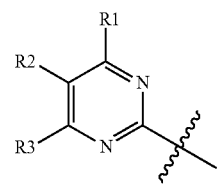

Chemical Formula A-2 wherein in Chemical Formula A-2:
one of R1 to R3 is a phenyl group, and the remaining two are the same as or different from each other and each independently is a substituted or unsubstituted cycloalkyl group, a substituted or unsubstituted branched alkyl group, a methyl group, or a substituted or unsubstituted monocyclic heteroaryl group; or two of R1 to R3 are the same as or different from each other and each independently is a phenyl group that is unsubstituted or substituted with an alkyl group, and the remaining one is a substituted or unsubstituted linear or branched alkyl group; a monocyclic aryl group that is substituted with an alkyl group, an aryl group or an aryloxy group; a polycyclic aryl group that is unsubstituted or substituted with an alkyl group, an aryl group or an aryloxy group; a pyridinyl group; a dibenzothiophenyl group; a dibenzofuranyl group; or a carbazolyl group; or R1 to R3 are each a phenyl group, and the phenyl groups bond to each other so the Chemical Formula A-2 is a tribenzoperimidine ring of the structure:

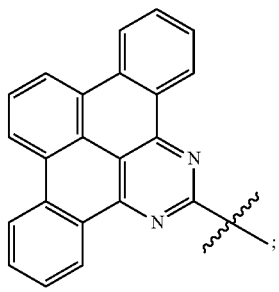 [SMILES: *c1nc2c3ccccc3c3cccc4c5ccccc5c(n1)c2c34]

and

is a site bonding to L1 of Chemical Formula 1.

2. The compound of claim 1, wherein Chemical Formula 1 is one of the following Chemical Formula 1-1 or 1-2:

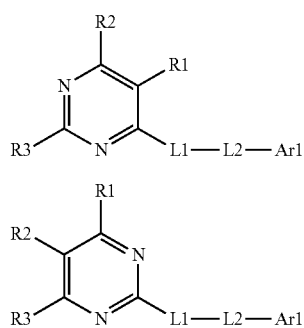

wherein in Chemical Formulae 1-1 and 1-2:
Ar1 has the same definition as in Chemical Formula 1;
one of L1 and L2 is a phenylene group that is unsubstituted or substituted with an aryl group substituted with a cyano group, an aryl group substituted with a fluoroalkoxy group, a heteroaryl group substituted with an alkyl group, an aryl group, or a heteroaryl group; a biphenylene group; a divalent naphthyl group that is unsubstituted or substituted with a cyano group; a divalent fluorenyl group that is unsubstituted or substituted with an alkyl group or an aryl group; a divalent dibenzofuranyl group; a divalent dibenzothiophenyl group; a divalent carbazolyl group that is unsubstituted or substituted with an aryl group, a heteroaryl group, or an arylheteroaryl group; or a divalent spirofluorenexanthenyl group, and the other one is a direct bond; and R1 to R3 have the same definitions as in Chemical Formulae A-1 and A-2.

3. The compound of claim 1, wherein one of R1 to R3 is a phenyl group, and the remaining two are the same as or different from each other and each independently is a cycloalkyl group, a branched alkyl group, a methyl group, or a monocyclic heteroaryl group.

4. A compound selected from among the following compounds:

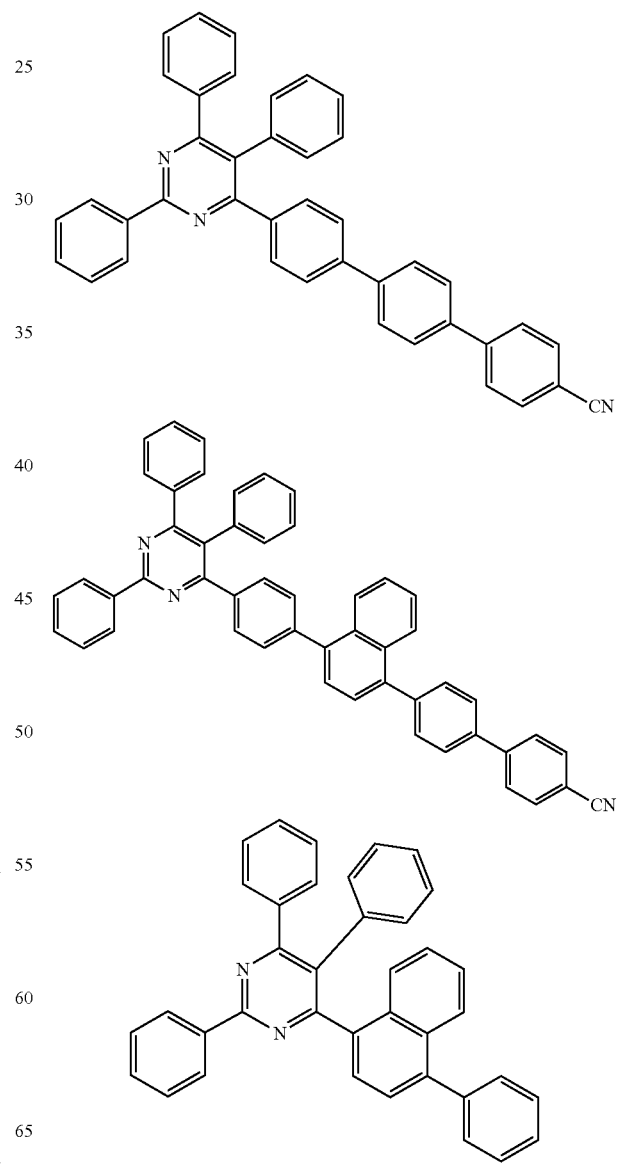

127
-continued
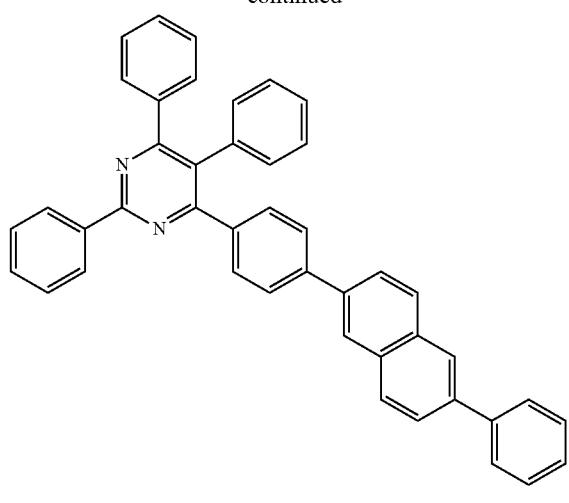
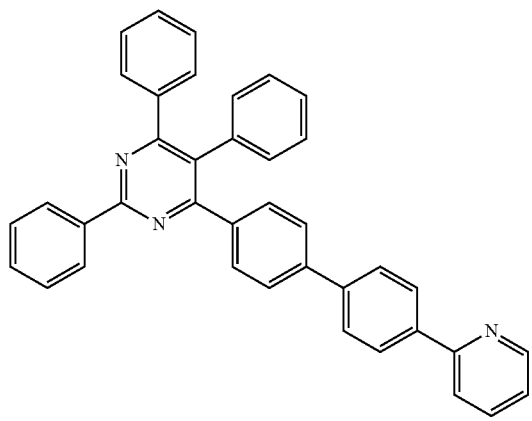
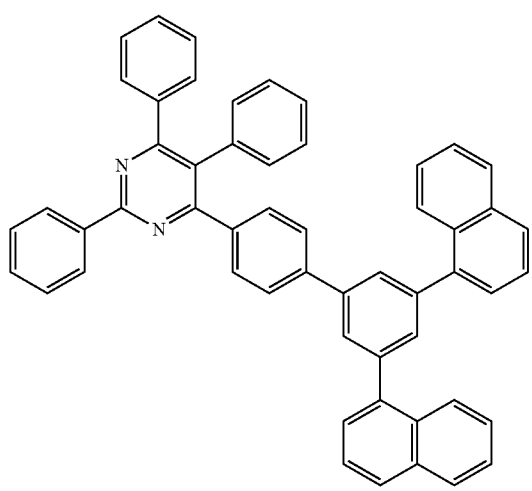
128
-continued
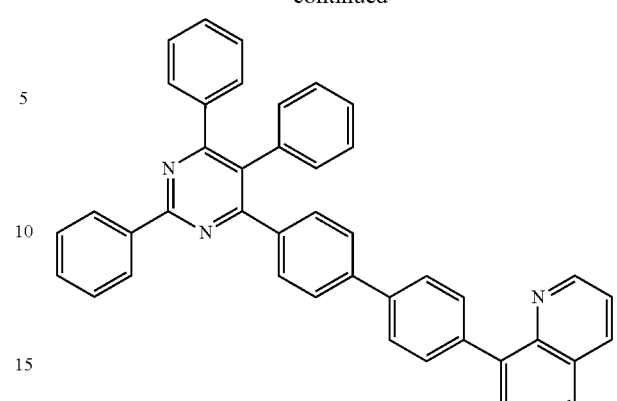
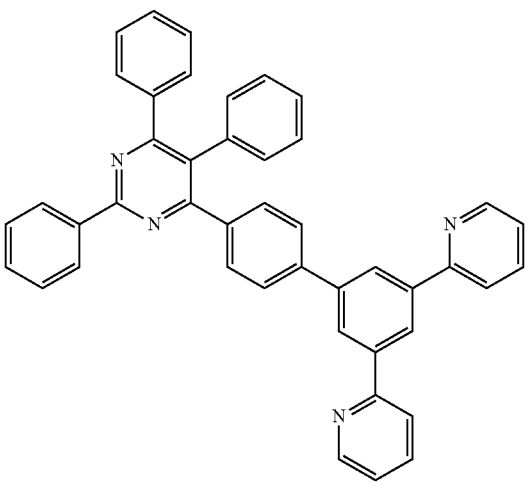
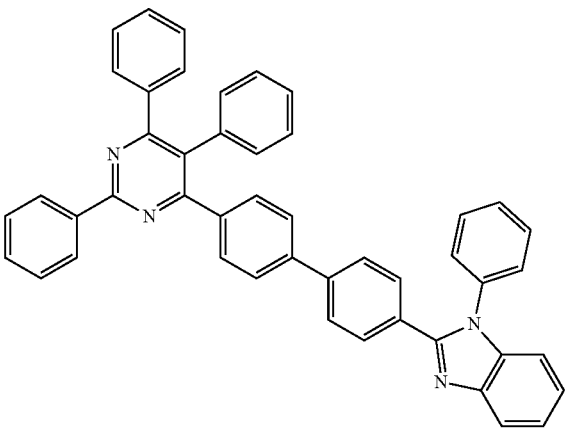

129
-continued
130
-continued
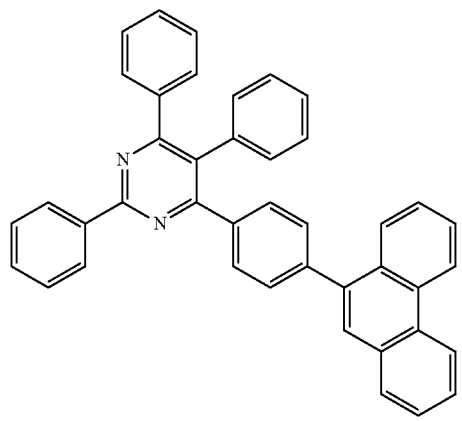
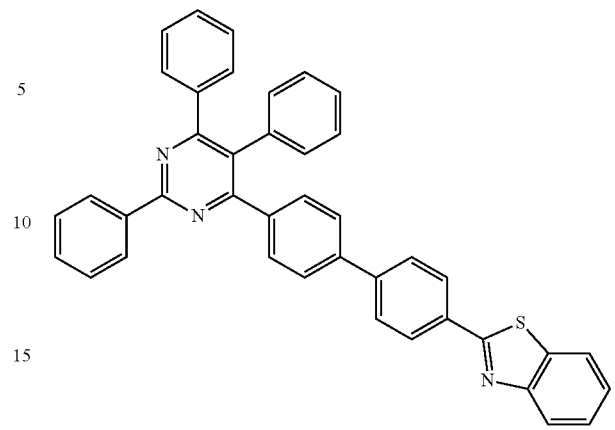
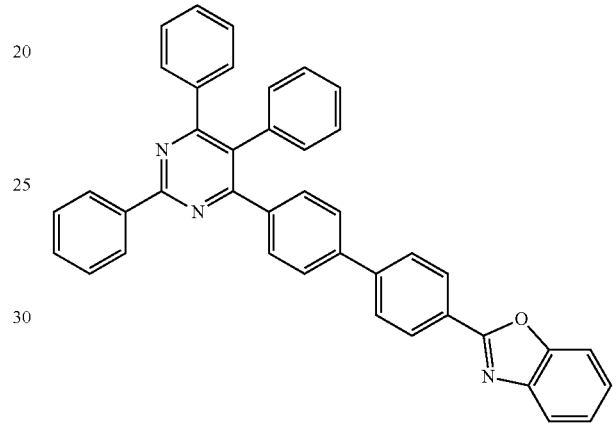
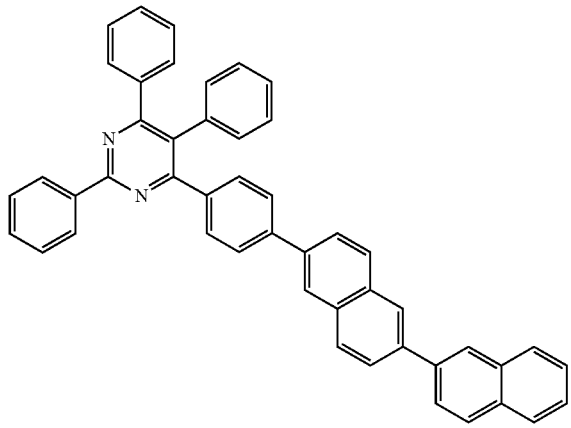
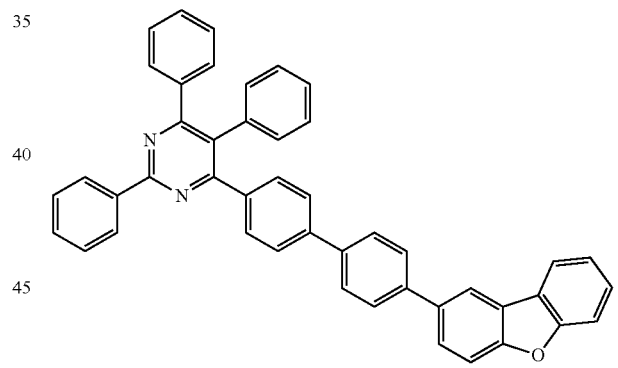
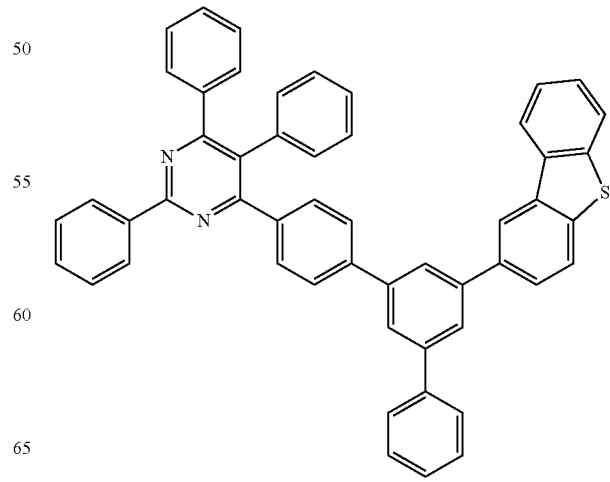

131
-continued
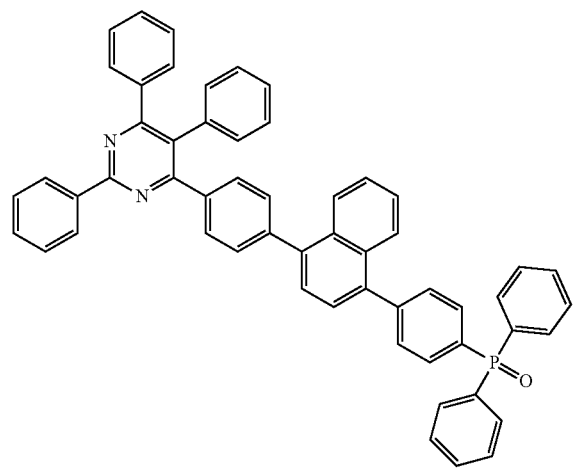
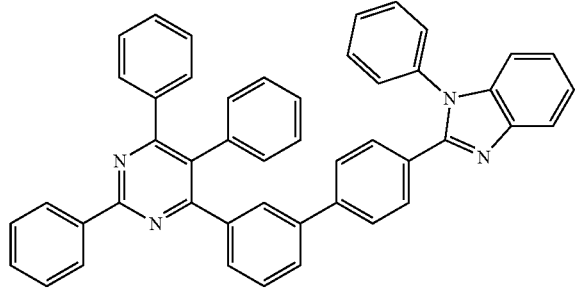
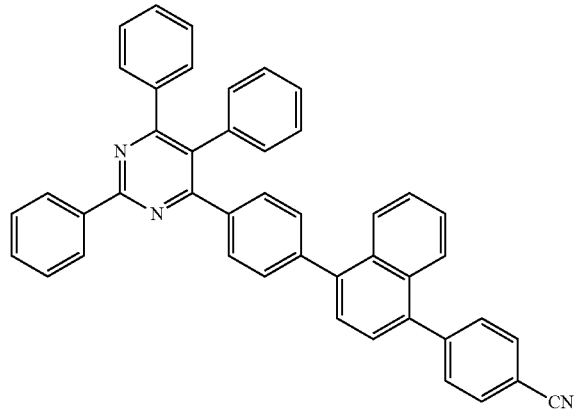
132
-continued
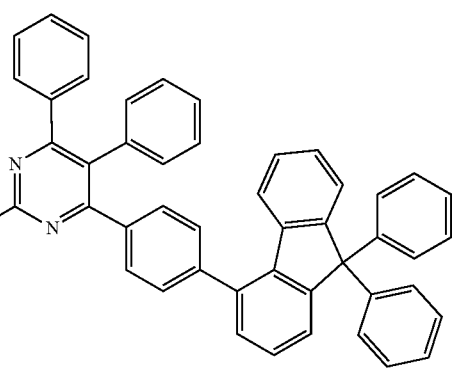
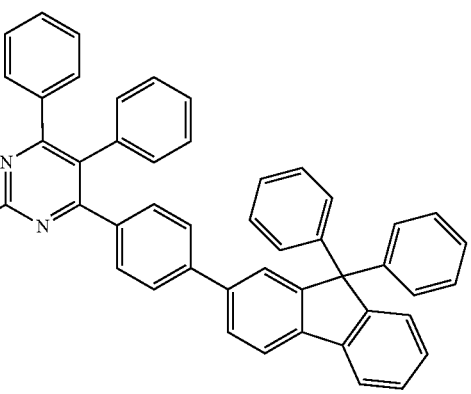
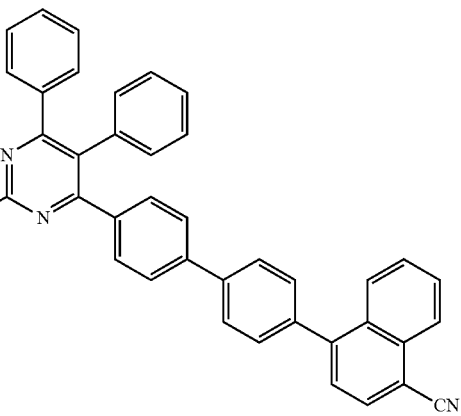
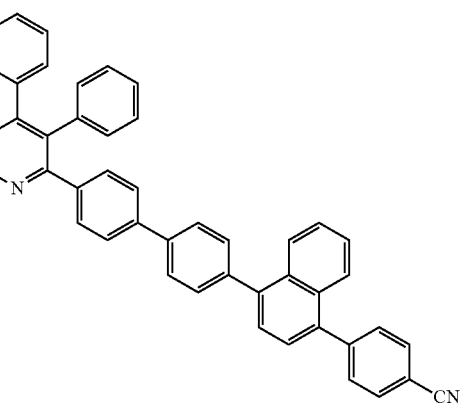

133
-continued
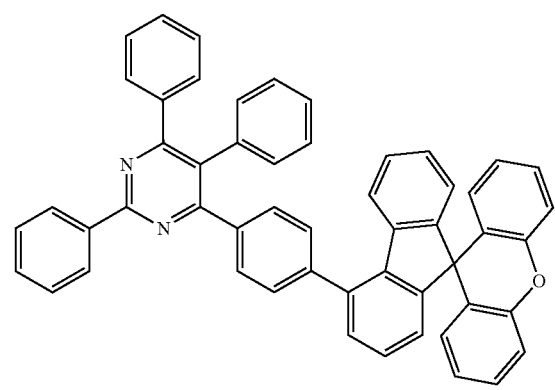
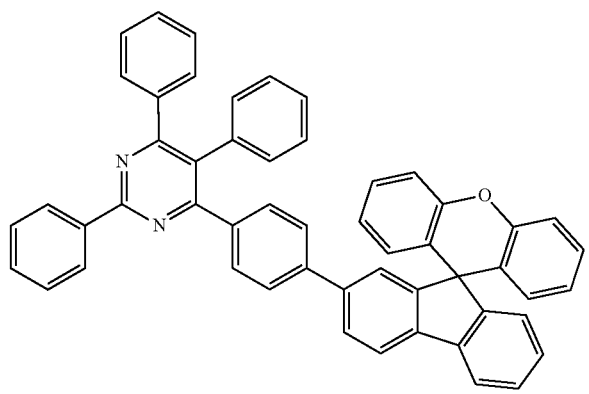
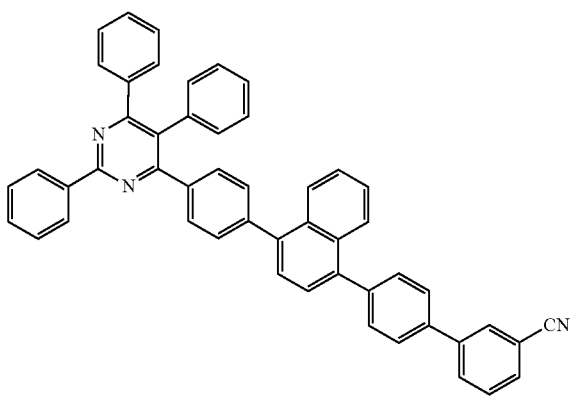
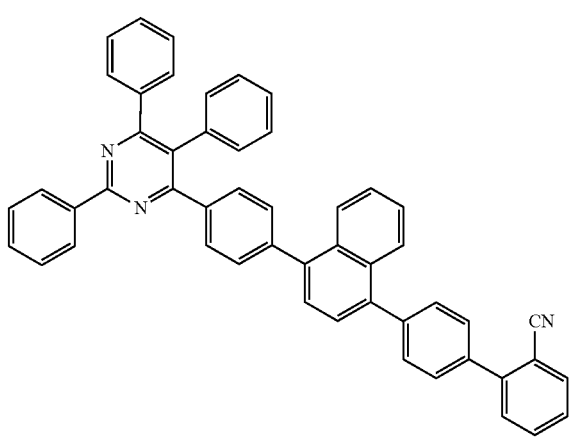
134
-continued
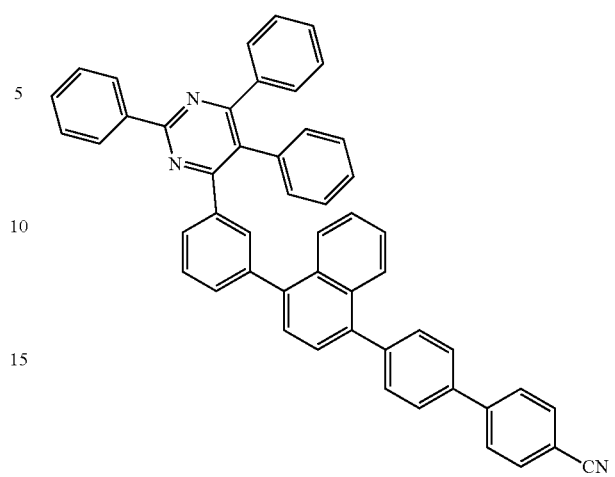
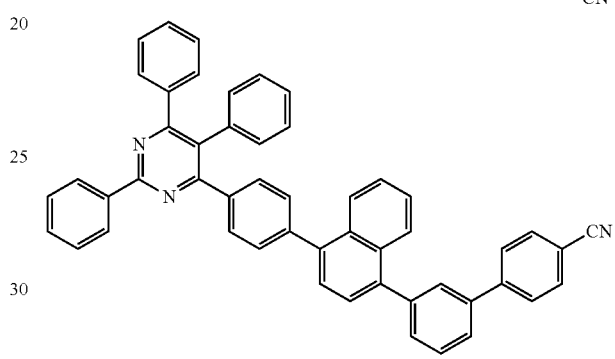
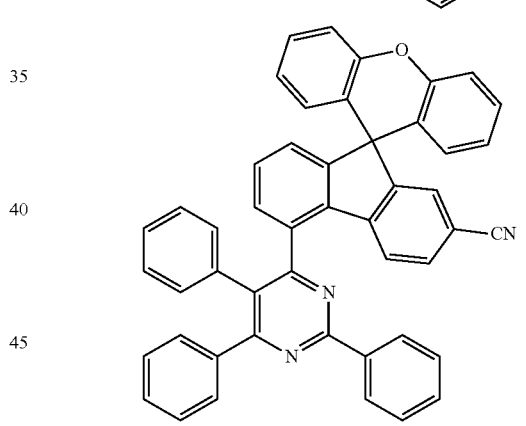
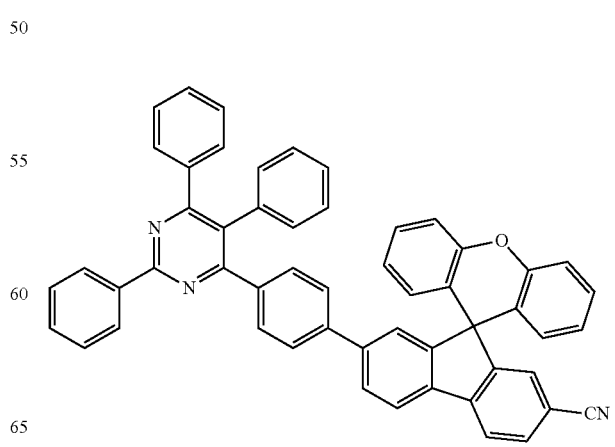

135
-continued
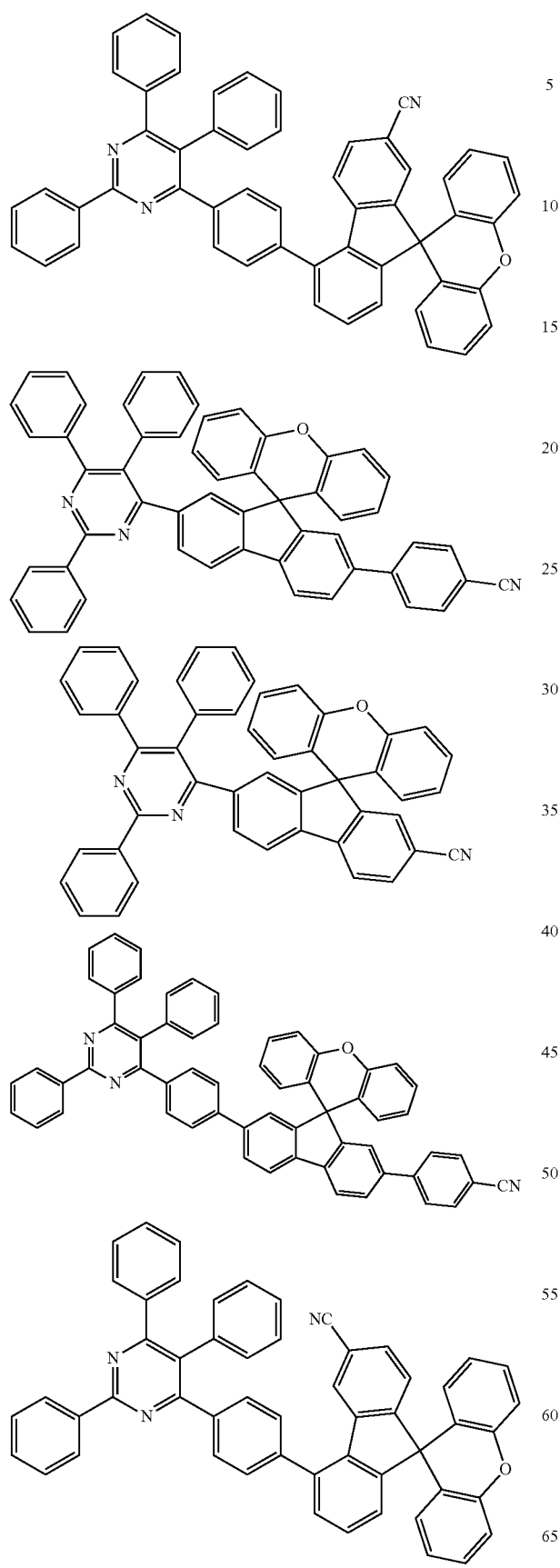
136
-continued
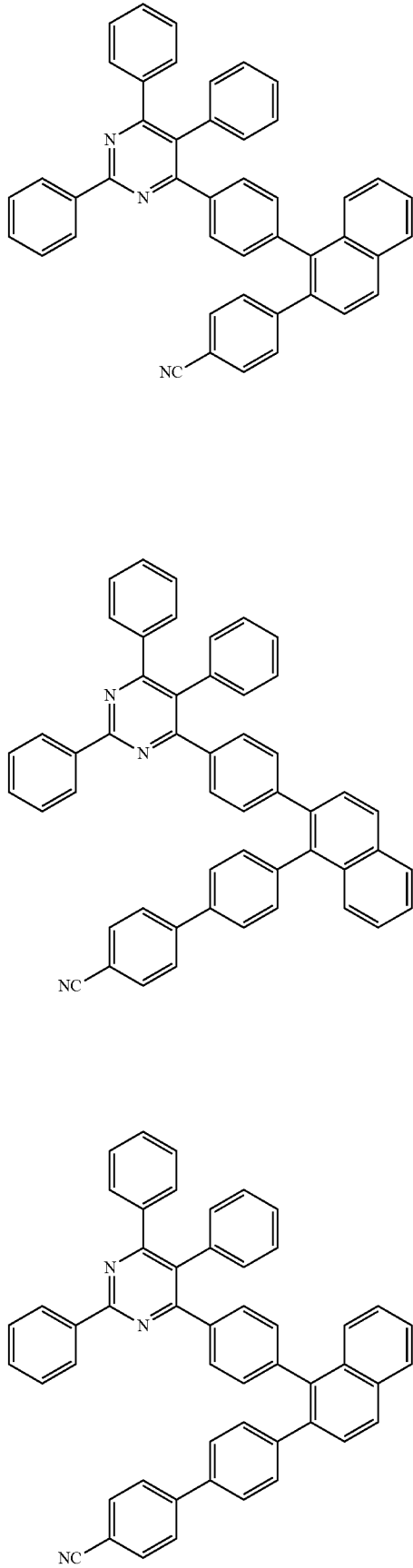

137
-continued
138
-continued
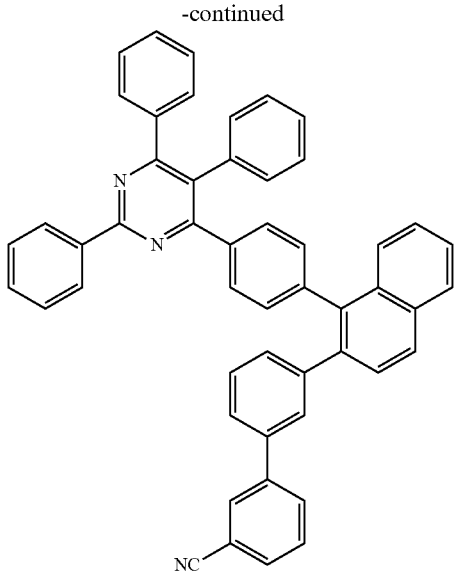
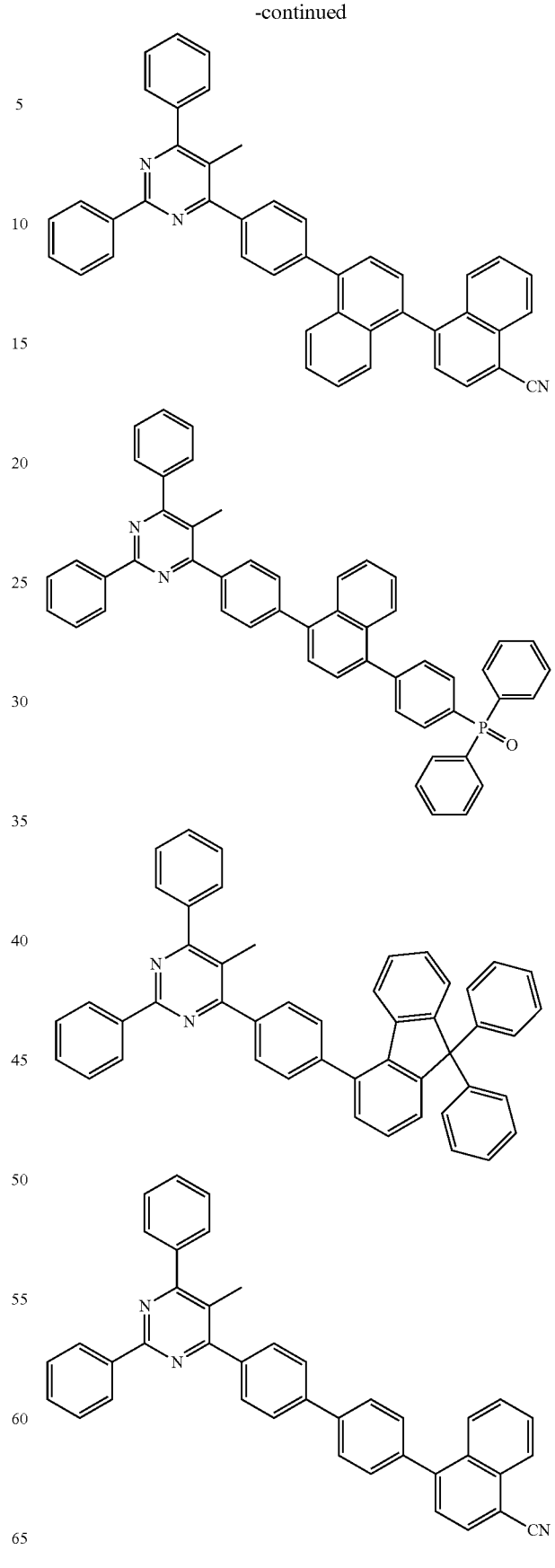

139
-continued
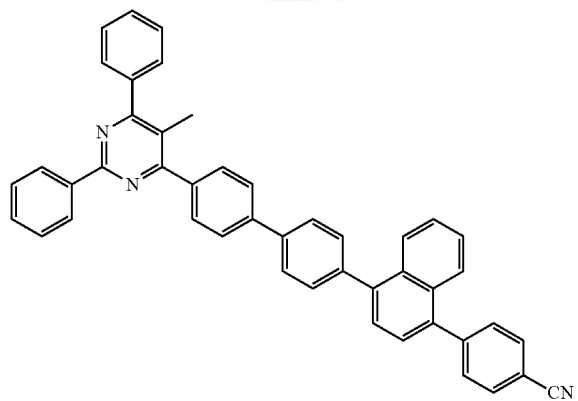
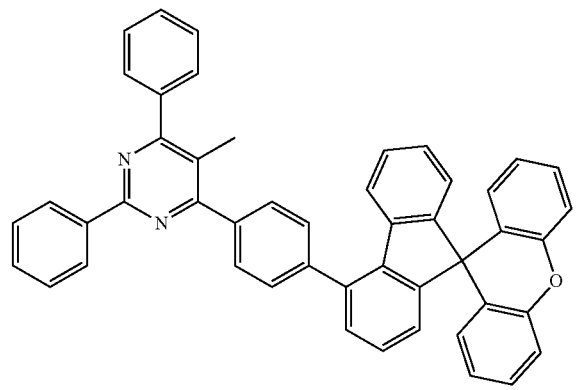
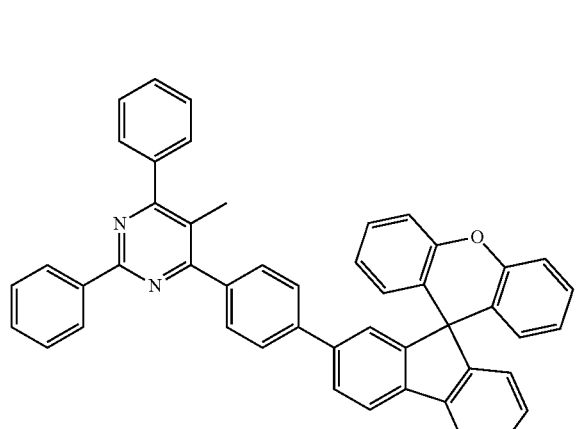
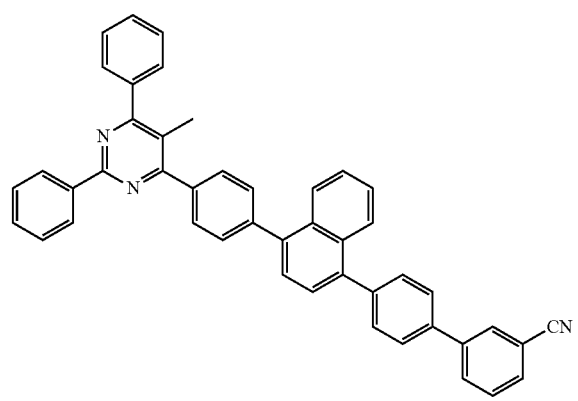
140
-continued
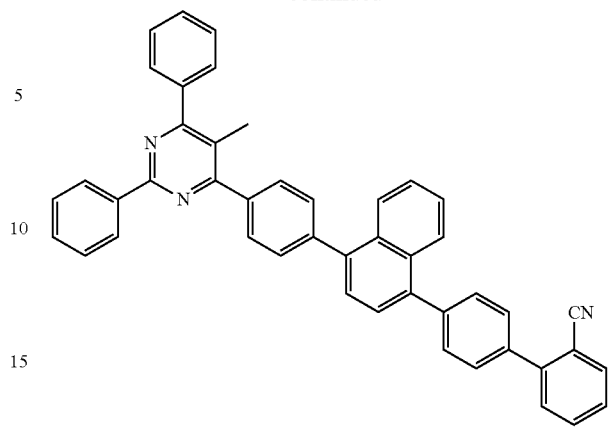
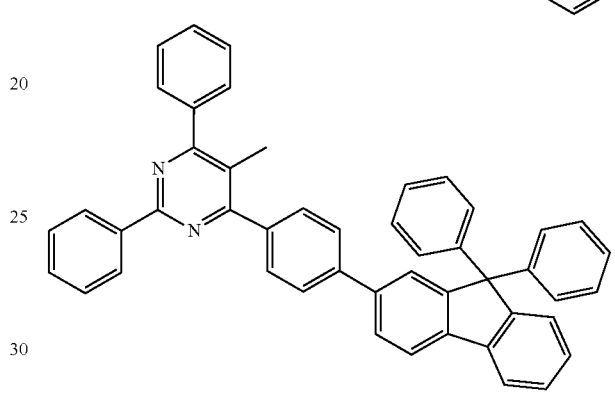
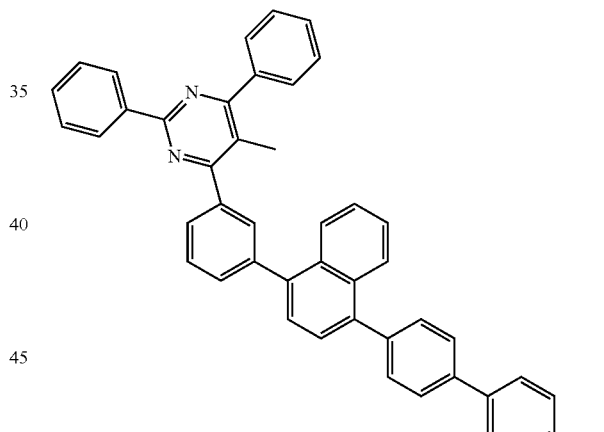
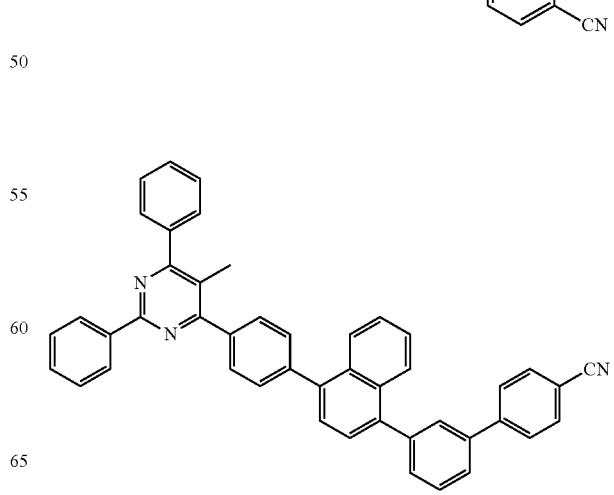

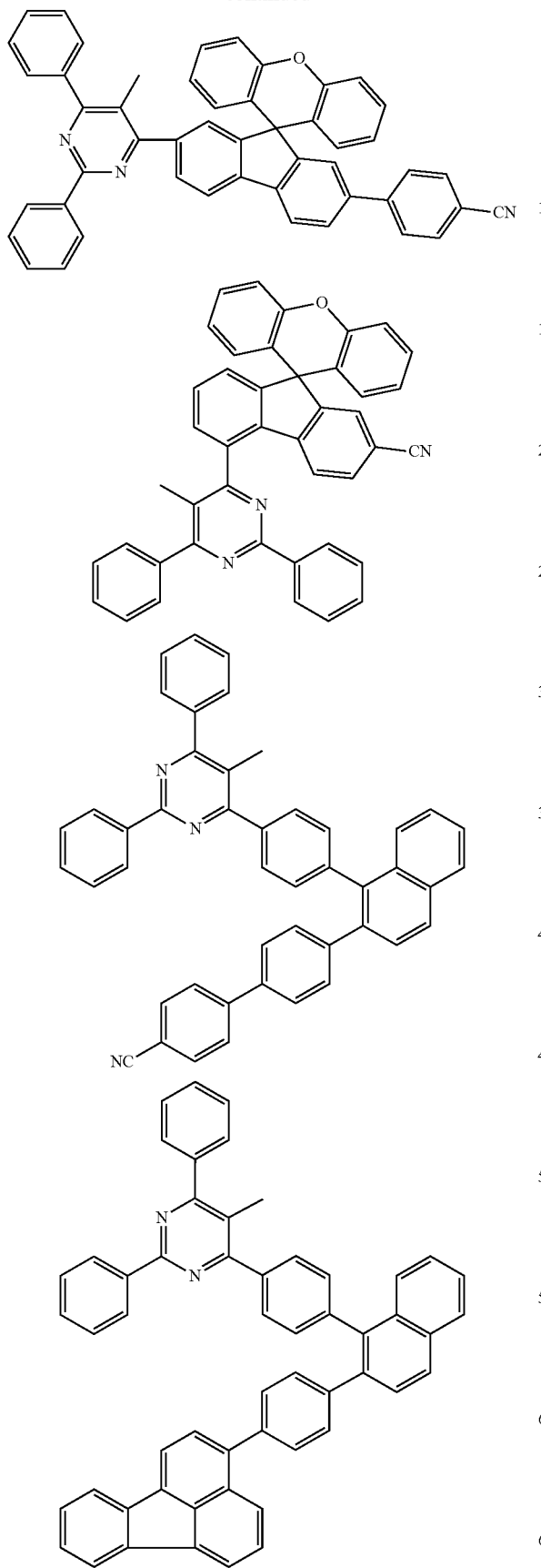
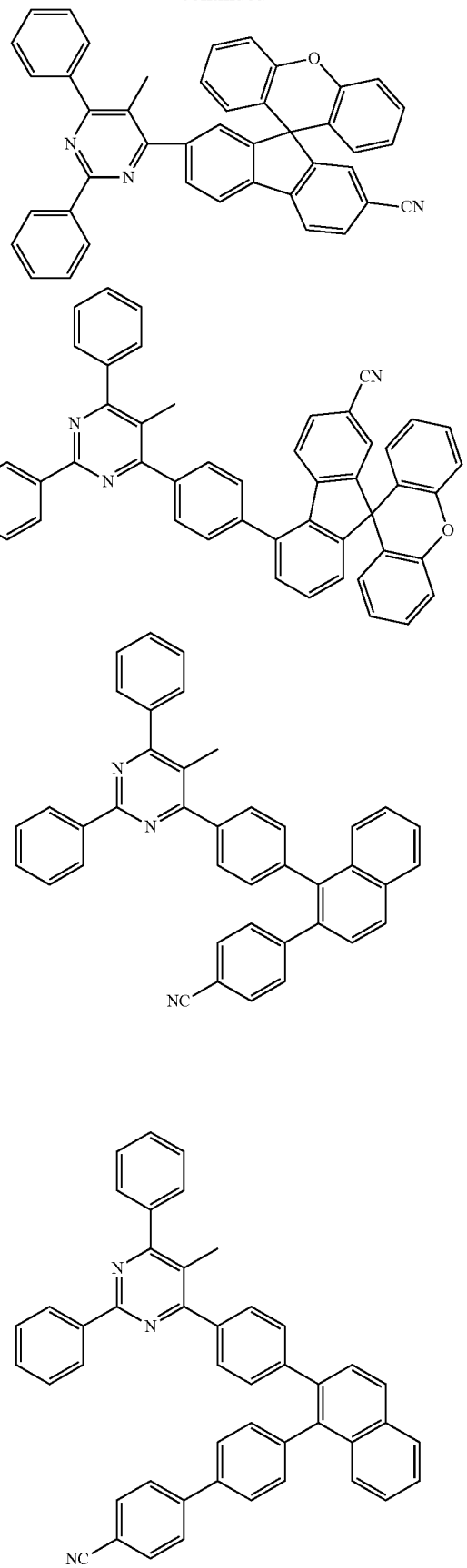

143
-continued
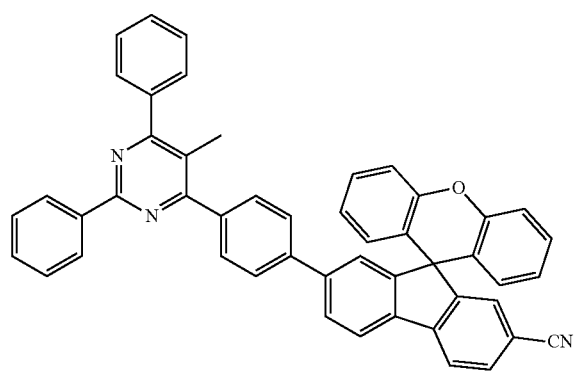
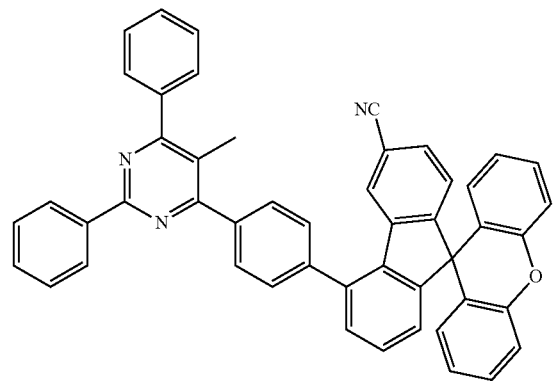
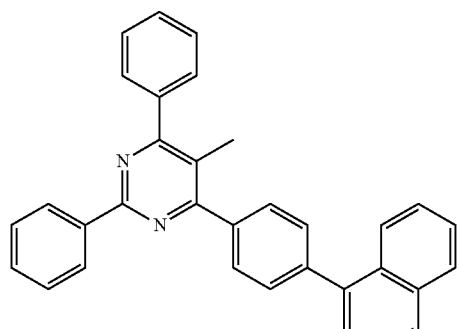
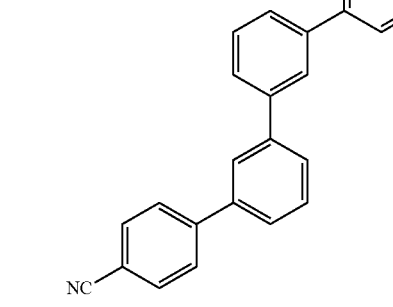
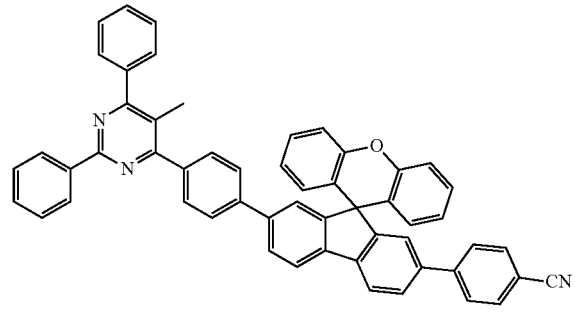
144
-continued
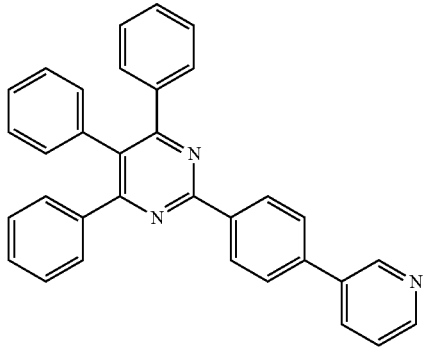
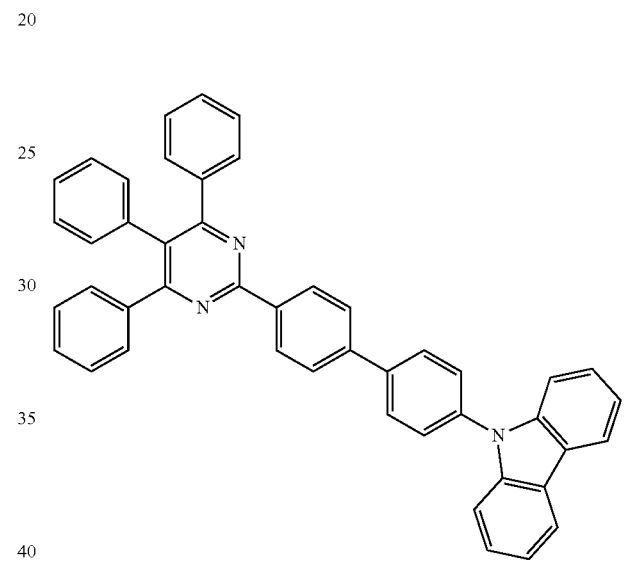
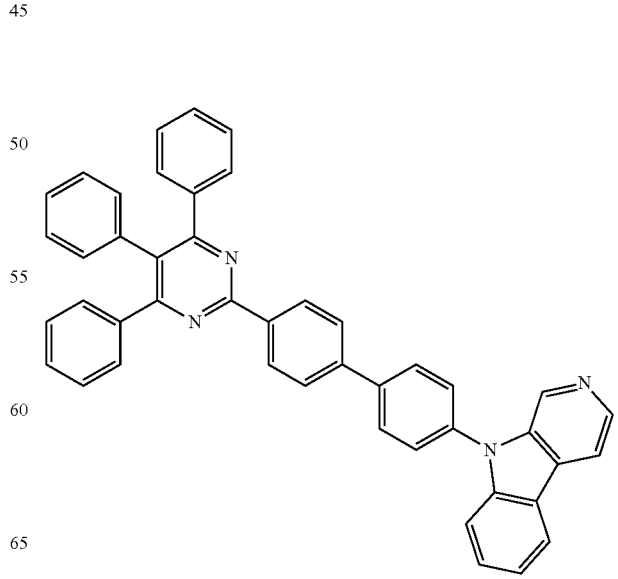

145
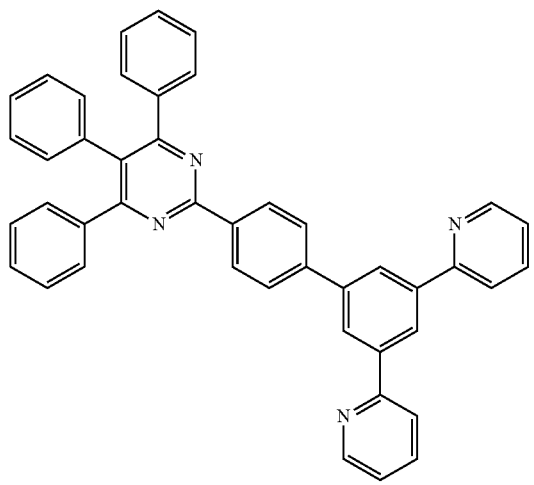
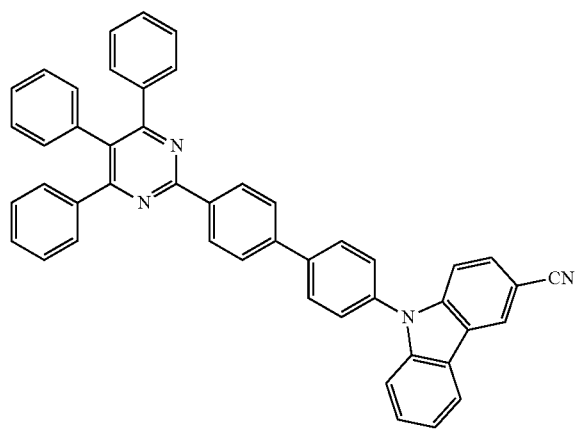
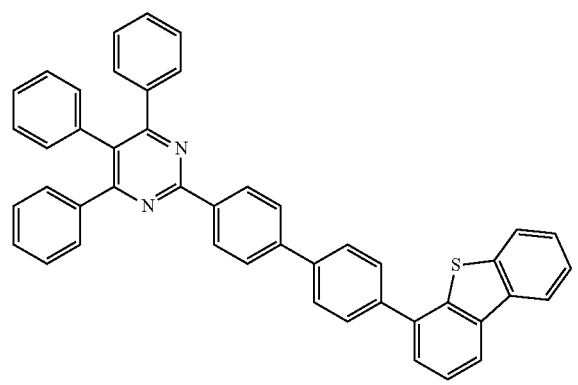
146
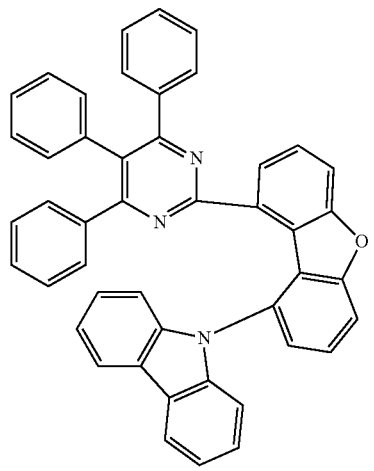
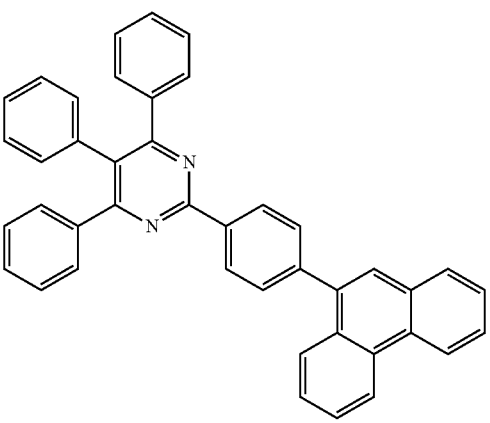

147
-continued
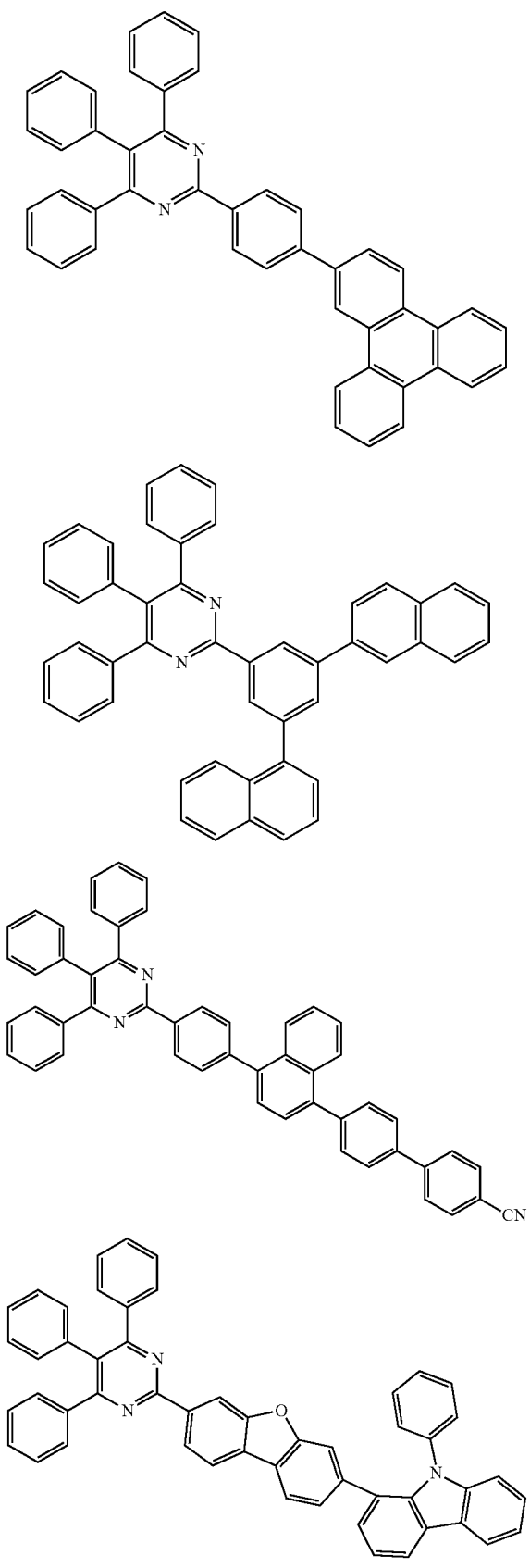
148
-continued
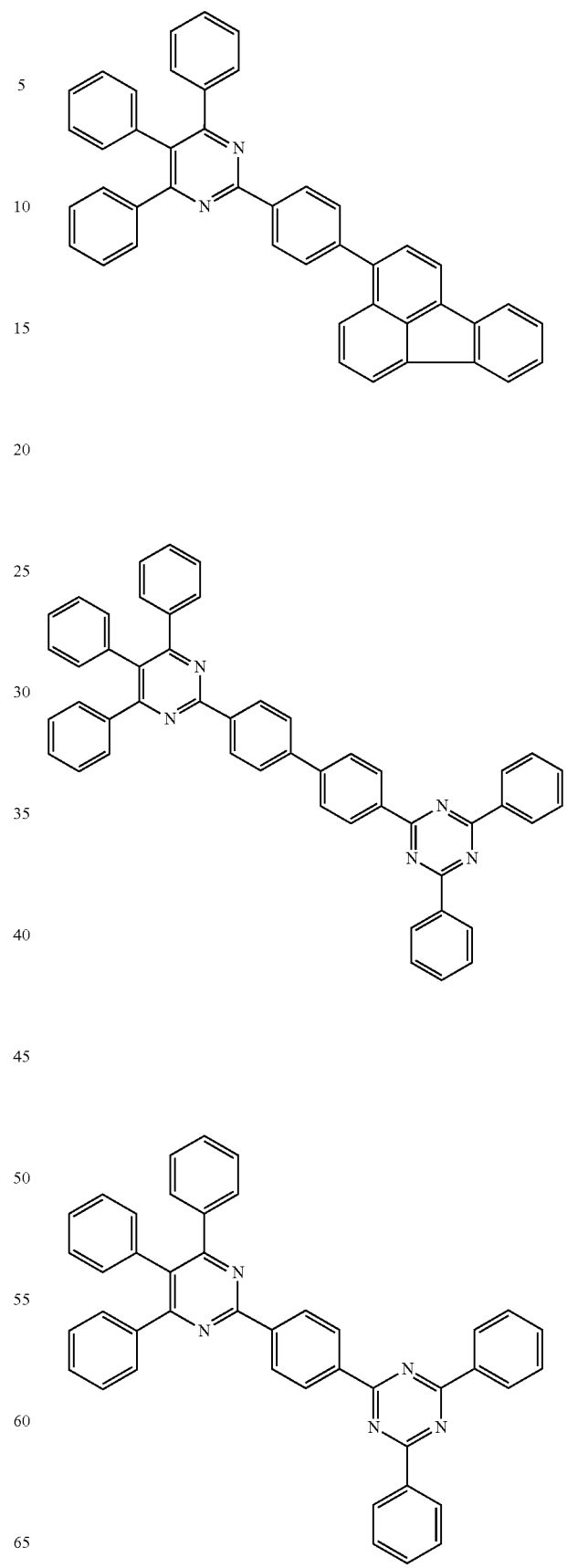

149
-continued
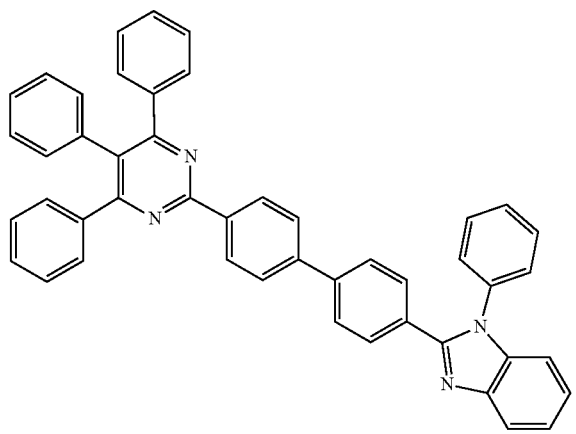
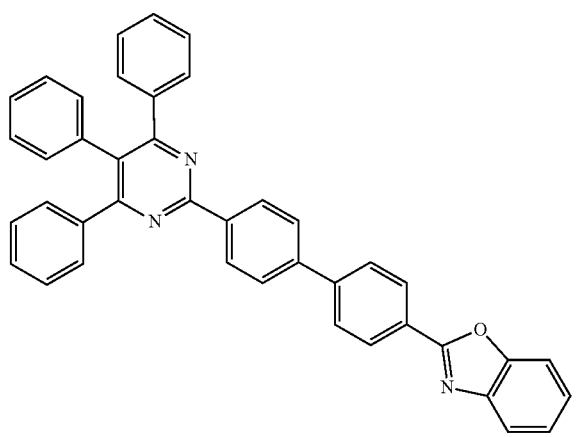
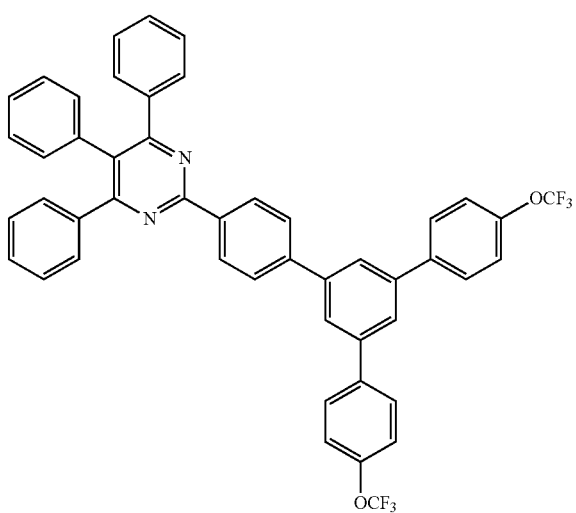
150
-continued
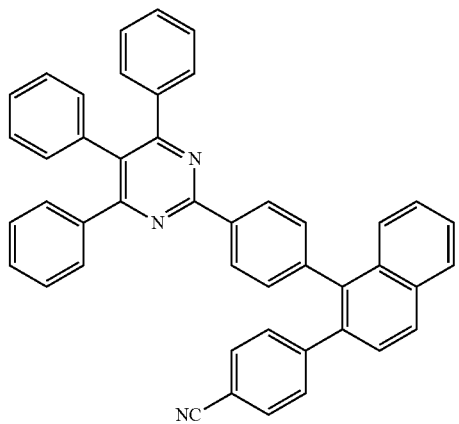
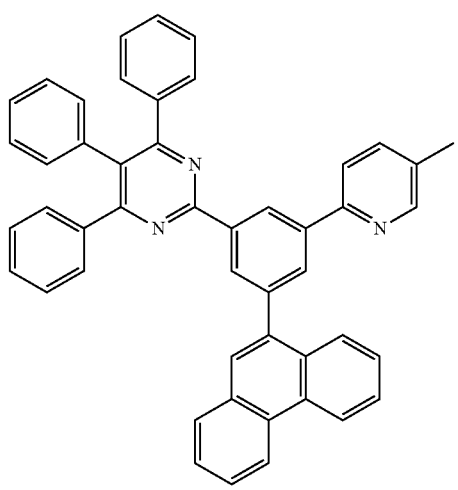
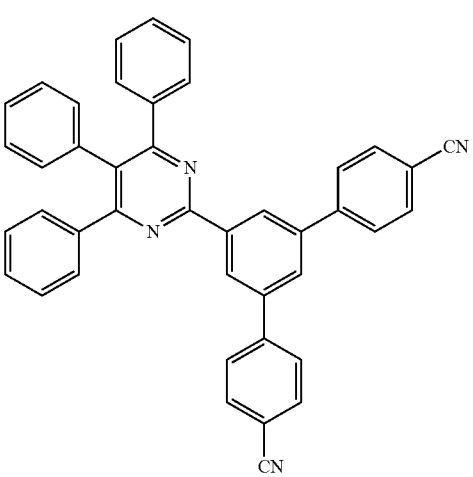

151
-continued
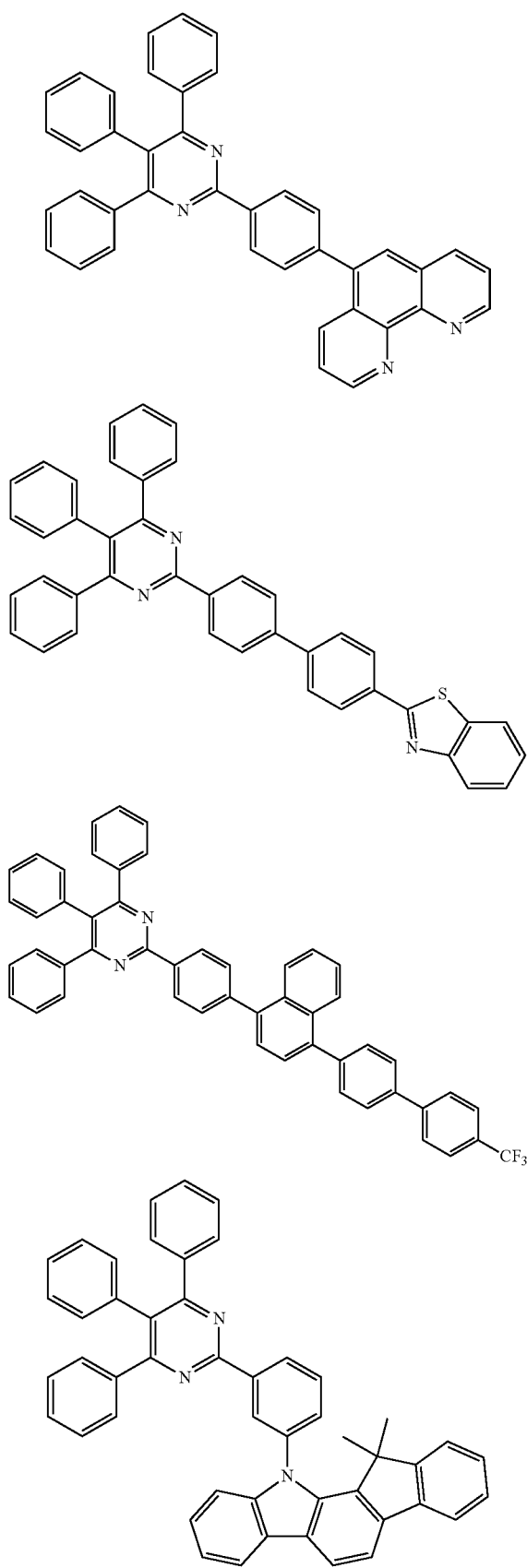
152
-continued
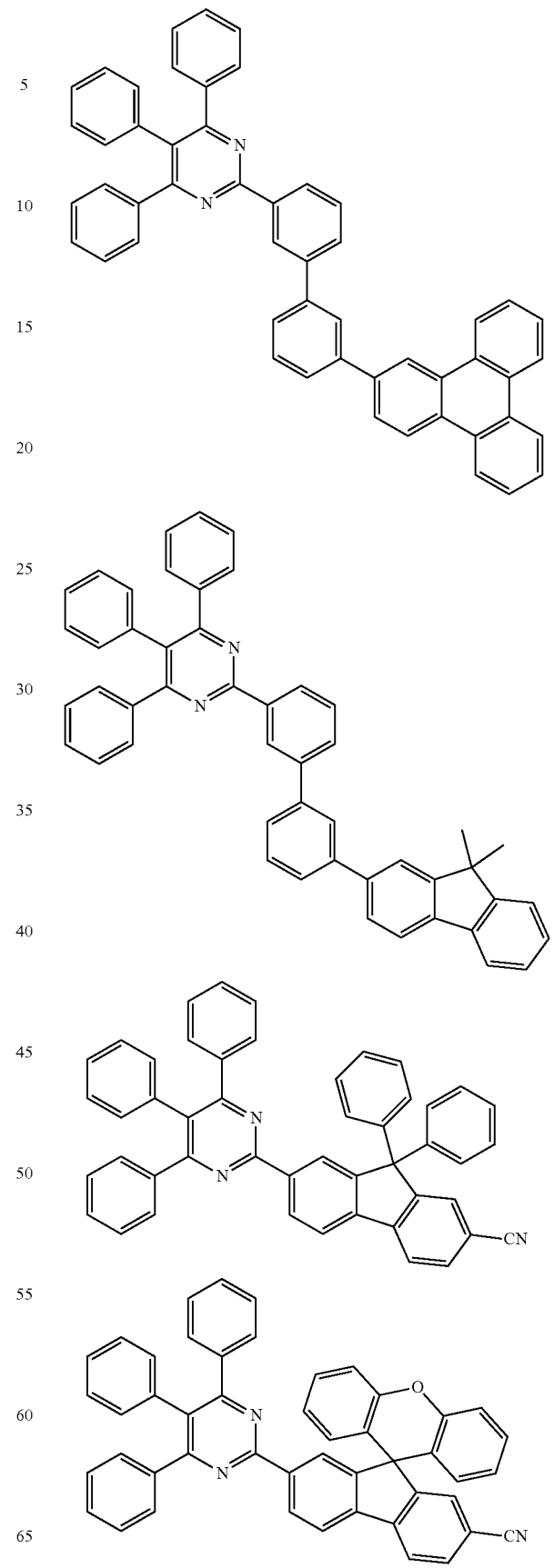

153
-continued
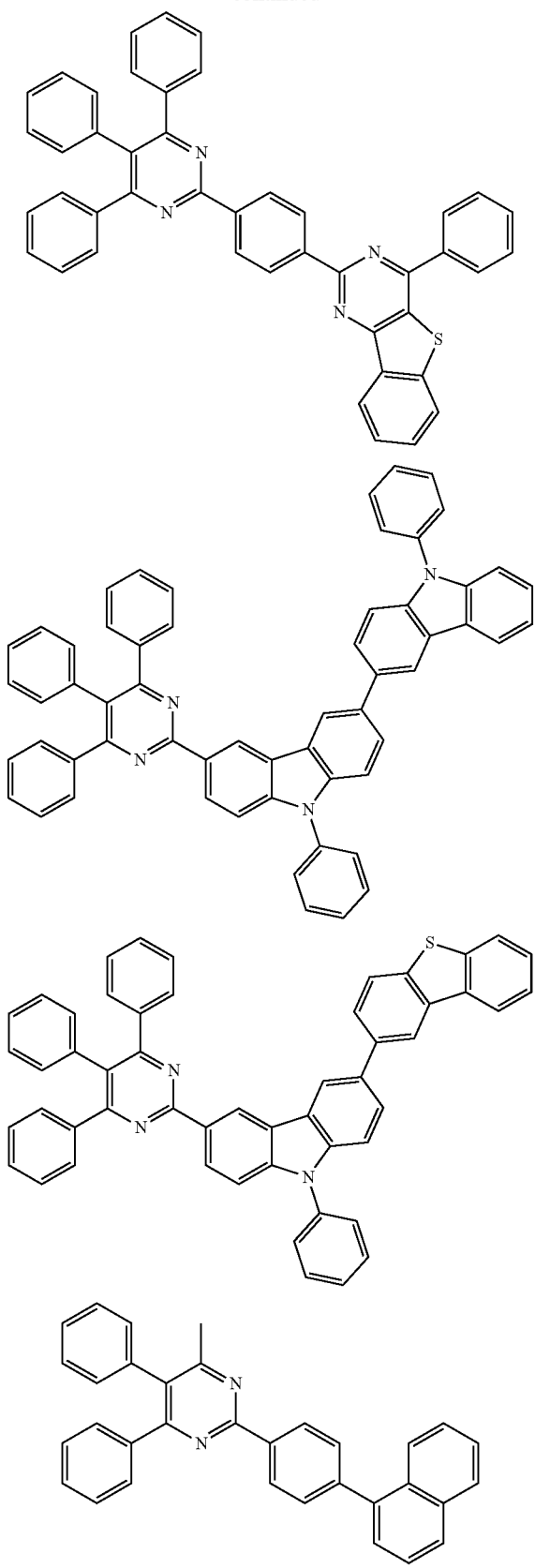
154
-continued
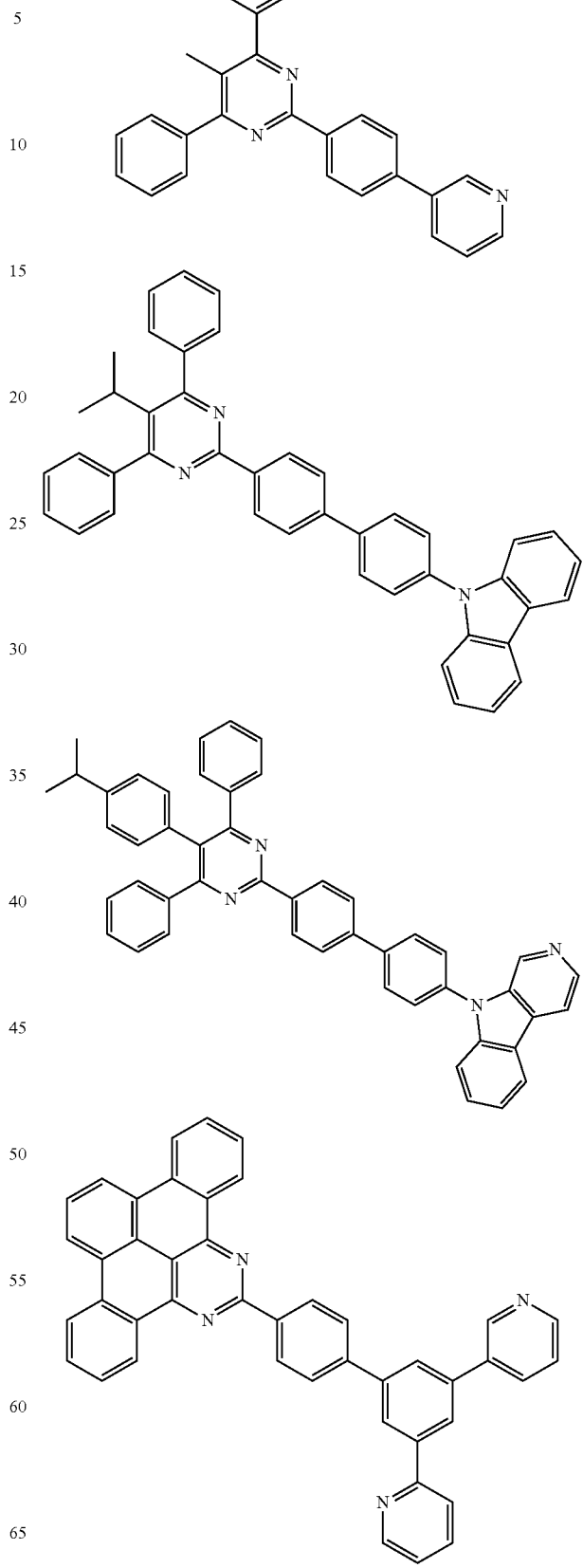

155
-continued
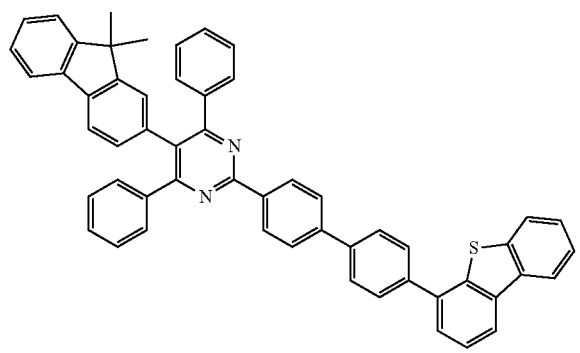
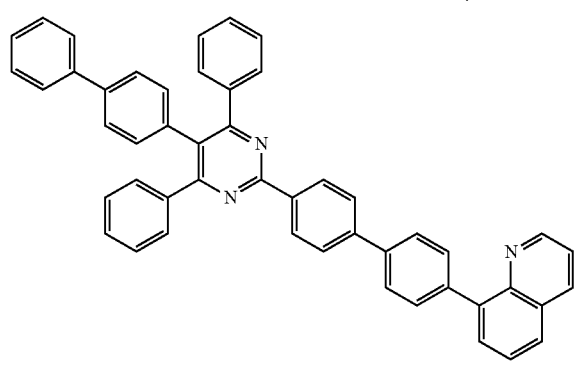
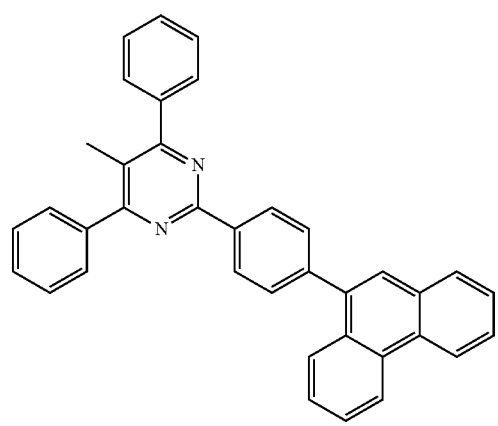
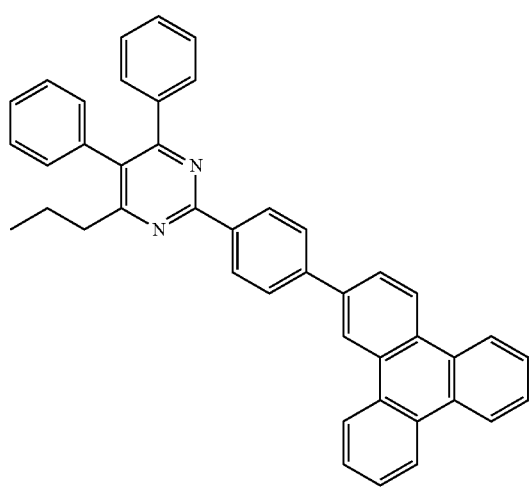
156
-continued
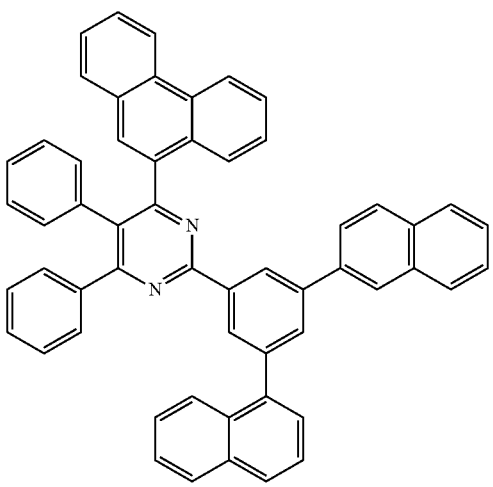
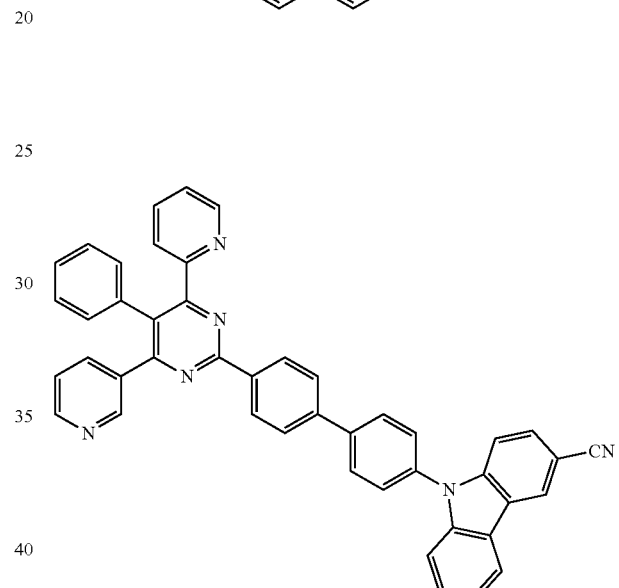
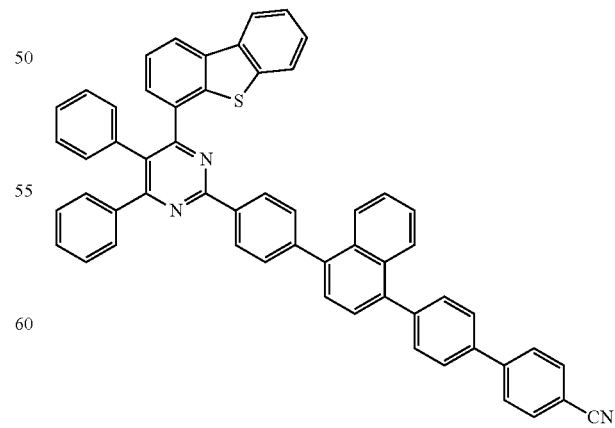

157
-continued

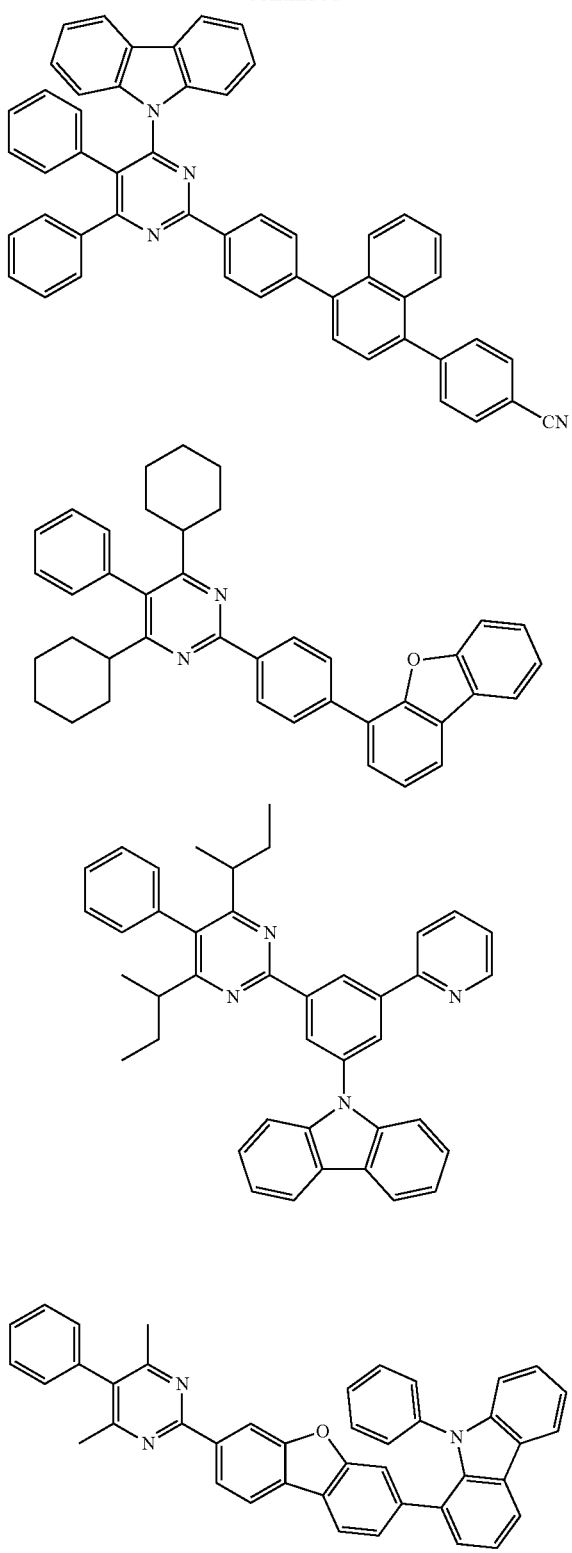

158
-continued

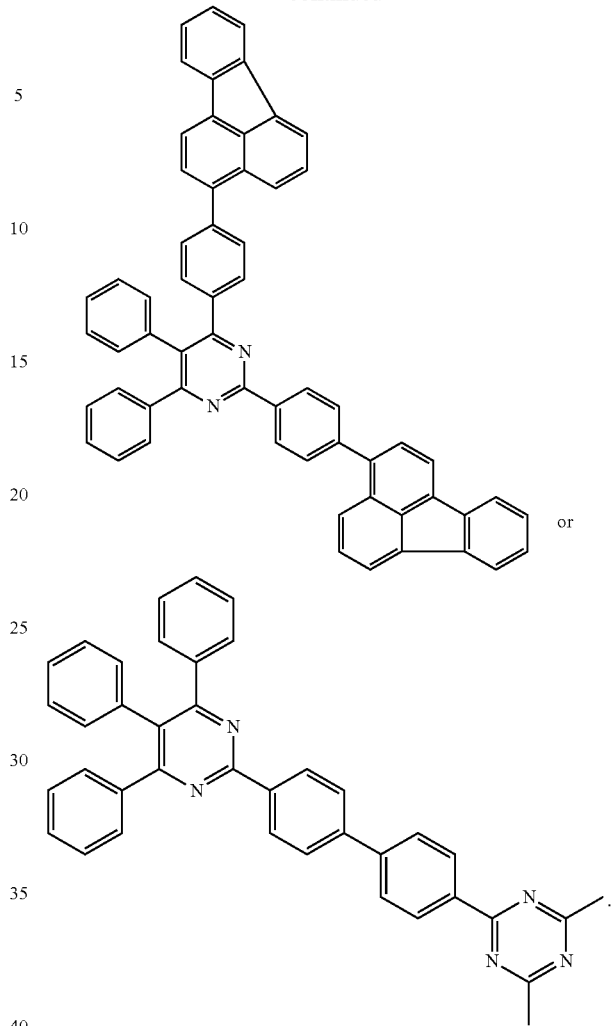

or

5. An organic light emitting device, comprising:
a first electrode;
a second electrode provided opposite to the first electrode; and
one or more organic material layers provided between the first electrode and the second electrode,
wherein the organic material layer comprises the compound of claim 1.

6. The organic light emitting device of claim 5, wherein the organic material layer comprises an electron injection layer, an electron transfer layer, or a layer carrying out electron injection and electron transfer at the same time, and the electron injection layer, the electron transfer layer, or the layer carrying out electron injection and electron transfer at the same time comprises the compound.

7. The organic light emitting device of claim 5, wherein the organic material layer comprises a hole blocking layer, and the hole blocking layer comprises the compound.

* * * * *